United States Patent
Tsai et al.

(10) Patent No.: US 10,727,423 B2
(45) Date of Patent: Jul. 28, 2020

(54) ORGANIC ELECTROLUMINESCENT MATERIALS AND DEVICES

(71) Applicant: UNIVERSAL DISPLAY CORPORATION, Ewing, NJ (US)

(72) Inventors: Jui-Yi Tsai, Newtown, PA (US); Eric A. Margulies, Philadelphia, PA (US); Zhiqiang Ji, Chalfont, PA (US); Alexey Borisovich Dyatkin, Ambler, PA (US); Walter Yeager, Yardley, PA (US); Mingjuan Su, Ewing, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 0 days.

(21) Appl. No.: 16/235,390

(22) Filed: Dec. 28, 2018

(65) Prior Publication Data

US 2019/0140191 A1     May 9, 2019

Related U.S. Application Data

(63) Continuation-in-part of application No. 15/728,737, filed on Oct. 10, 2017, which is a continuation-in-part of application No. 15/619,159, filed on Jun. 9, 2017.
(Continued)

(51) Int. Cl.
*H01L 51/00*     (2006.01)
*C07F 15/00*     (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
None
See application file for complete search history.

(56) References Cited

U.S. PATENT DOCUMENTS

| 4,769,292 A | 9/1988 | Tang et al. |
| 5,061,569 A | 10/1991 | VanSlyke et al. |

(Continued)

FOREIGN PATENT DOCUMENTS

| EP | 0650955 | 5/1995 |
| EP | 1725079 | 11/2006 |

(Continued)

OTHER PUBLICATIONS

Julia et al. "Developing strongly luminescent platinum(IV) complexes: facile synthesis of bis-cyclometalated neutral emitters" Chem. Commum. 2016, 52, 1657-1660. (Year: 2016).*
(Continued)

*Primary Examiner* — Robert S Loewe
(74) *Attorney, Agent, or Firm* — Duane Morris LLP

(57) ABSTRACT

A compound having a metal coordination complex structure, where the compound is capable of functioning as a phosphorescent emitter in an organic light emitting device at room temperature is disclosed. The compound has a first ligand coordinated to a metal. The free-state of the first ligand has a first triplet energy T1 of $E_L$ at 77K, while the compound has a first triplet energy T1 of E at 77K, and the difference in energy ($\Delta E$) between E and $E_L$ is $\leq 250$ meV. The compound has a triplet emission spectrum with a FWHM value of no more than 45 nm. Organic light emitting devices, consumer products, and formulations containing the compounds are also disclosed.

18 Claims, 2 Drawing Sheets

Related U.S. Application Data

(60) Provisional application No. 62/643,472, filed on Mar. 15, 2018, provisional application No. 62/352,119, filed on Jun. 20, 2016.

(51) Int. Cl.
*C09K 11/06* (2006.01)
*H01L 51/50* (2006.01)

(52) U.S. Cl.
CPC ...... *H01L 51/0052* (2013.01); *H01L 51/0054* (2013.01); *H01L 51/0058* (2013.01); *H01L 51/0067* (2013.01); *H01L 51/0071* (2013.01); *H01L 51/0072* (2013.01); *H01L 51/0074* (2013.01); *H01L 51/0094* (2013.01); *C09K 2211/1033* (2013.01); *C09K 2211/1037* (2013.01); *C09K 2211/185* (2013.01); *H01L 51/5016* (2013.01)

(56) References Cited

U.S. PATENT DOCUMENTS

| | | | |
|---|---|---|---|
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 8,692,241 B1 * | 4/2014 | Zeng ............... | C09K 11/06 257/40 |
| 8,946,697 B1 * | 2/2015 | Ma .................. | C07F 15/0033 257/40 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2010/0219407 A1 * | 9/2010 | Kamatani ............. | C07C 17/14 257/40 |
| 2010/0244004 A1 * | 9/2010 | Xia .................... | C07F 15/0033 257/40 |
| 2011/0204333 A1 * | 8/2011 | Xia .................... | C07F 15/0033 257/40 |
| 2012/0061654 A1 * | 3/2012 | Rayabarapu ........ | C07F 15/0033 257/40 |
| 2012/0205645 A1 * | 8/2012 | Fuchs ................ | C07F 15/0033 257/40 |
| 2012/0292601 A1 * | 11/2012 | Kottas ............... | H01L 51/0085 257/40 |
| 2012/0302753 A1 * | 11/2012 | Li ..................... | C07F 15/0086 546/4 |
| 2013/0026452 A1 * | 1/2013 | Kottas .................. | C09K 11/06 257/40 |
| 2013/0119354 A1 * | 5/2013 | Ma ..................... | C07F 15/0033 257/40 |
| 2014/0131676 A1 * | 5/2014 | Beers ................. | H01L 51/0085 257/40 |
| 2014/0131687 A1 * | 5/2014 | Lin ..................... | C07F 15/0033 257/40 |
| 2014/0231755 A1 * | 8/2014 | Xia .................... | H01L 51/0085 257/40 |
| 2015/0008419 A1 * | 1/2015 | Li ..................... | H01L 51/5016 257/40 |
| 2015/0137096 A1 * | 5/2015 | Xia .................... | H01L 51/0085 257/40 |
| 2015/0162552 A1 * | 6/2015 | Li ..................... | H01L 51/0087 546/4 |
| 2015/0236276 A1 * | 8/2015 | Boudreault ......... | H01L 51/0085 257/40 |
| 2015/0357576 A1 | 12/2015 | Kawamura et al. | |
| 2015/0364702 A1 * | 12/2015 | Abe .................... | C09K 11/06 257/40 |
| 2016/0049597 A1 | 2/2016 | Ma et al. | |
| 2016/0049599 A1 | 2/2016 | Ma et al. | |
| 2016/0260907 A1 | 9/2016 | Low et al. | |
| 2016/0359123 A1 * | 12/2016 | Thompson .......... | H01L 51/0085 |
| 2017/0373259 A1 | 12/2017 | Su et al. | |
| 2018/0254417 A1 | 9/2018 | Ma et al. | |
| 2019/0051844 A1 | 2/2019 | Ji et al. | |

FOREIGN PATENT DOCUMENTS

| | | |
|---|---|---|
| EP | 2034538 | 3/2009 |
| EP | 2594573 | 5/2013 |
| EP | 2982729 | 2/2016 |
| JP | 200511610 | 1/2005 |
| JP | 2007123392 | 5/2007 |
| JP | 2007254297 | 10/2007 |

(56) References Cited

FOREIGN PATENT DOCUMENTS

| | | |
|---|---|---|
| JP | 2008074939 | 4/2008 |
| JP | 2012-74444 | 4/2012 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2016080785 | 5/2016 |

OTHER PUBLICATIONS

Tsuboyama et al. "Homoleptic Cyclometalated Iridium Complexes with Highly Efficient Red Phosphorescence and Application to Organic Light-Emitting Diode" J. Am. Chem. Soc. 2003, 125, 12971-12979. (Year: 2003).*

Winkler et al. "Gas phase pyrolysis of heterocyclic compounds, part 4: flow of pyrolysis and annulation reactions of some oxygen heterocycles: furan, benzo[b]furan and dibenzofuran. A product oriented study.", Journal of Analytical and Applied Pyrolysis, vol. 57, Issue 1, Jan. 2001, pp. 133-144.

Velusamy et al., "Synthesis, structure and electroluminescent properties of cyclometalated iridium complexes possessing sterically hindered ligands", Dalton Transactions, 2007, 28, pp. 3025-3034.

Zeng, Qun et al., "Spin-orbit coupling effect on Au—C60 interaction: A density functional theory study," Chemical Physics 395 (2012) pp. 82-86.

Extended European Search Report dated Jul. 10, 2019 for corresponding European Application No. 19161973.3.

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)indium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

(56) References Cited

OTHER PUBLICATIONS

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91: 209-215 (1997).

Shirota, Yasuhiko et al., "Starburst Molecules Based on pi-Electron Systems as Materials for Organic Electroluminescent Devices," Journal of Luminescence, 72-74:985-991 (1997).

Sotoyama, Wataru et al., "Efficient Organic LIght-Emitting Diodes with Phosphorescent Platinum Complexes Containing N^C^N-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 88:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69(15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

ORGANIC ELECTROLUMINESCENT MATERIALS AND DEVICES

CROSS-REFERENCE TO RELATED APPLICATIONS

This application claims priority under 35 U.S.C. § 119(e) to U.S. Provisional Application No. 62/643,472, filed Mar. 15, 2018, and this application is a continuation-in-part of U.S. patent Ser. No. 15/728,737, filed Oct. 10, 2017, which is a continuation-in-part of U.S. patent Ser. No. 15/619,159, filed Jun. 9, 2017, which is a non-provisional of U.S. Provisional Application No. 62/352,119, filed Jun. 20, 2016, the entire contents of which are incorporated herein by reference.

FIELD

The present invention relates to compounds for use as emitters, and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted Ir(ppy)$_3$, which has the following structure:

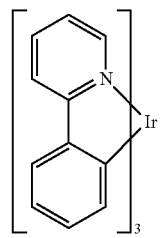

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

According to an aspect of the present disclosure, a compound having a metal coordination complex structure, where the compound is capable of functioning as a phosphorescent emitter in an organic light emitting device at room temperature is disclosed. The compound has a first ligand coordinated to a metal. The free-state of the first ligand has a first triplet energy T1 of $E_L$ at 77K, while the compound has a first triplet energy T1 of E at 77K, and the difference in energy ($\Delta E$) between E and $E_L$ is ≤250 meV. The compound has a triplet emission spectrum with a FWHM value of no more than 45 nm.

An OLED comprising the compound of the present disclosure in an organic layer therein is also disclosed.

A consumer product comprising the OLED is also disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
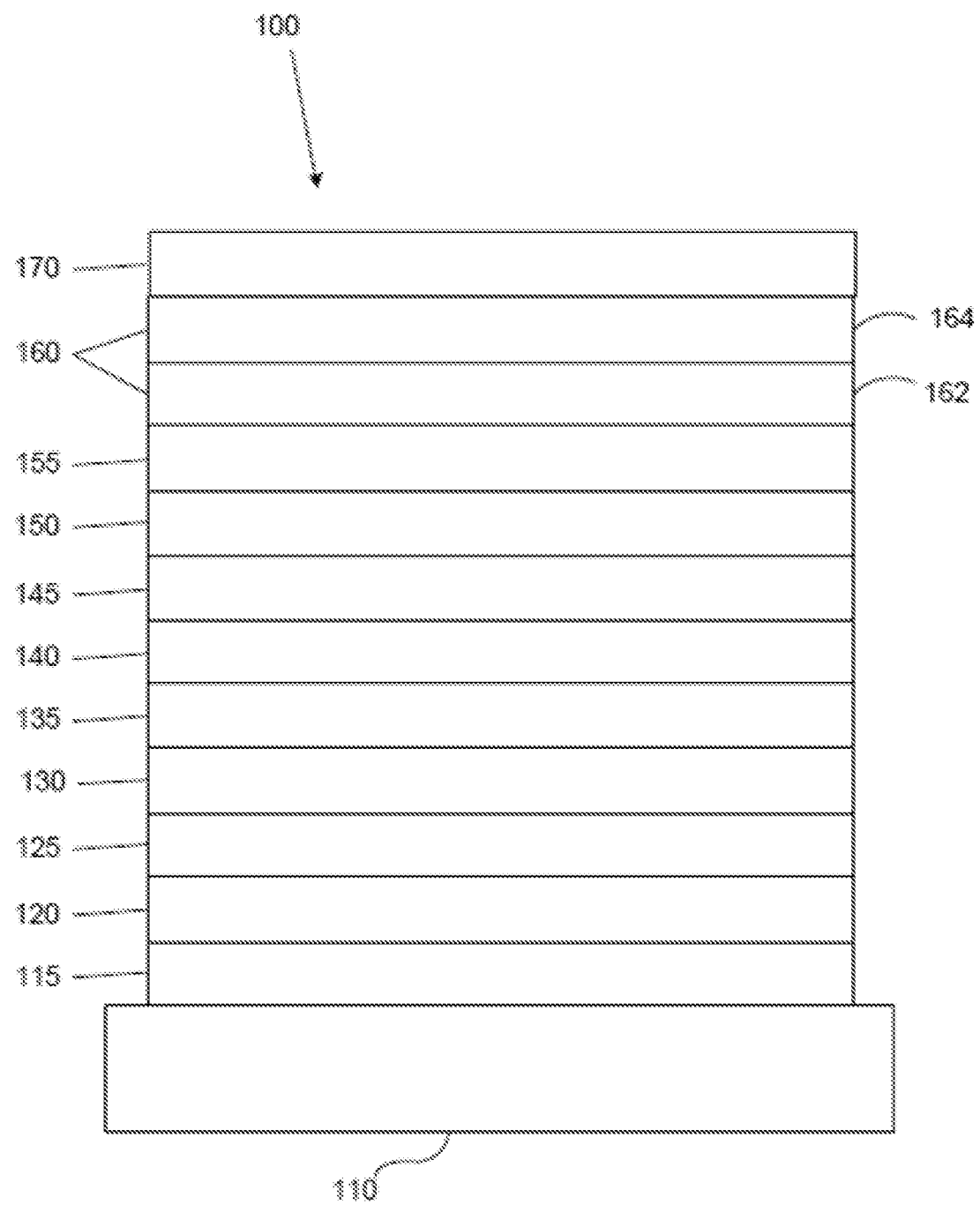
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
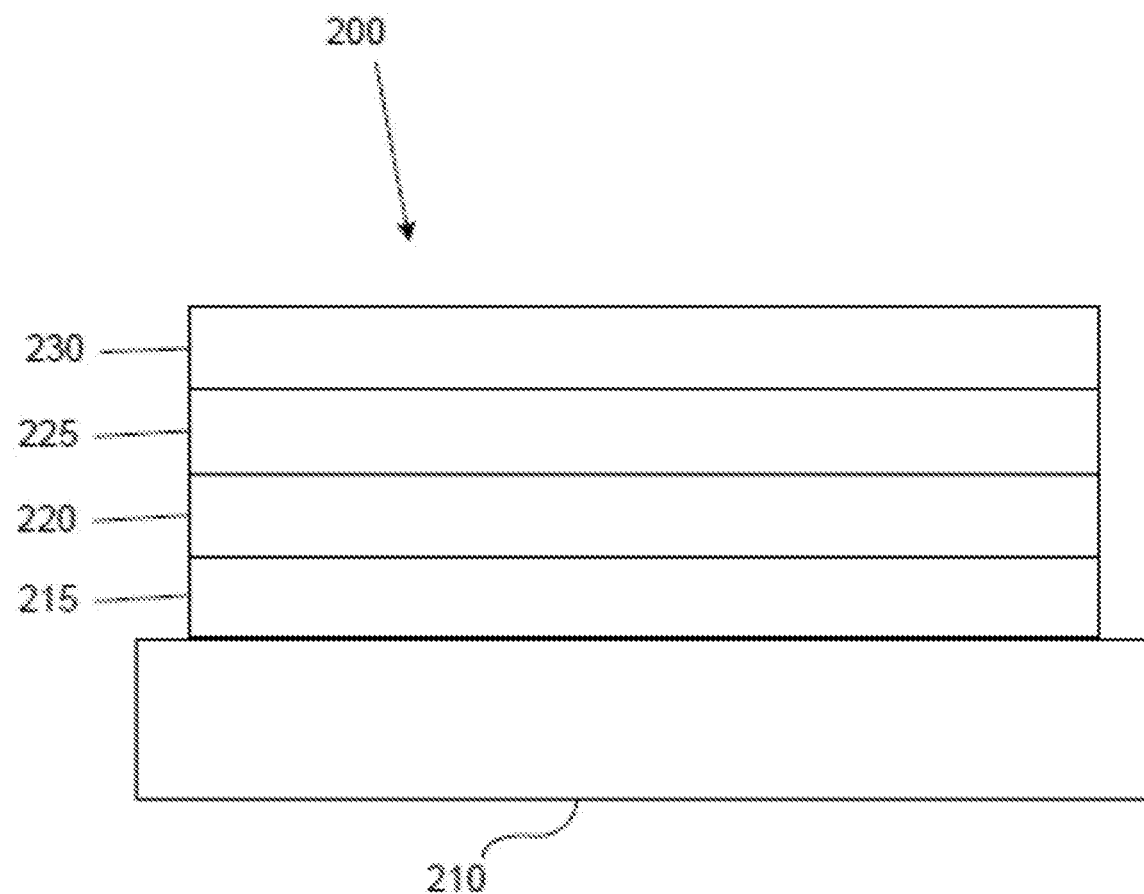
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms "halo," "halogen," and "halide" are used interchangeably and refer to fluorine, chlorine, bromine, and iodine.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —O$R_s$ radical.

The terms "sulfanyl" or "thio-ether" are used interchangeably and refer to a —S$R_s$ radical.

The term "sulfinyl" refers to a —S(O)—$R_s$ radical.

The term "sulfonyl" refers to a —SO$_2$—$R_s$ radical.

The term "phosphino" refers to a —P($R_s$)$_3$ radical, wherein each R can be same or different.

The term "silyl" refers to a —Si($R_s$)$_3$ radical, wherein each $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group is optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo [3.1.1]heptyl, spiro[4.5]decyl, spiro[5.5]undecyl, adamantyl, and the like. Additionally, the cycloalkyl group is optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group is optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group is optionally substituted.

The term "alkynyl" refers to and includes both straight and branched chain alkyne radicals. Preferred alkynyl groups are those containing two to fifteen carbon atoms. Additionally, the alkynyl group is optionally substituted.

The terms "aralkyl" or "arylalkyl" are used interchangeably and refer to an alkyl group that is substituted with an aryl group. Additionally, the aralkyl group is optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group is optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group is optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed.* (*Reviews*) 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

For many OLED display applications, the emission color, which may be described in terms of 1931 CIE color space, is a critical parameter for adoption of a given phosphorescent emitter. The efficiency and color gamut of a display are codependent on the spectra of the emitters within the device. As such, there are numerous advantages to increasing the color purity (spectral narrowness) of an emitter.

Assuming an OLED device with weak or negligible microcavity effects, the advantages are straightforward. As compared to a spectrally broad emitter with the same peak emission wavelength, a narrow emitter will be able to achieve greater color purity, and thus a larger color gamut. Conversely, the same color gamut may be achieved with a red-shifted emitter, which may result in a longer device lifetime due to a lower energy exciton.

In a microcavity enhanced OLED device, the benefit of a narrow emission spectrum is twofold. First, just as in the weak microcavity device, a narrow emission spectrum results in a greater spectral purity and thus a larger color gamut and/or longer device lifetime. Second, the more narrow the emission spectrum, the more of this spectrum is resonant with the microcavity spectrum which results in an enhanced Purcell factor and thus a shorter emission rate and higher device efficiency. For these reasons, it is very desirable to generate phosphorescent emitters with narrow emission spectra.

Here we claim compounds that achieve such narrow emission spectra, which may be described in terms of the electroluminescent spectral full width at half maximum (FWHM), by increasing the ligand contribution to the emitter excited state. Rigid organic emitters are capable of very narrow emission spectra (<50 nm) whereas many organometallic phosphorescent emitters with a high degree of metal-to-ligand charge transfer (MLCT) character possess relatively broad emission spectra (>70 nm). However, this problem of a broad emission spectra may be mitigated by the use of a phosphorescent emitter which has an emissive ligand ($L_B$) with a relatively low energy triplet state. Given a thermally accessible gap ($\Delta E$) between the ligand centered triplet state energy ($E_L$) and the complex emissive state energy (E), this state may have higher ligand centered (LC) character, and thus more narrow emission spectrum.

This narrow, high LC character, emission spectrum comes at the expense of a longer excited state lifetime due to the decreased spin-orbit coupling of an E-state with less MLCT character. As a longer excited state lifetime may result in increased quenching and device roll-off, a balance must be struck between the FWHM and transient lifetime. Both of these factors considered, it is desirable to have a FWHM<40 nm, more preferably <30 nm and more preferably <20 nm; as well as a transient lifetime <14 µs, more preferably <11 µs, and more preferably <8 µs. The FWHM described herein is measured by electroluminescent (EL) measurement of a bottom emission device at room temperature (~22° C.). More specifically, for each color emission emitters, the devices are fabricated as follow:

For blue ($\lambda_{max}$<500 nm) the anode electrode is 750 Å of indium tin oxide (ITO). The cathode is 10 Å of Liq (8-hydroxyquinoline lithium) followed by 1,000 Å of Al. All devices are encapsulated with a glass lid sealed with an epoxy resin in a nitrogen glove box (<1 ppm of $H_2O$ and $O_2$) immediately after fabrication, and a moisture getter is incorporated inside the package. The organic stack of the device examples consists of sequentially, from the ITO surface, 100 Å of HAT-CN as the hole injection layer (HIL); 250 Å of HTM as a hole transporting layer (HTL); 400 Å of an emissive layer (EML) containing either host H1 or H2 and 15% blue emitter; 250 Å of H1 as a blocking layer (BL); and 300 Å of $Alq_3$ (Tris(8-hydroxyquinolinato)aluminium) as the ETL.

For red ($\lambda_{max}$≥590 nm) and green ($\lambda_{max}$ 500-590 nm), the anode electrode is 750 Å (green) or 1,150 Å (red) of ITO. The cathode is 10 Å of Liq (8-hydroxyquinoline lithium) followed by 1,000 Å of Al. All devices are encapsulated with a glass lid sealed with an epoxy resin in a nitrogen glove box (<1 ppm of $H_2O$ and $O_2$) immediately after fabrication, and a moisture getter is incorporated inside the package. The organic stack of the device examples consists of sequentially, from the ITO surface, 100 Å of HAT-CN as the hole injection layer (HIL); 400 Å of HTM as a hole transporting layer (HTL); 50 Å of EBM as an electron blocking layer (EBL); 400 Å of an emissive layer (EML) containing either red host H3 and 3% red emitter or green host H4 doped with 40% H5 and 12% green emitter, and 350 Å of Liq (8-hydroxyquinoline lithium) doped with 35% of ETM as the ETL.

The molecular structures used in the above devices are shown below:

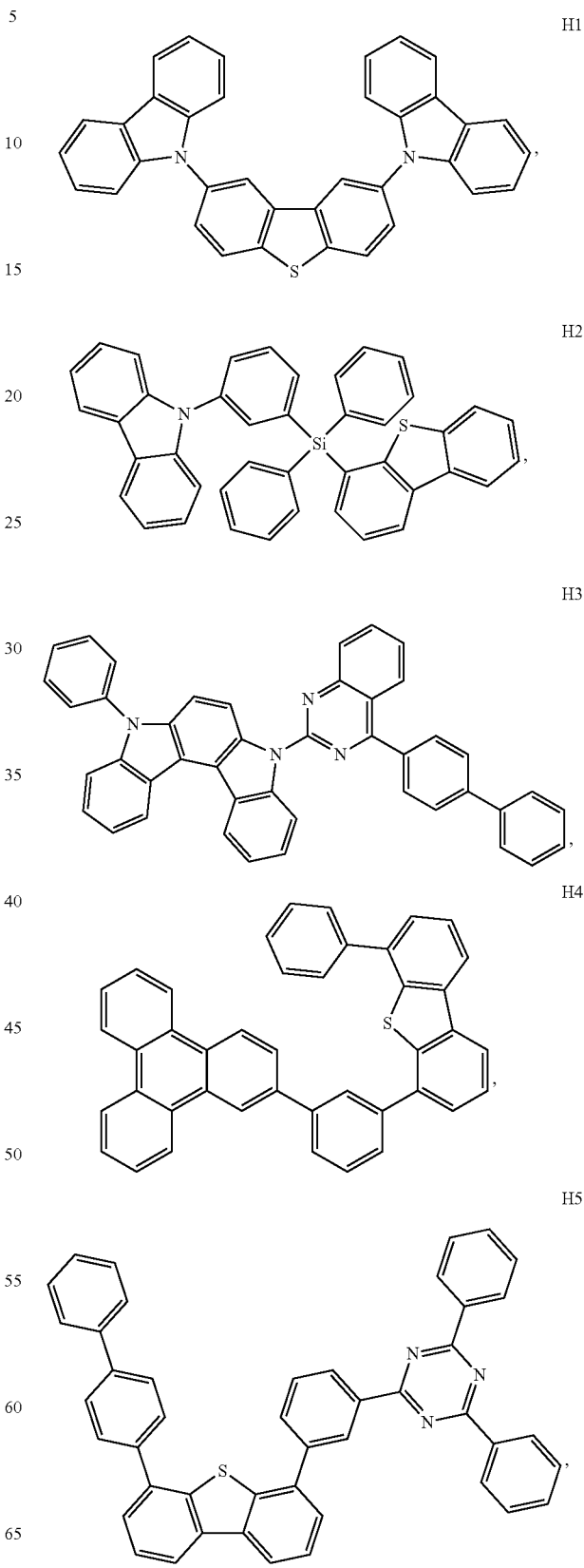

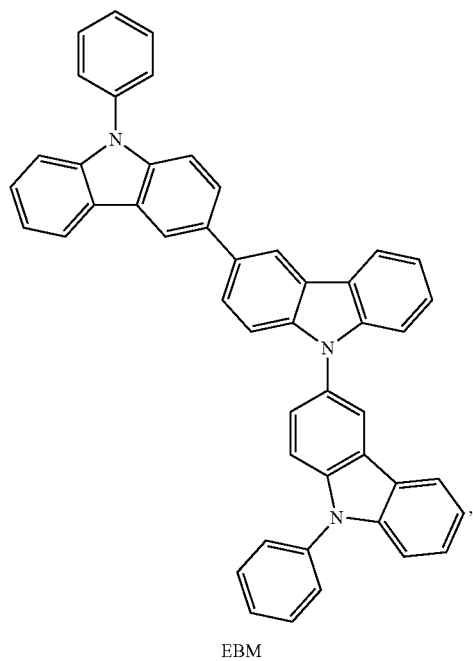

EBM

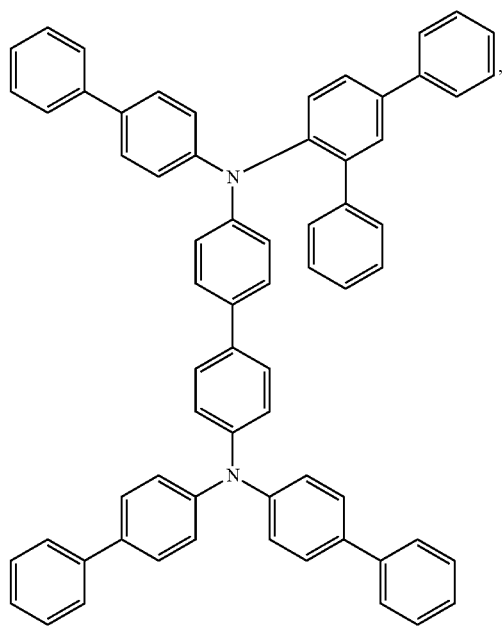

HTM

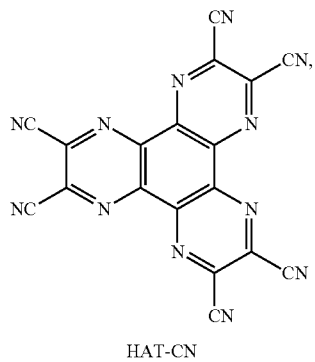

HAT-CN

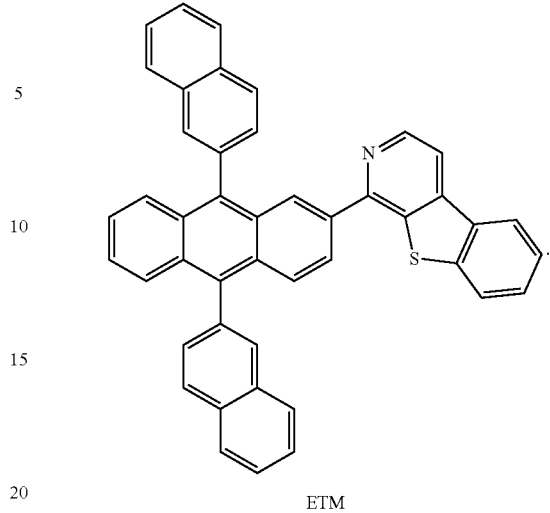

ETM

These parameters may be achieved through judicious tuning of the MLCT state and LC state energies as the relative energies of these two states are highly correlated with their contribution to the emissive state character E, as described above. We can directly measure two of these three states, making this method both measurable and confirmable. The energy of the LC triplet state may be measured by the 10% onset of the emission peak in the low temperature (77K) photoluminescence of the non-ligated ligand in the presence of methyl iodide (to increase intersystem crossing) and the energy of the E state may be measured by the 10% onset of the emission peak in the complex photoluminescence spectrum. These measurements provide the framework for designing an emitter with the designed narrow emission spectrum.

According to an aspect of the present disclosure, a compound having a metal coordination complex structure, where the compound is capable of functioning as a phosphorescent emitter in an organic light emitting device at room temperature is disclosed. The compound has a first ligand coordinated to a metal. The free-state of the first ligand has a first triplet energy T1 of $E_L$ at 77K, while the compound has a first triplet energy T1 of E at 77K, and the difference in energy ($\Delta E$) between E and $E_L$ is ≤250 meV. The compound has a triplet emission spectrum with a FWHM value of no more than 45 nm. The values of $E_L$, E, and FWHM are measured based on the methods and conditions described above.

As used herein, when used in reference to a ligand, the phrase "free-state" refers to the ligand of the compound where the bonds between the metal and the ligand are replaced by H.

In some embodiments, $\Delta E$ is ≤200 meV. In some embodiments, $\Delta E$ is ≤160 meV. In some embodiments, $\Delta E$ is ≤150 meV, or $\Delta E$ is ≤140 meV, or $\Delta E$ is ≤130 meV, or $\Delta E$ is ≤120 meV, or $\Delta E$ is ≤110 meV, or $\Delta E$ is ≤100 meV, or $\Delta E$ is ≤90 meV, or $\Delta E$ is ≤80 meV, or $\Delta E$ is ≤70 meV, or $\Delta E$ is ≤60 meV, or $\Delta E$ is ≤50 meV, or $\Delta E$ is ≤40 meV, or $\Delta E$ is ≤30 meV.

In some embodiments, the compound has a triplet emission spectrum with a FWHM value of no more than 40 nm. In some embodiments, the compound has a triplet emission spectrum with a FWHM value of no more than 35 nm, or no more than 30 nm, or no more than 25 nm, or no more than 20 nm, or no more than 15 nm, or no more than 10 nm.

In some embodiments, the compound has a metal-carbon bond. In some embodiments, the metal is selected from the group consisting of Ir, Rh, Re, Ru, Os, Pt, Pd, Au, Ag, and Cu. In some embodiments, the metal is Ir, while the metal is Pt in other embodiments.

In some embodiments, the compound has a neutral charge. In some embodiments, the compound is homoleptic. In some embodiments, the compound is heteroleptic.

In some embodiments, the compound has an octahedral coordination geometry formed by (i) three bidentate ligands, (ii) two tridentate ligands, (iii) one tetradentate and one bidentate ligands, or (iv) one hexadentate ligand. In some embodiments, the compound has a square planar coordination geometry formed by two bidentate ligands or one tetradentate ligand. In some embodiments, the first ligand is a bidentate ligand. In some embodiments, the first ligand is a tridentate ligand. In some embodiments, the first ligand is a tetradentate ligand.

In some embodiments, the compound comprises a first benzene ring coordinated to the metal, where the first benzene ring is fused with a second aromatic ring. In some embodiments with a fused second ring, the second aromatic ring is fused with a third aromatic ring. In some embodiments with a fused second ring, the third aromatic ring is fused with a fourth aromatic ring. In some embodiments with a fused second ring, the second aromatic ring is a five-membered ring.

In some embodiments, the compound comprises a pyridine ring coordinated to the metal. In some such embodiments, the pyridine ring is substituted with at least one group selected from the group consisting of alkyl, cycloalkyl, fully or partially deuterated variants thereof, and combination thereof.

In some embodiments, the compound has a formula of $M(L_A)_x(L_B)_y(L_C)_z$, wherein $L_A$, $L_B$ and $L_C$ are each a bidentate ligand; and wherein x is 1, 2, or 3; y is 0, 1, or 2; z is 0, 1, or 2; and x+y+z is the oxidation state of the metal M. In some such embodiments, the compound has a formula selected from the group consisting of $Ir(L_A)_3$, $Ir(L_A)(L_B)_2$, $Ir(L_A)_2(L_B)$, $Ir(L_A)_2(L_C)$, and $Ir(L_A)(L_B)(L_C)$; and wherein $L_A$, $L_B$, and $L_C$ are different from each other. In some embodiments where the compound has the formula of $M(L_A)_x(L_B)_y(L_C)_z$, the compound has a formula of $Pt(L_A)(L_B)$; and wherein $L_A$ and $L_B$ can be same or different.

In some embodiments where the compound has the formula of $M(L_A)_x(L_B)_y(L_C)_z$, $L_A$ and $L_B$ are connected to form a tetradentate ligand. In some such embodiments, $L_A$ and $L_B$ are connected at two places to form a macrocyclic tetradentate ligand.

In some embodiments where the compound has the formula of $M(L_A)_x(L_B)_y(L_C)_z$, $L_A$, $L_B$, and $L_C$ are each independently selected from the group consisting of:

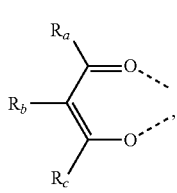
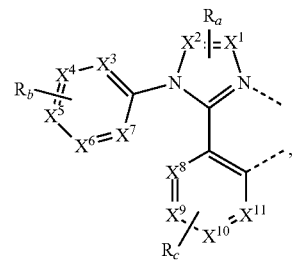
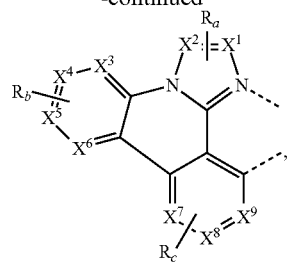
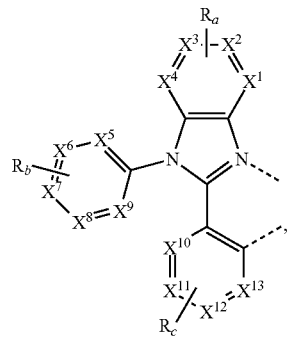
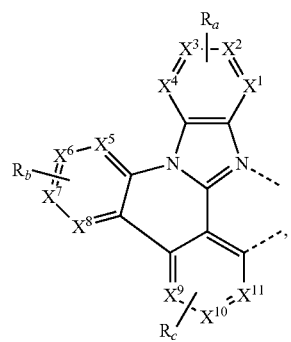
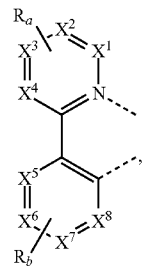
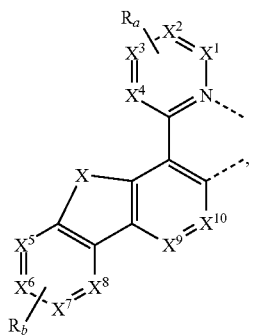
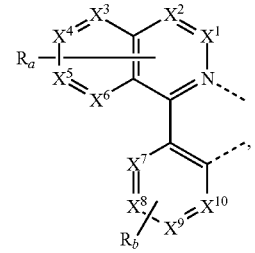
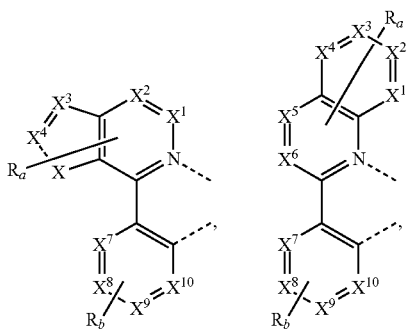

-continued

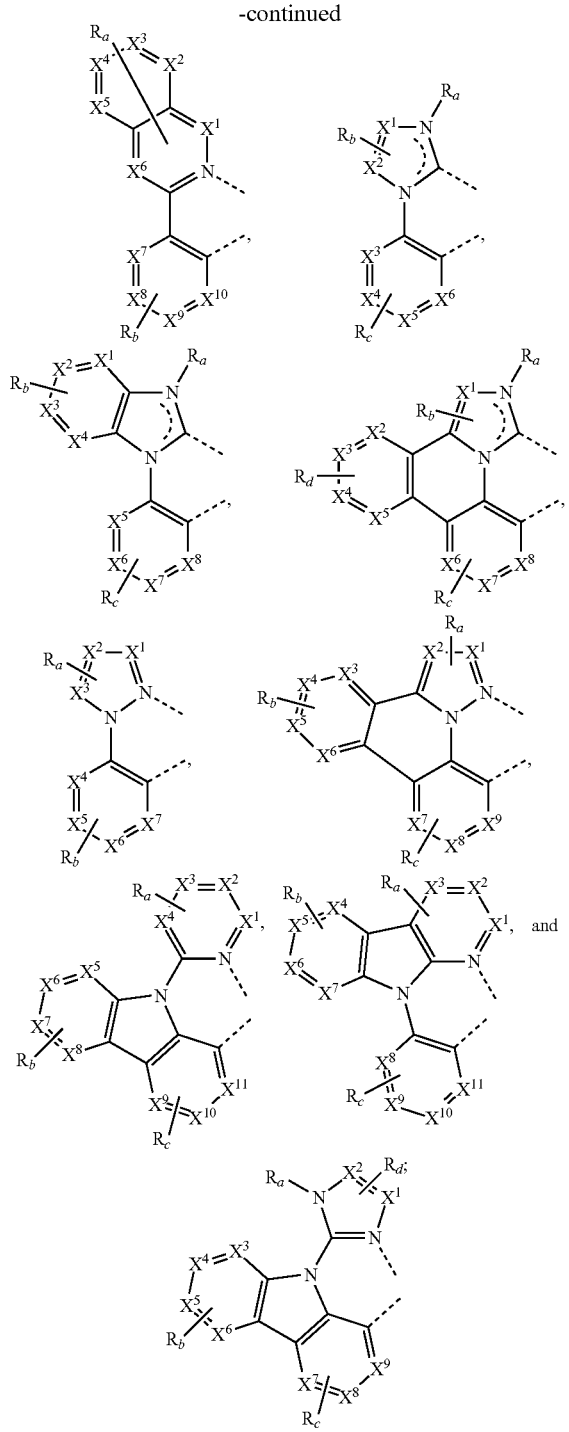

where each $X^1$ to $X^{13}$ are independently selected from the group consisting of carbon and nitrogen;

where X is selected from the group consisting of BR', NR', PR', O, S, Se, C=O, S=O, SO$_2$, CR'R", SiR'R", and GeR'R";

where R' and R" are optionally fused or joined to form a ring;

where each $R_a$, $R_b$, $R_c$, and $R_d$ may represent from mono substitution to the maximum possible number of substitution, or no substitution;

where R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and where any two adjacent substituents of $R_a$, $R_b$, $R_c$, and $R_d$ are optionally fused or joined to form a ring or form a multidentate ligand.

In some embodiments, at least one pair of substituents $R_a$, $R_b$, $R_c$, and $R_d$ within the same ring are joined and fused into a ring. In some embodiments, the compound has the formula of $Ir(L_A)_2(L_B)$.

In some embodiments. $L_A$ has the formula

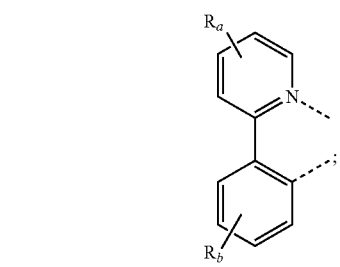

and $L_B$ is different from $L_A$, and has a formula selected from the group consisting of

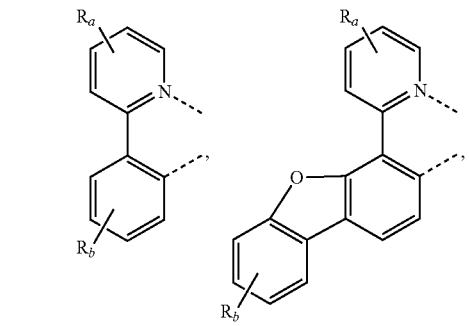

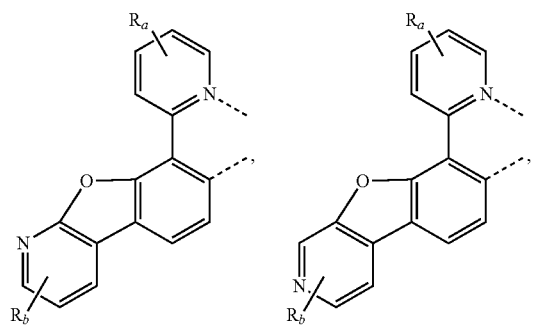

-continued

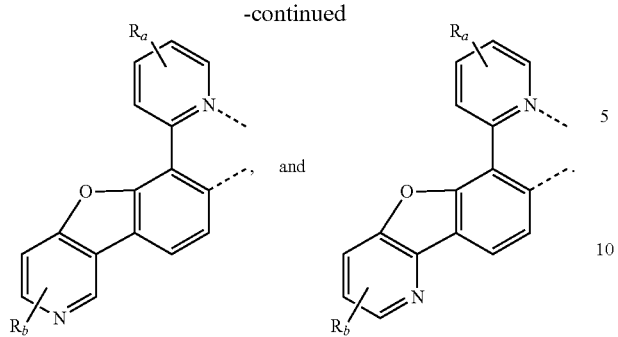
and

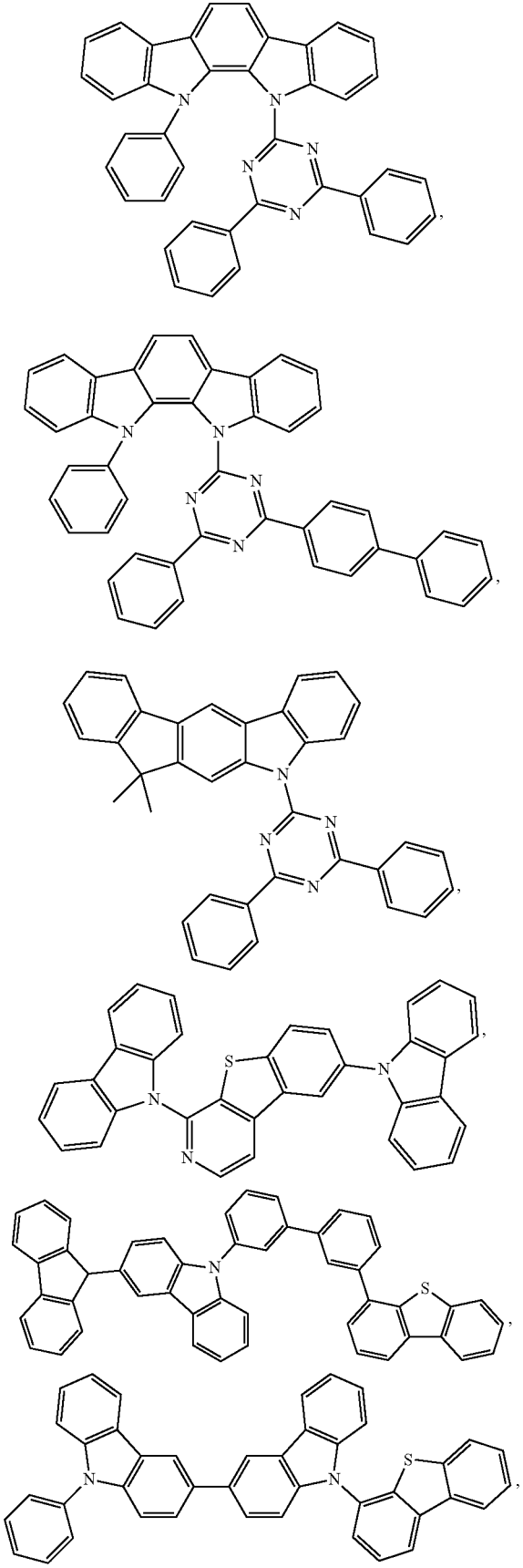

In some embodiments, an organic light emitting device (OLED) is described. The OLED can include an anode; a cathode; and an organic layer, disposed between the anode and the cathode, where the organic layer includes a compound comprising a first ligand $L_A$ of Formula I as described herein.

In some embodiments, a consumer product comprising an OLED as described herein is described.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

According to another aspect, an emissive region in an OLED (e.g., the organic layer described herein) is disclosed. The emissive region comprises a compound comprising a first ligand $L_A$ of Formula I as described herein. In some embodiments, the first compound in the emissive region is an emissive dopant or a non-emissive dopant. In some embodiments, the emissive dopant further comprises a host, wherein the host comprises at least one selected from the group consisting of metal complex, triphenylene, carbazole, dibenzothiophene, dibenzofuran, dibenzoselenophene, aza-triphenylene, aza-carbazole, aza-dibenzothiophene, aza-dibenzofuran, and aza-dibenzoselenophene. In some embodiments, the emissive region further comprises a host, wherein the host is selected from the group consisting of:

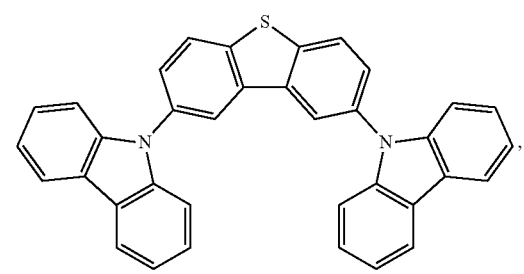

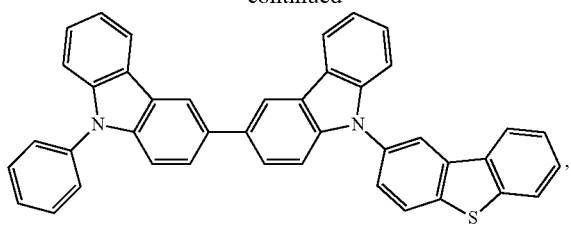
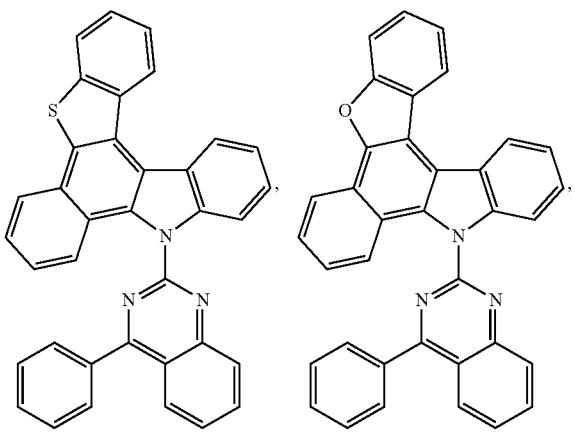
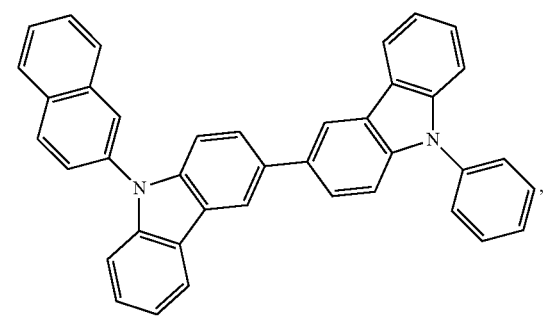
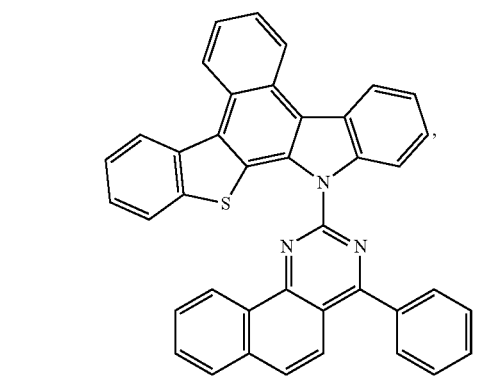
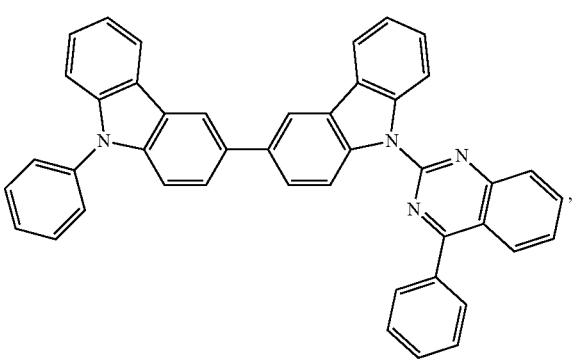
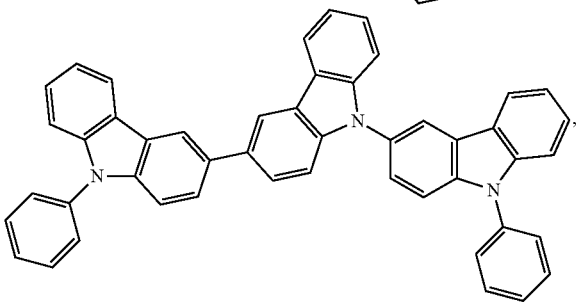

-continued

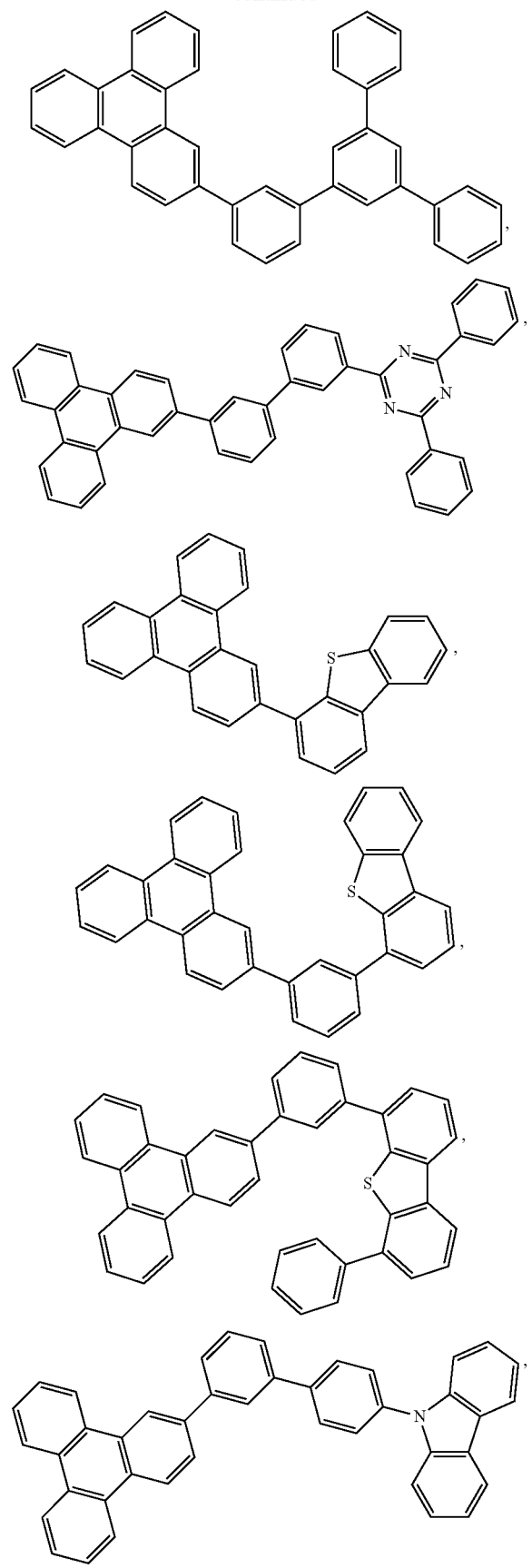

and combinations thereof.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

The organic layer can also include a host. In some embodiments, two or more hosts are preferred. In some embodiments, the hosts used may be a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$, or the host has no substitutions. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. The host can be an inorganic compound. For example a Zn containing inorganic material e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be, but is not limited to, a specific compound selected from the group consisting of:

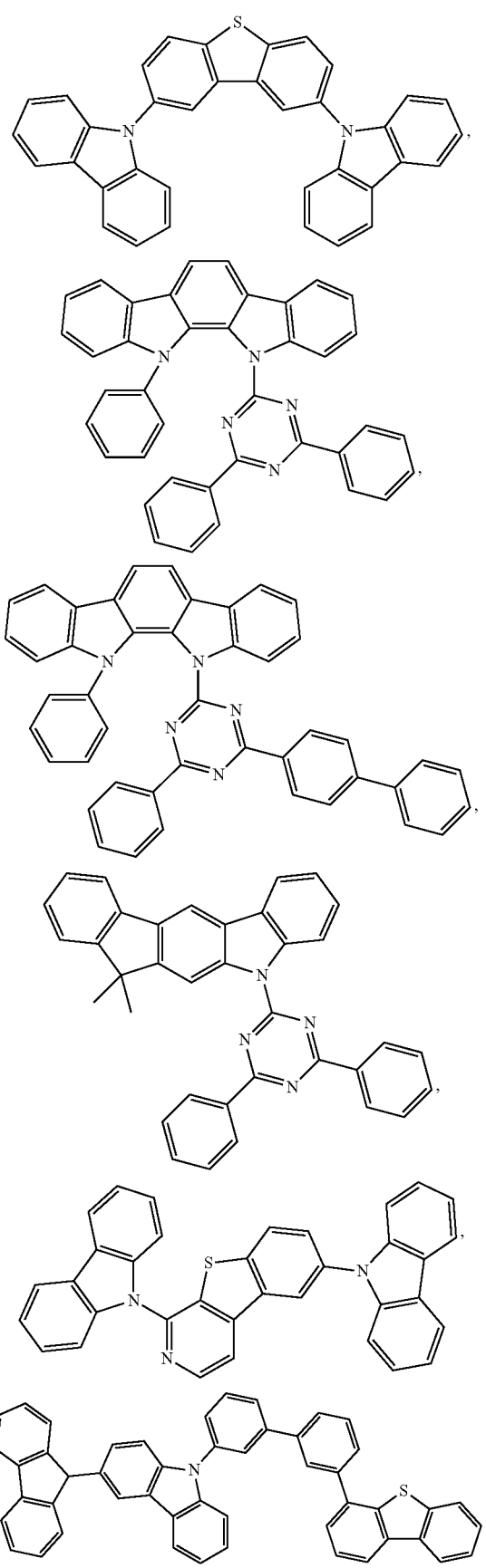
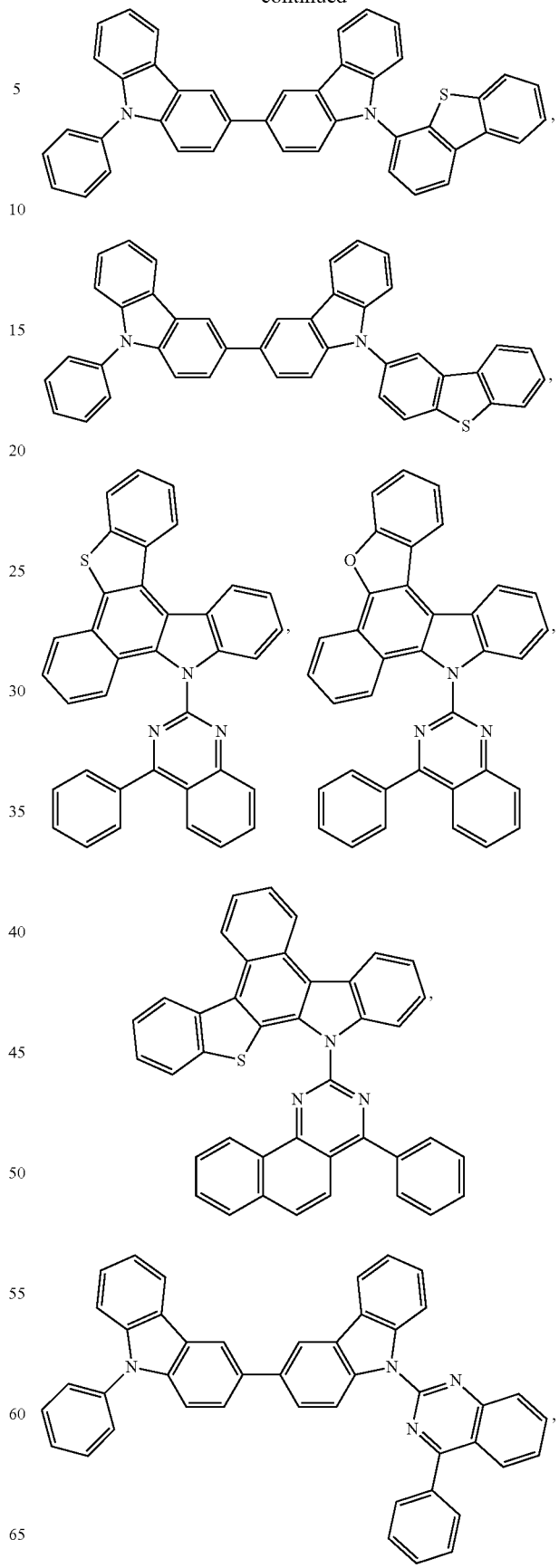

27
-continued
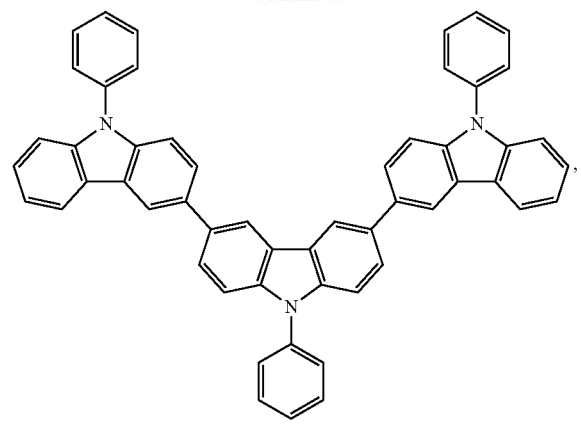
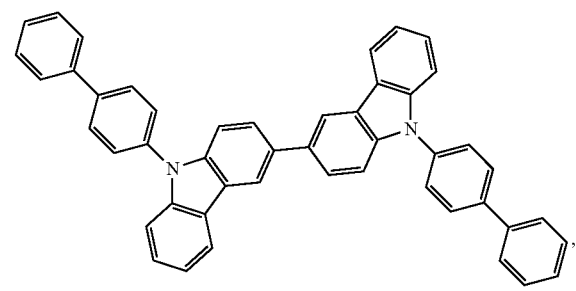
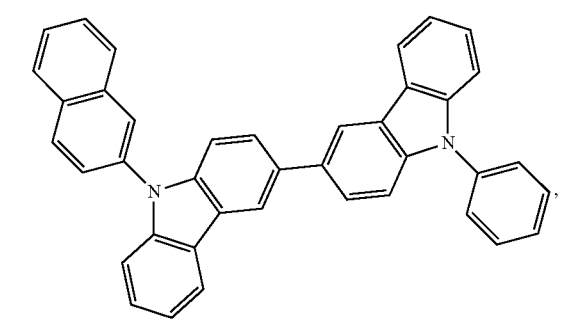
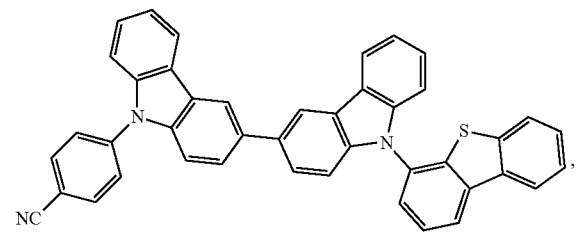
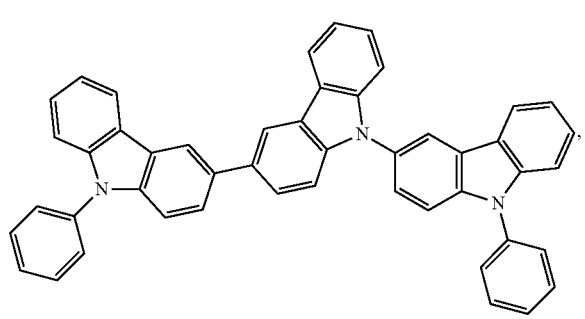
28
-continued
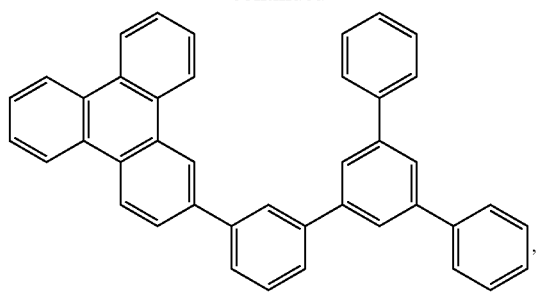
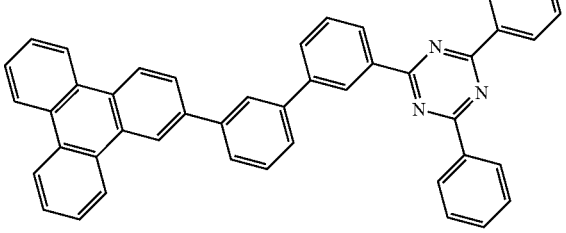
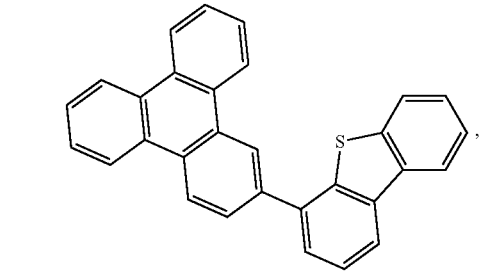
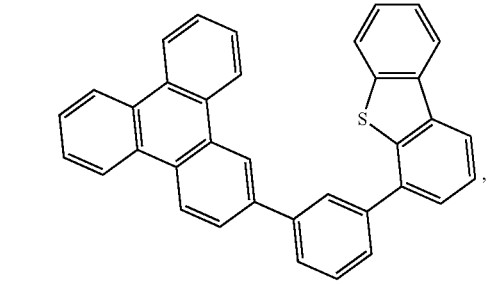
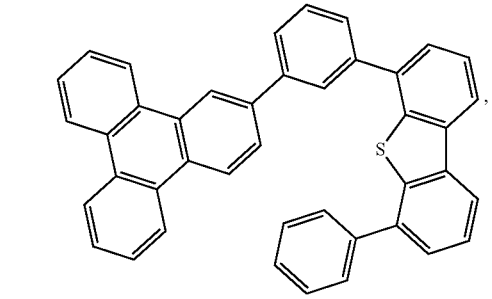
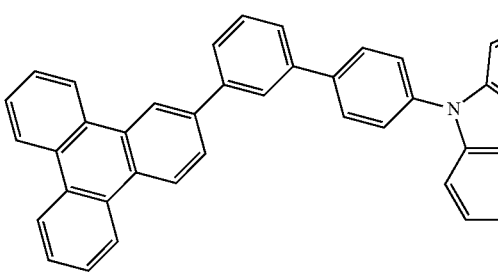

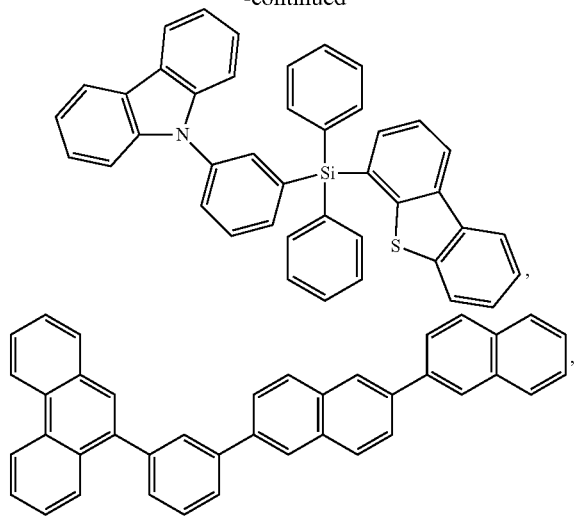

and combinations thereof.

Additional information on possible hosts is provided below.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

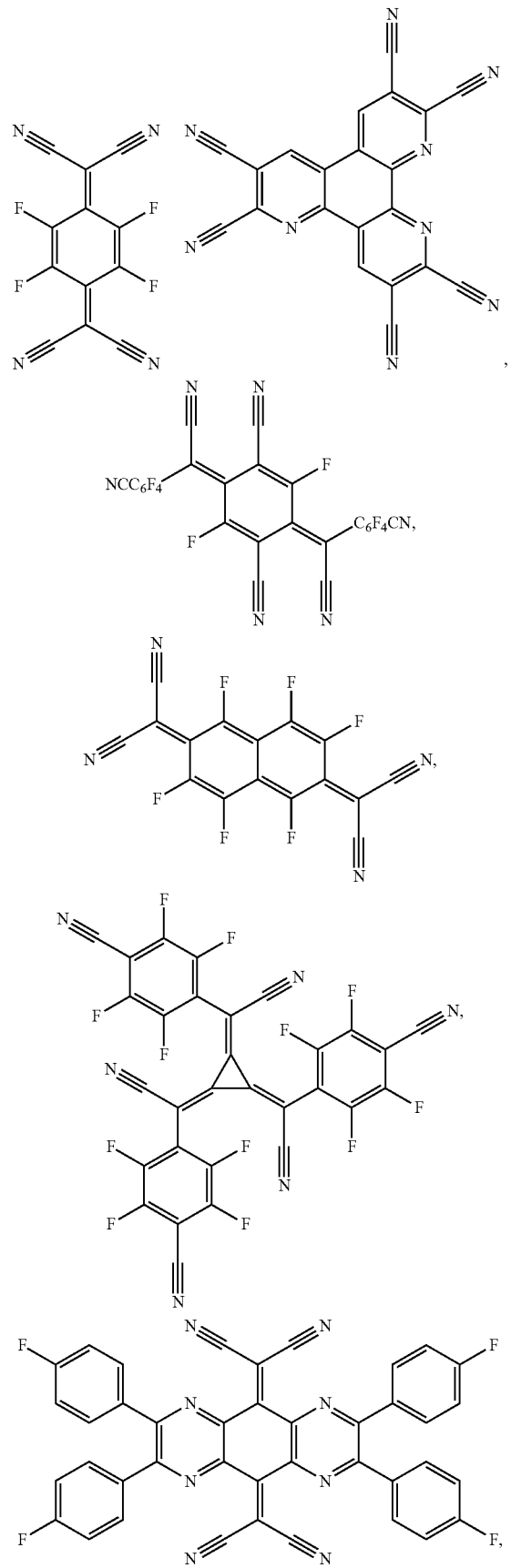

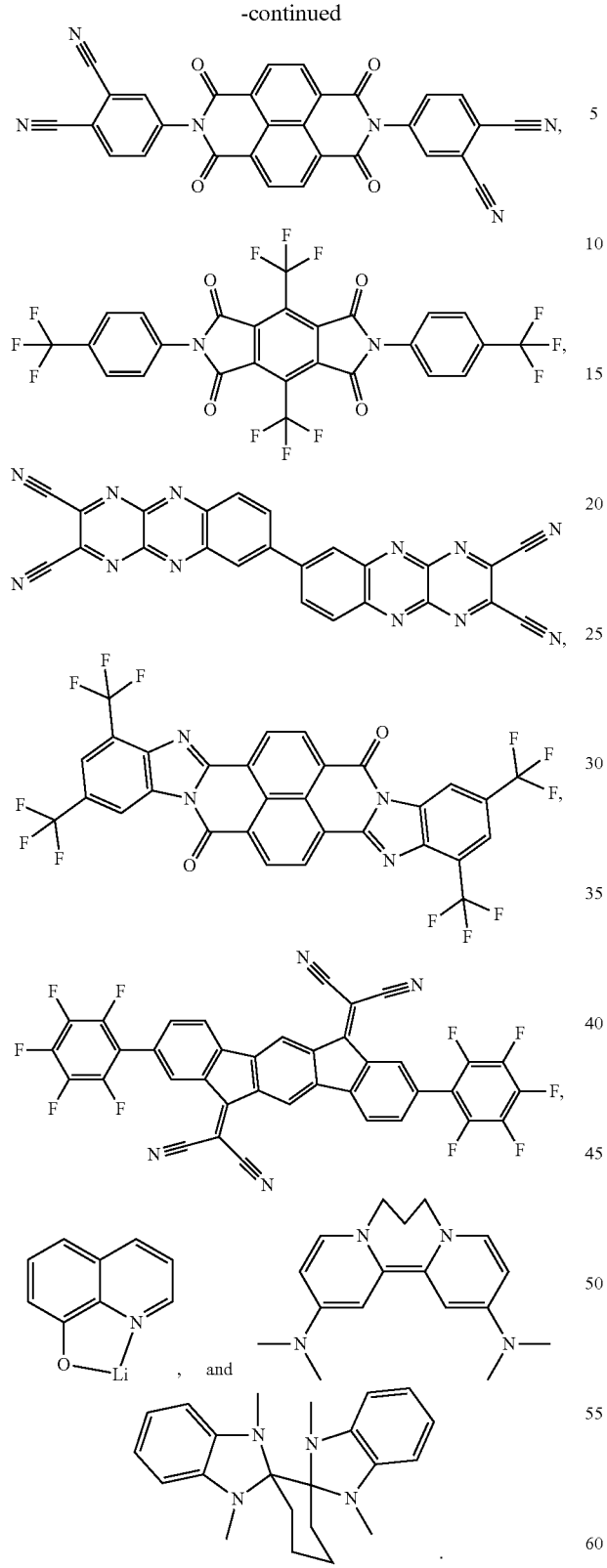

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

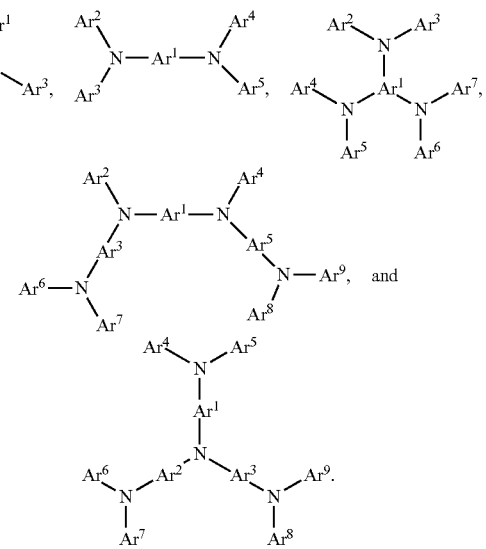

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

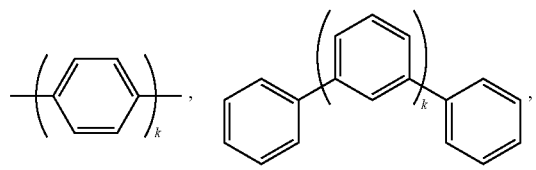

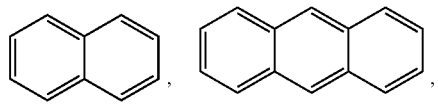

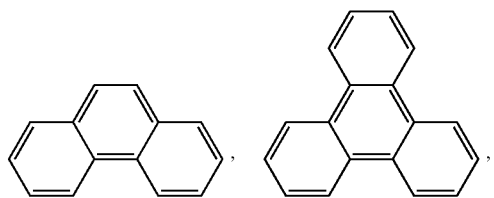

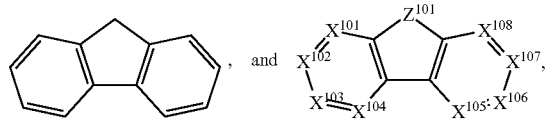

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

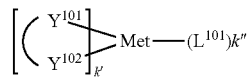

wherein Met is a metal, which can have an atomic weight greater than 40; $(Y^{101}-Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}-Y^{102})$ is a 2-phenylpyridine derivative. In another aspect, $(Y^{101}-Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

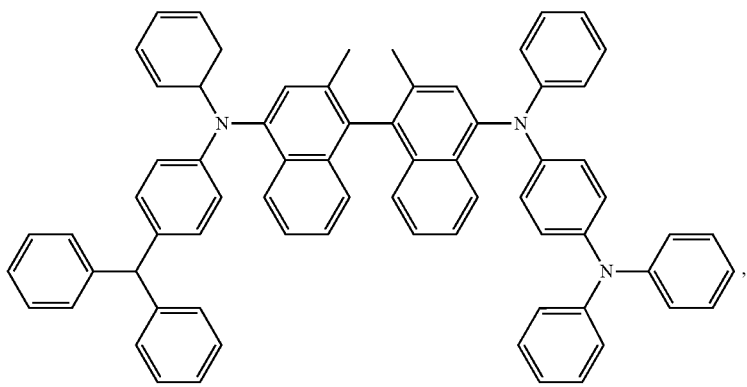

-continued
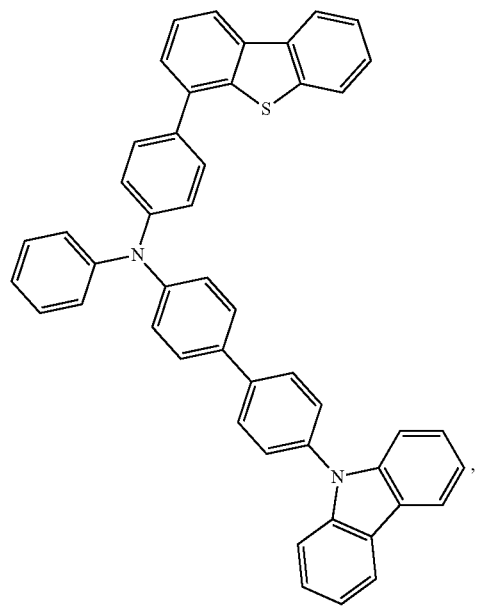
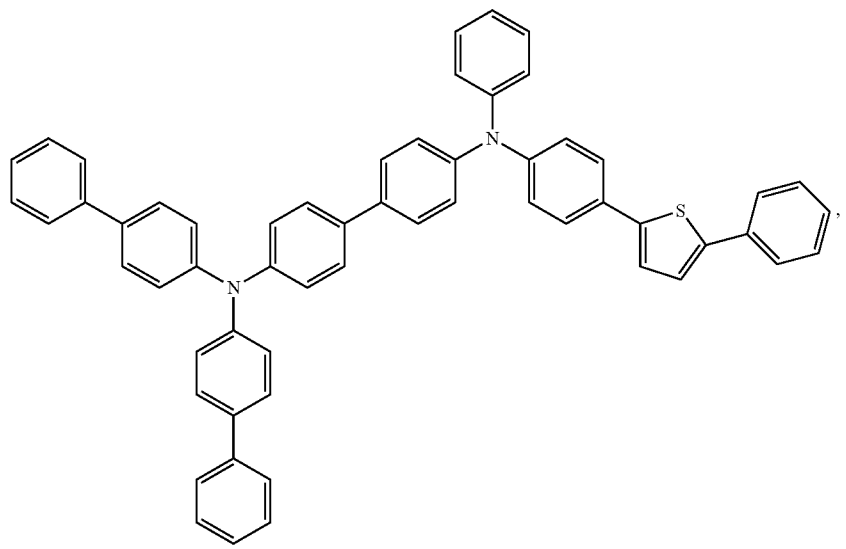
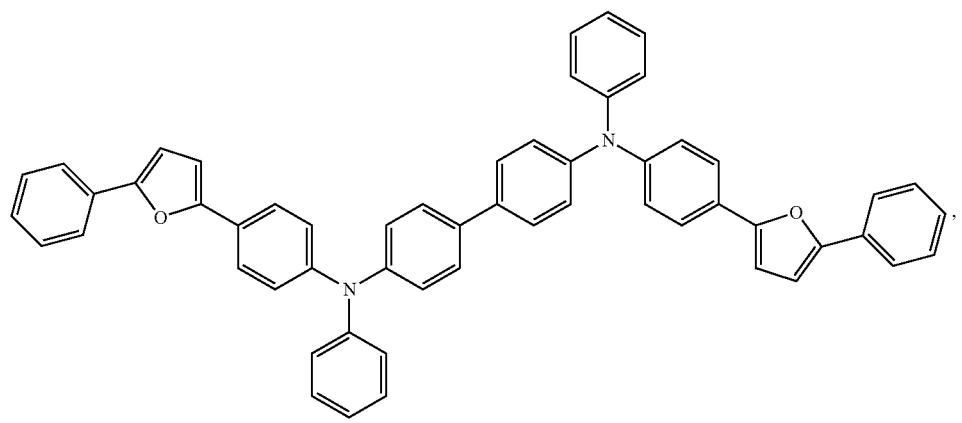

37 38
-continued
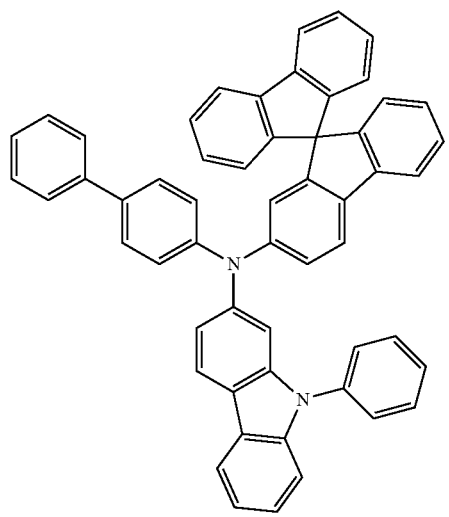
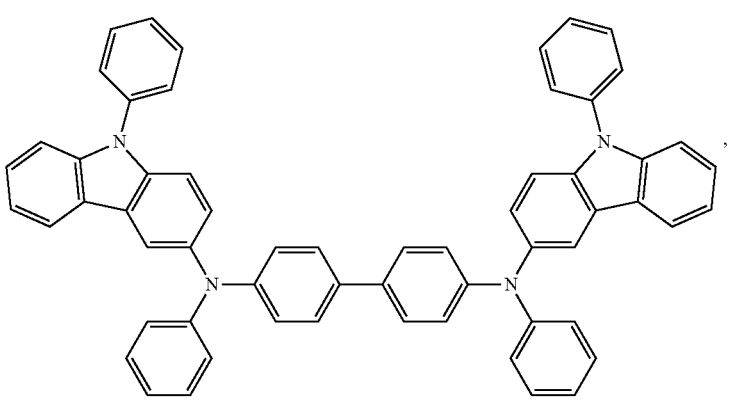
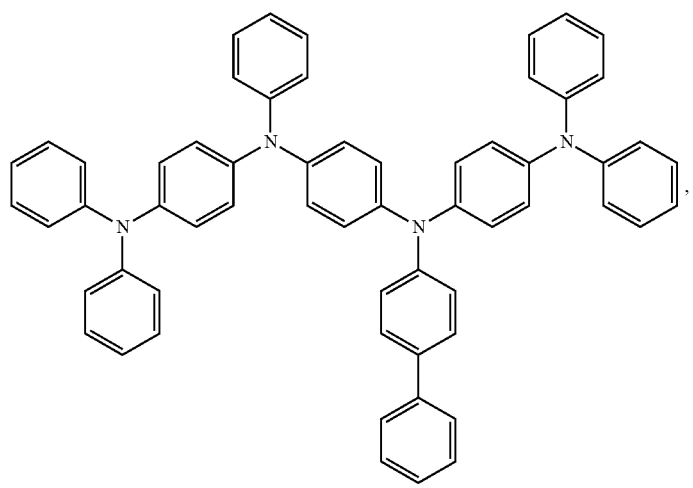
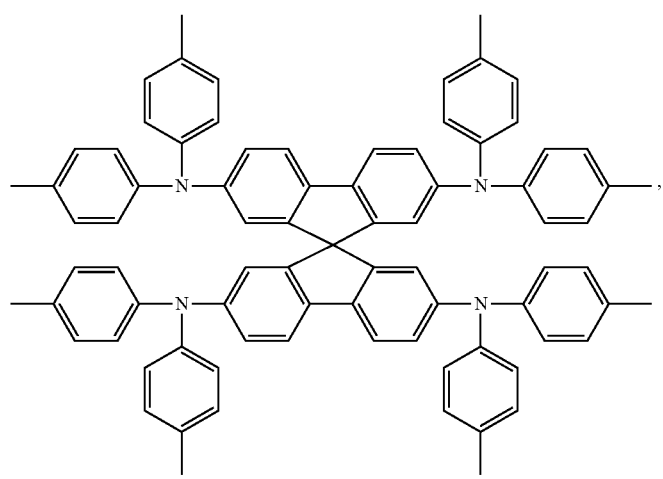

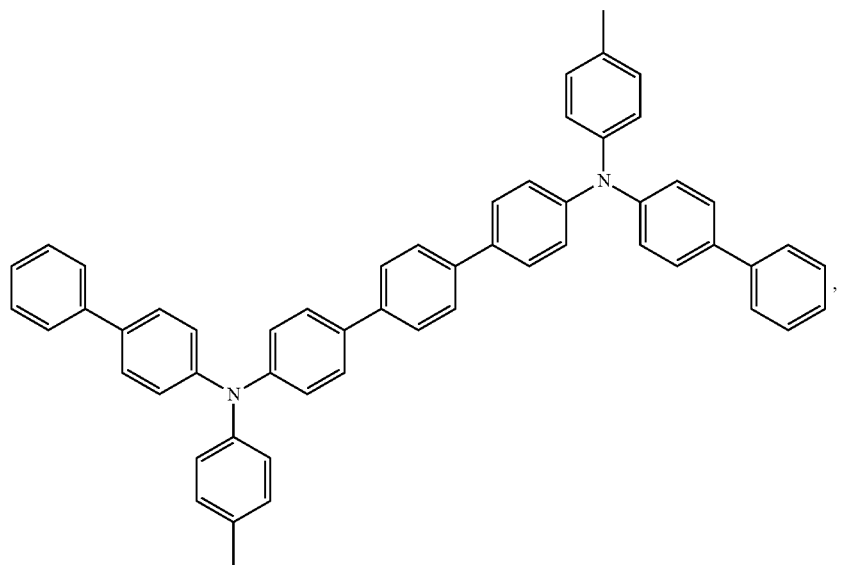
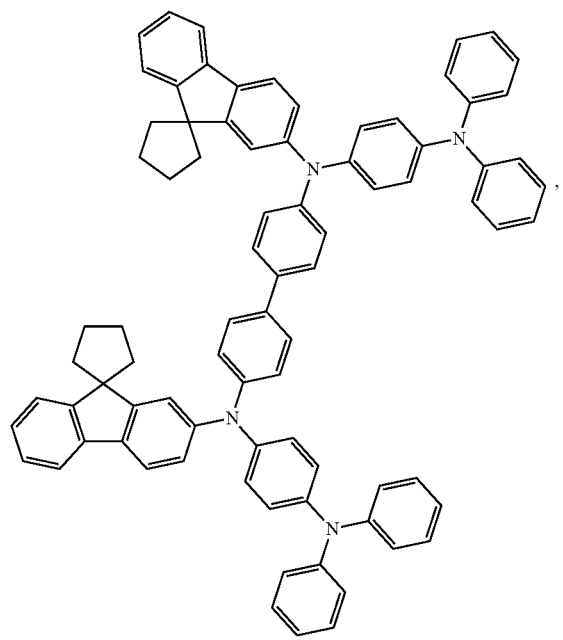
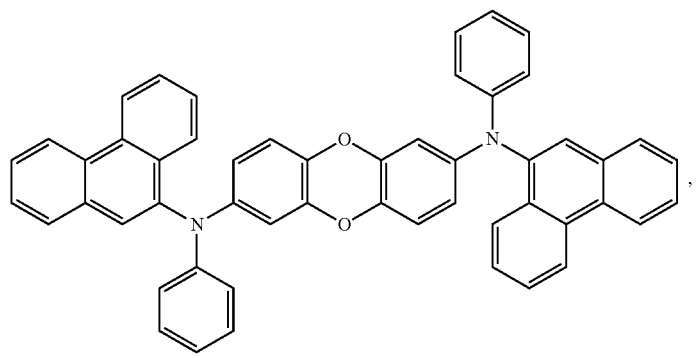

-continued
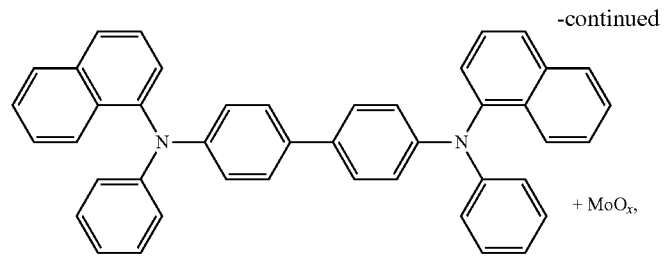
+ MoOx,
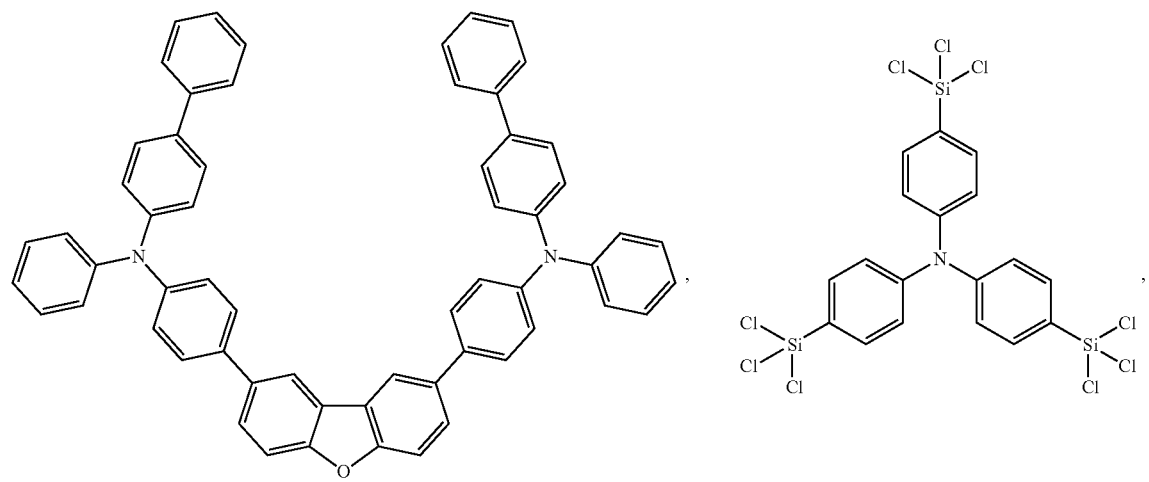
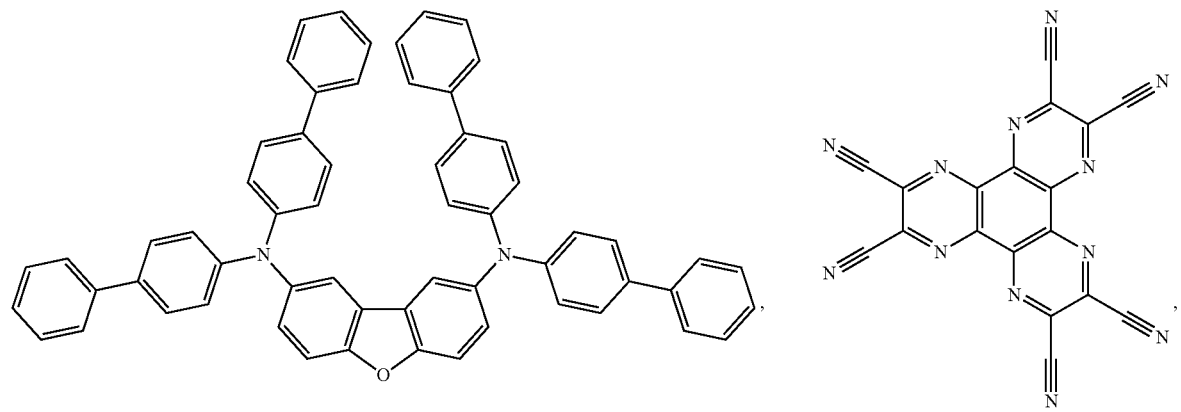
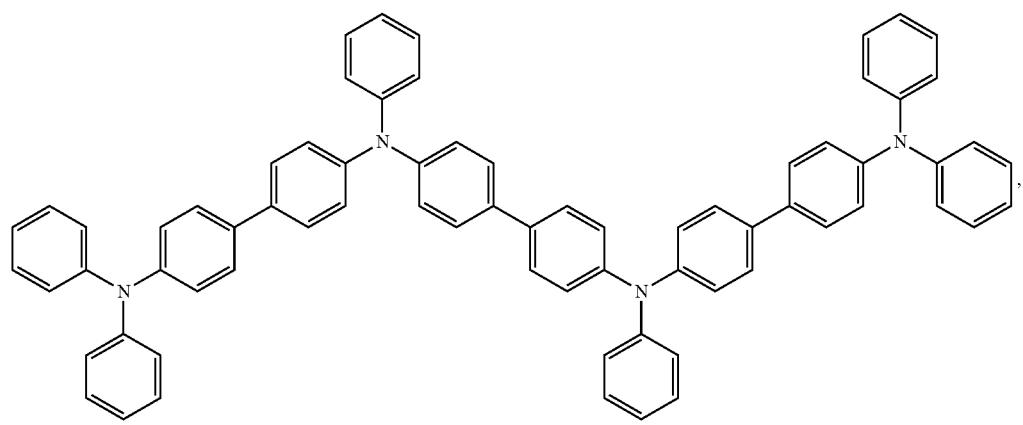

-continued
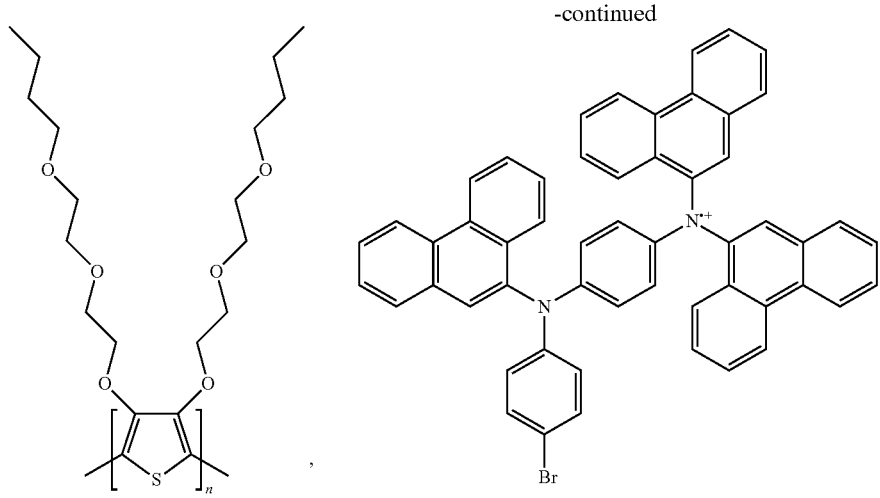
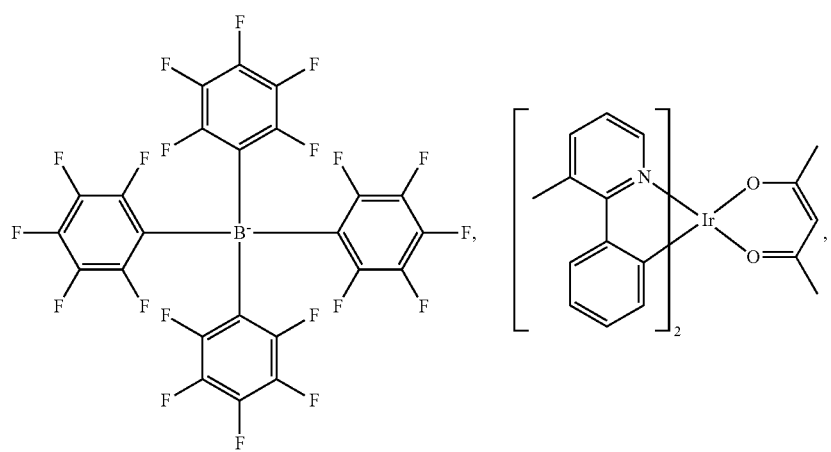
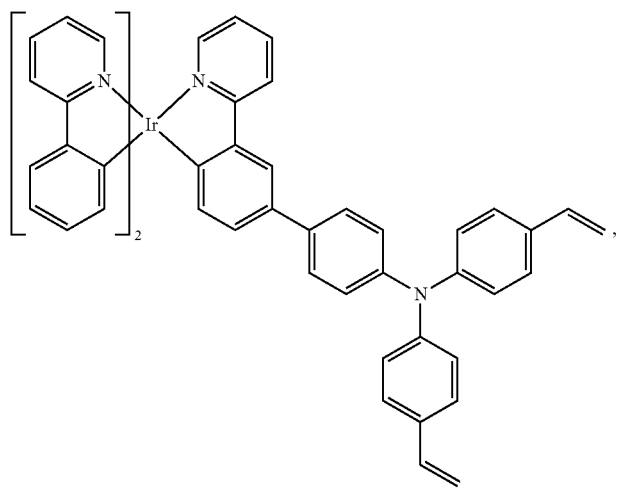

-continued
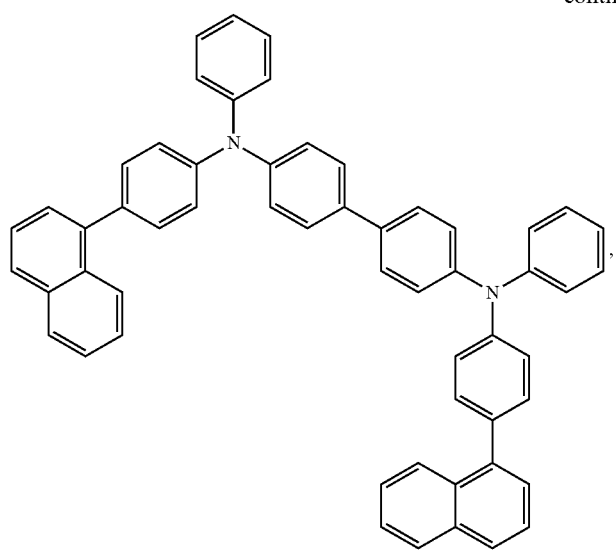
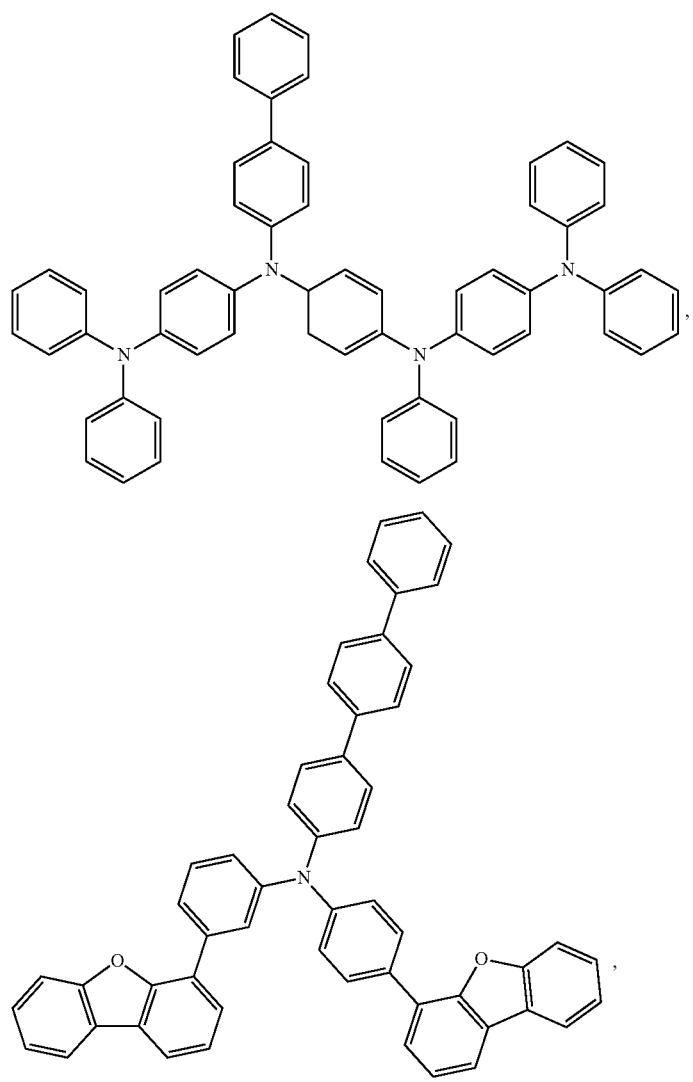

-continued
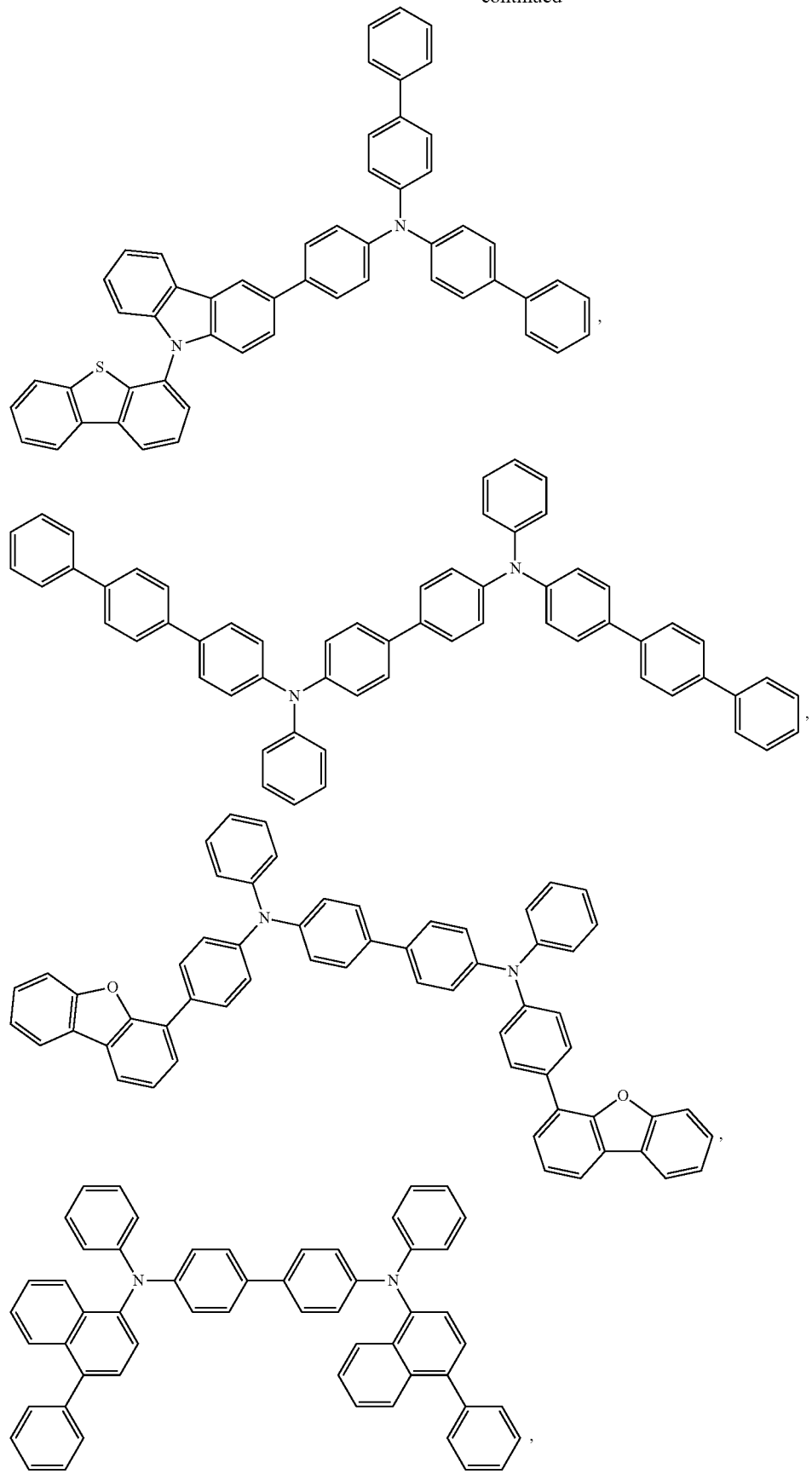

-continued
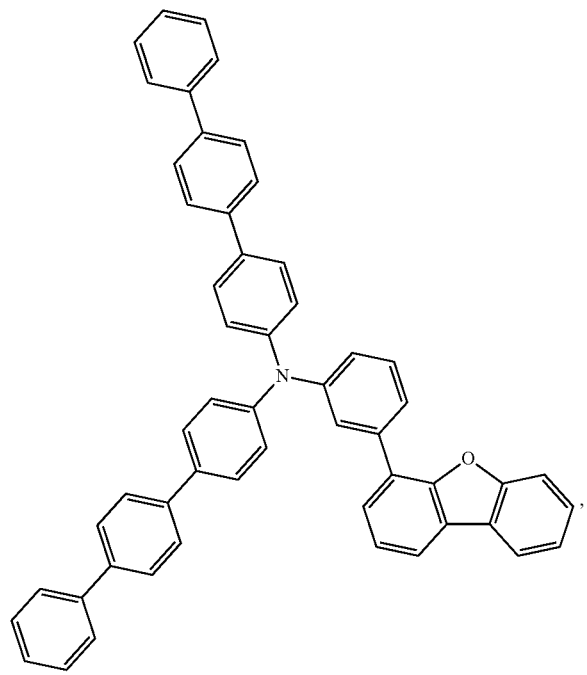
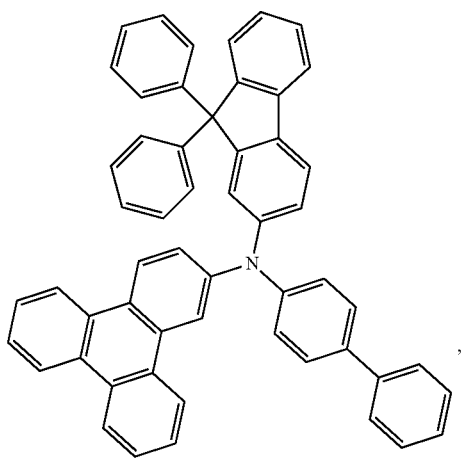
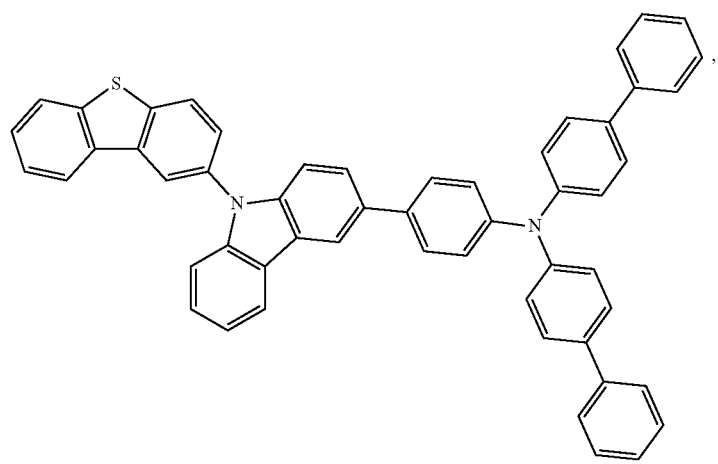
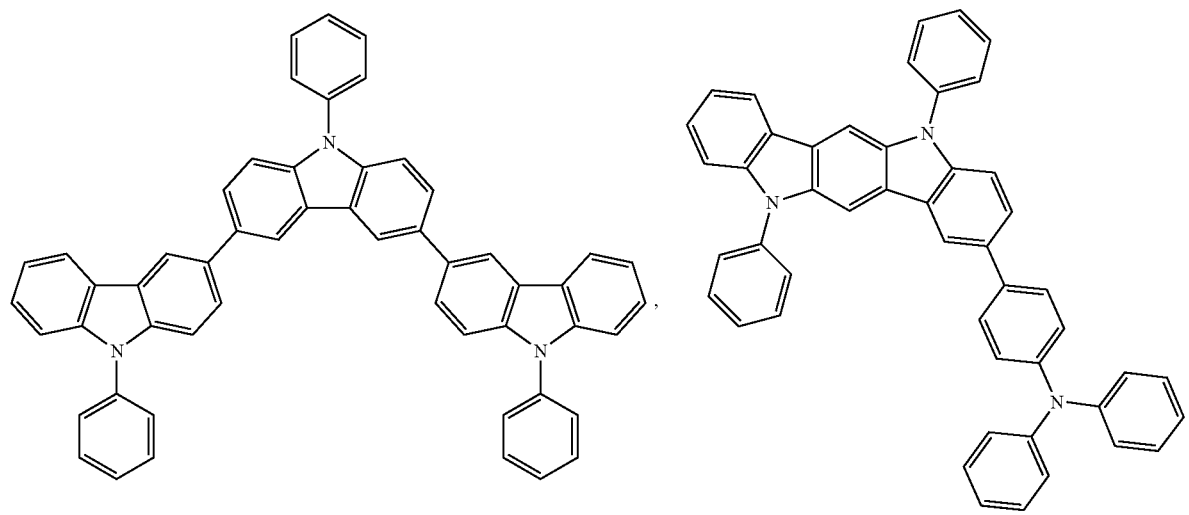

-continued
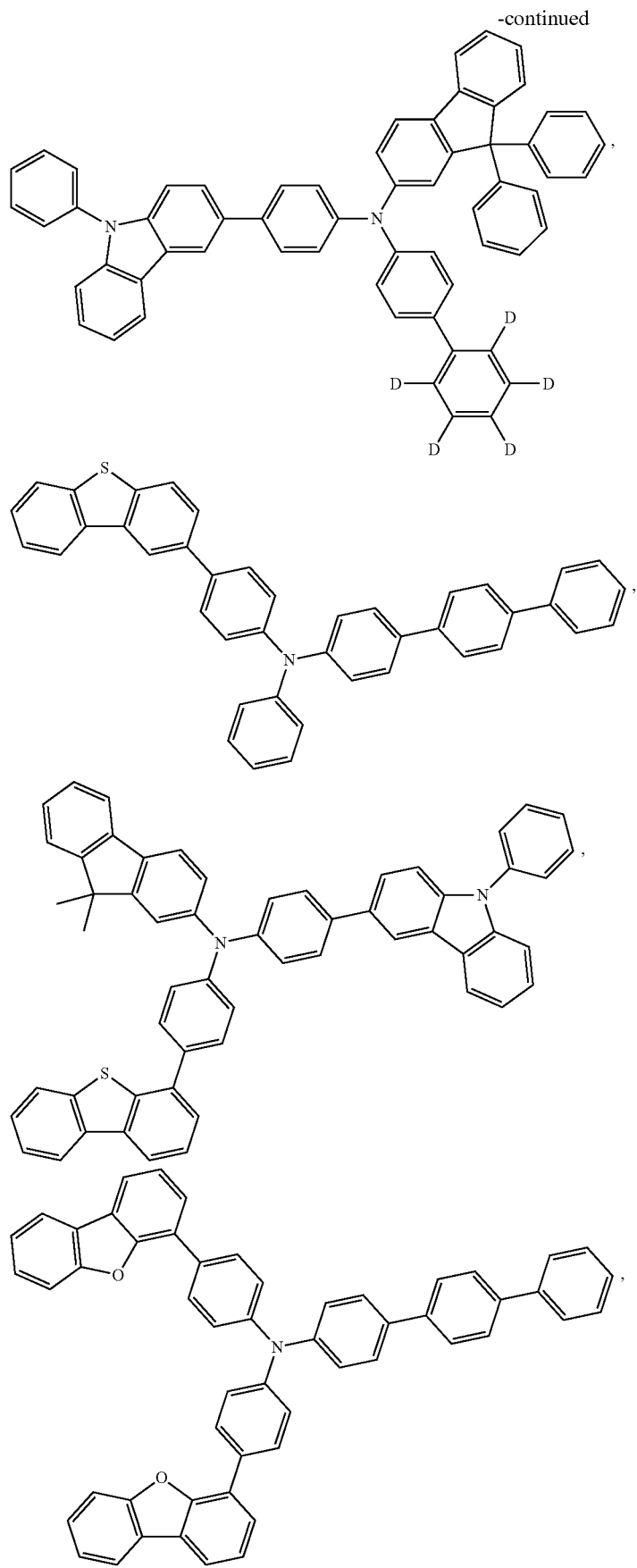

-continued
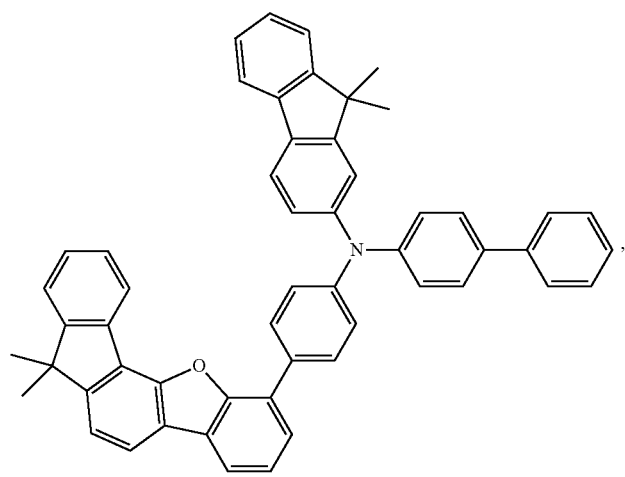
53
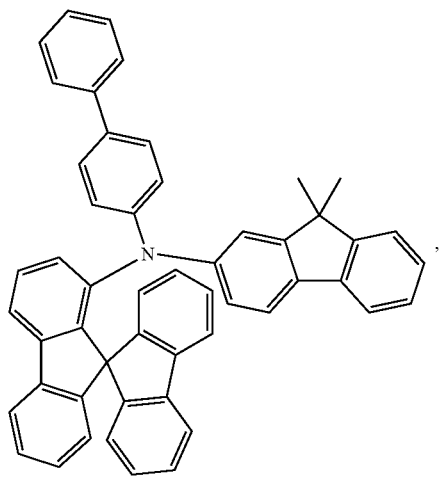
54
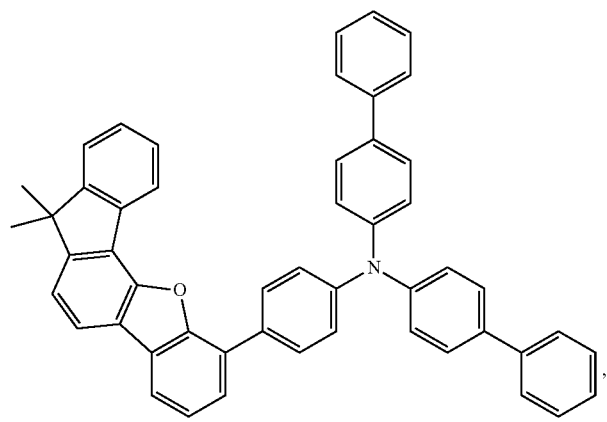
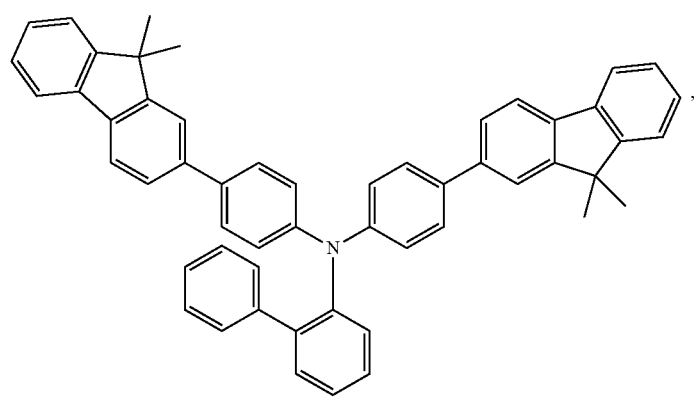

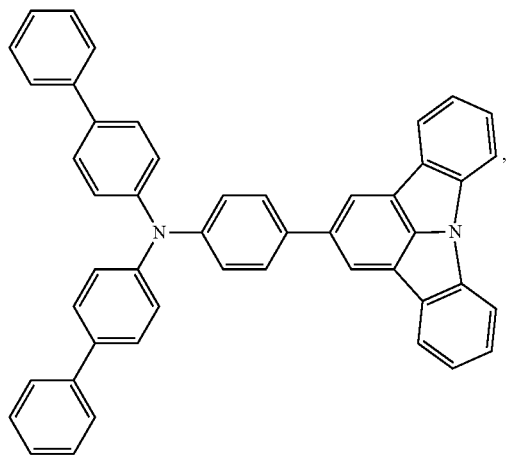
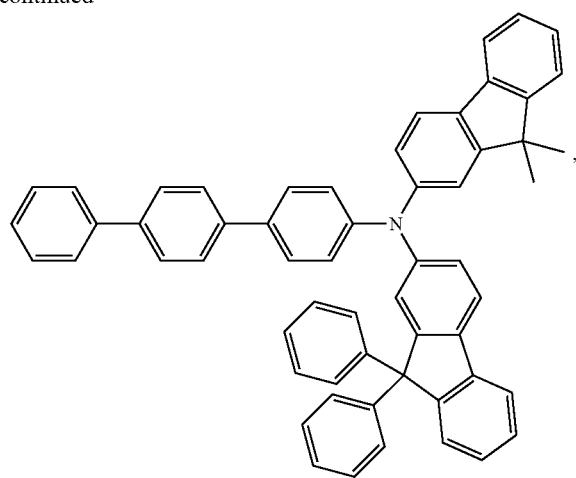
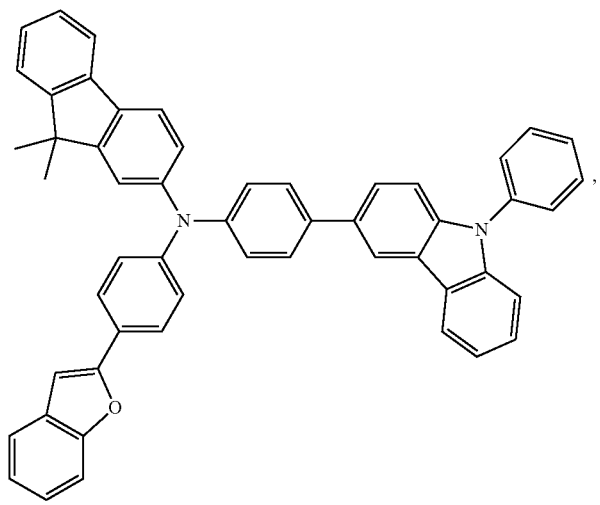
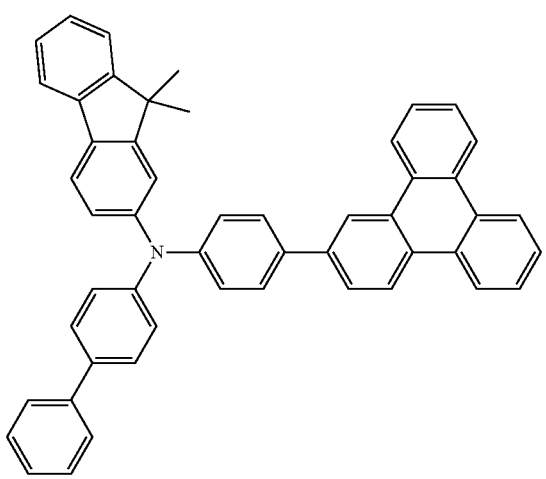
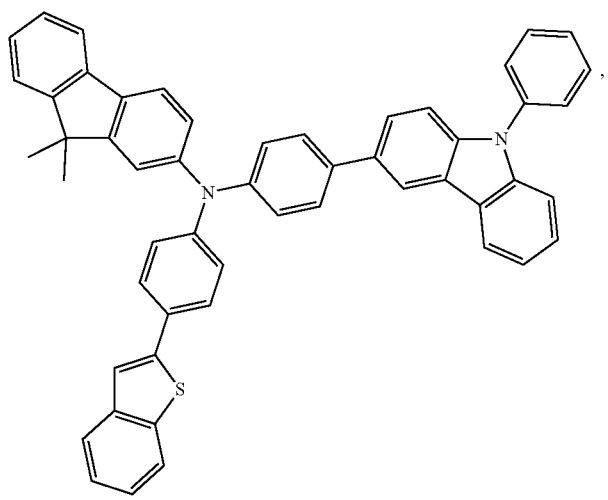

-continued
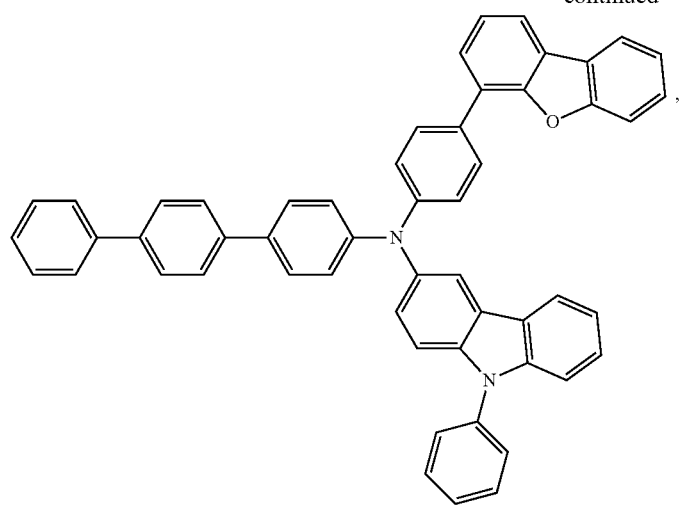
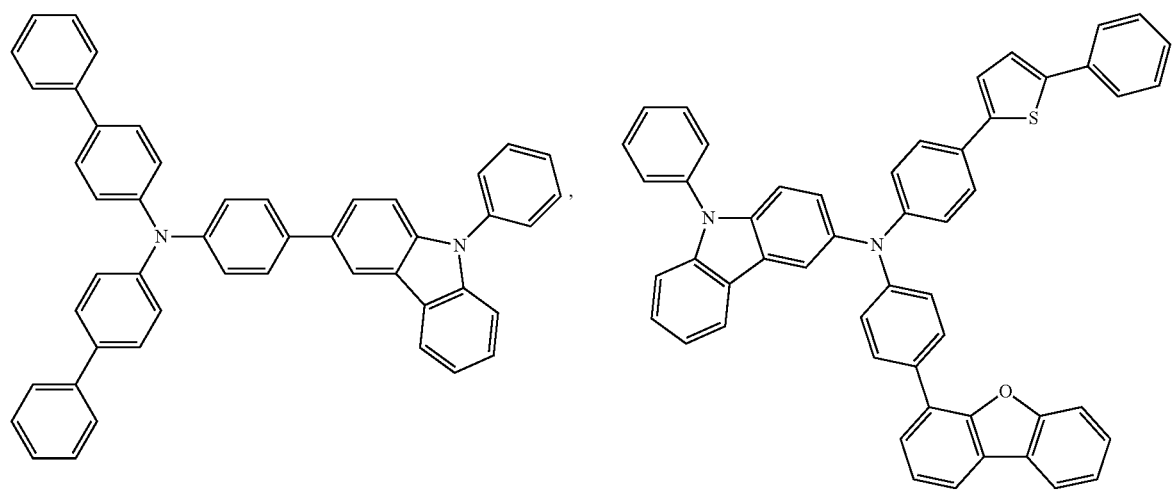
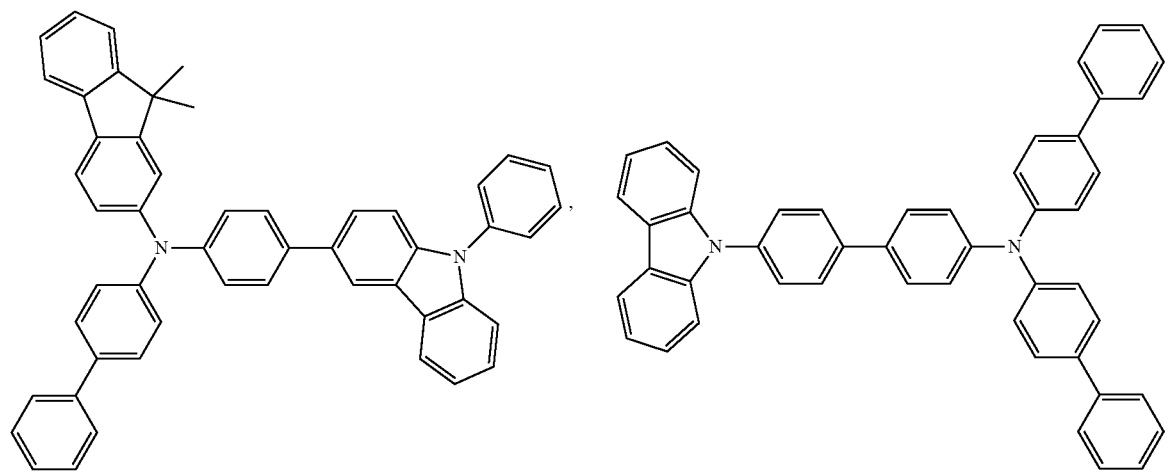

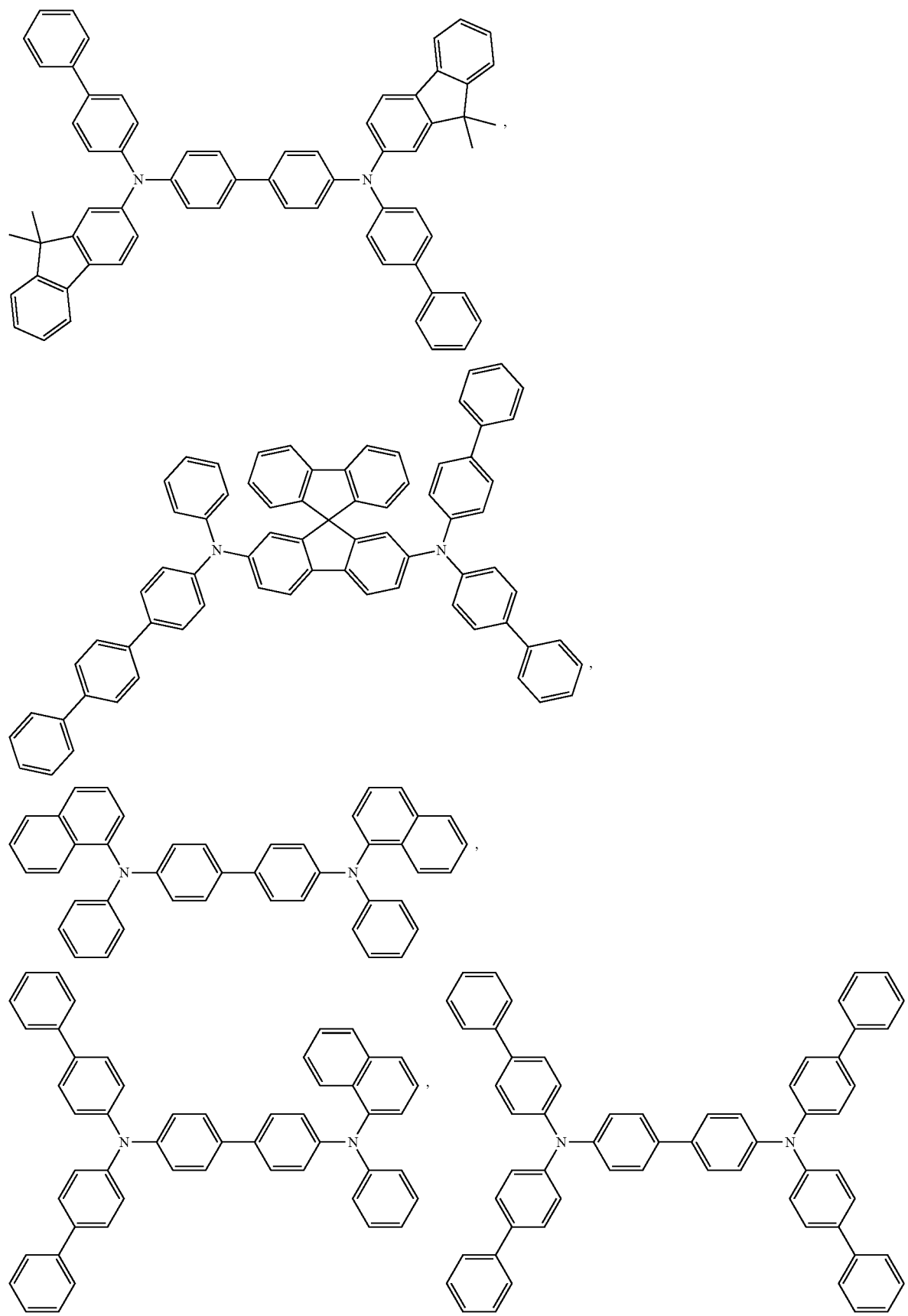

-continued
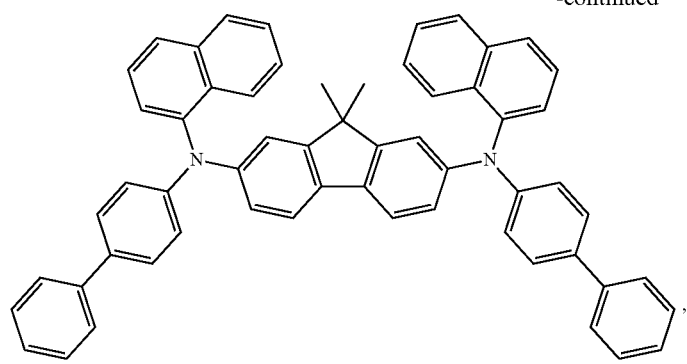
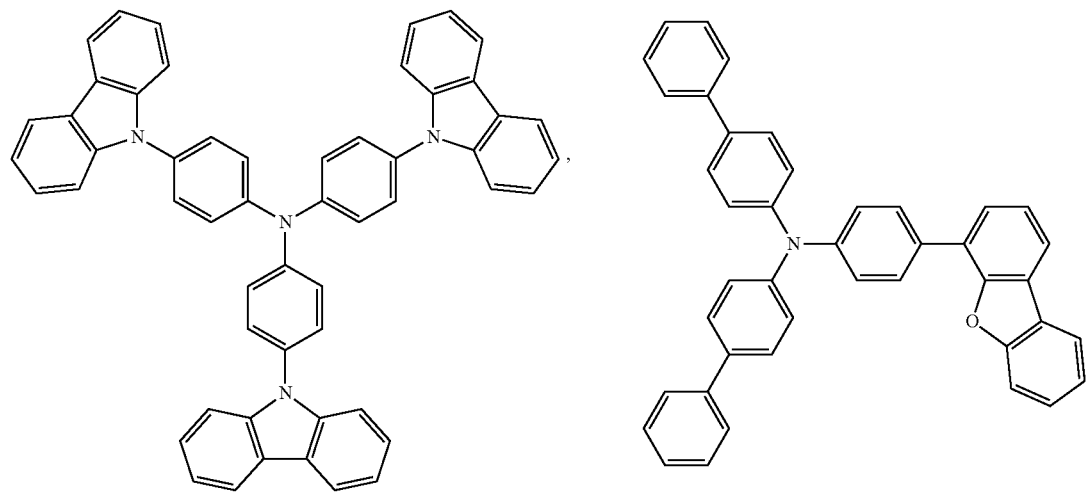
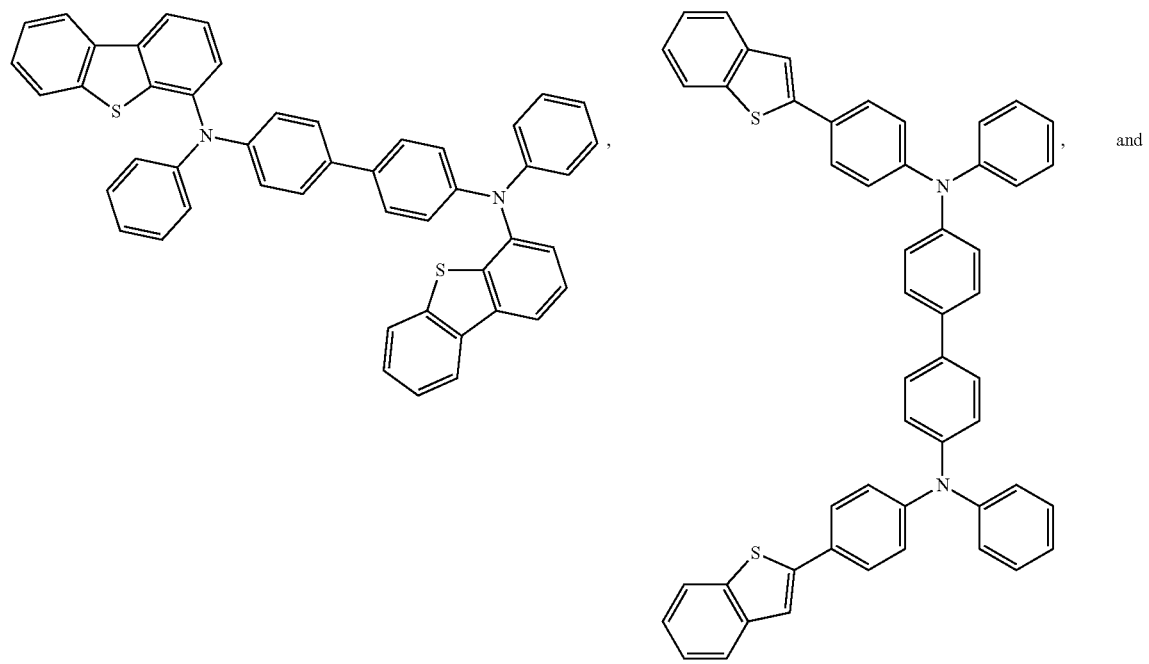

-continued

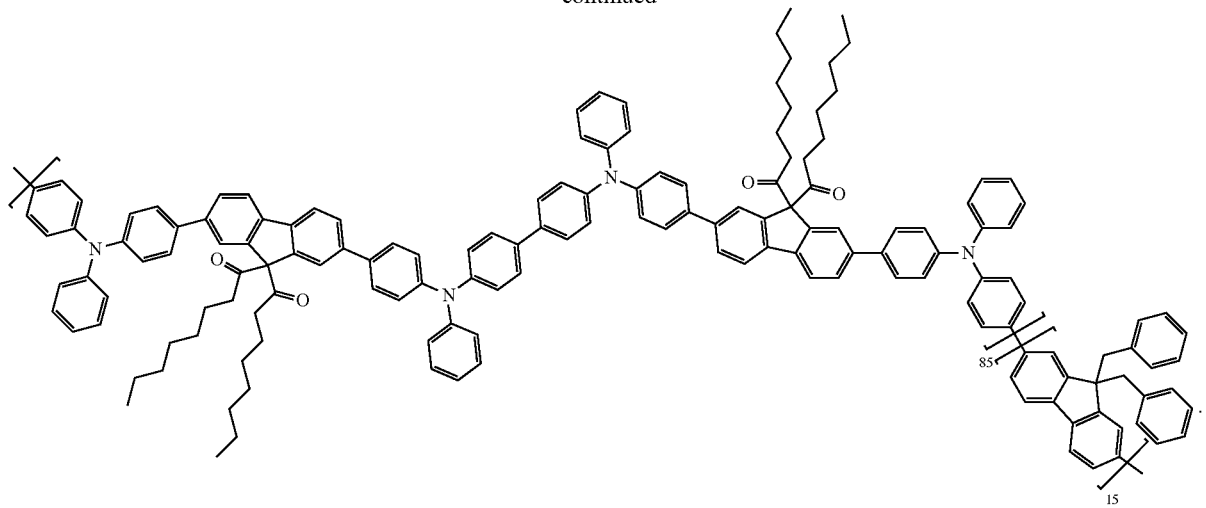

EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

Host:

The light emitting layer of the organic $E_L$ device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

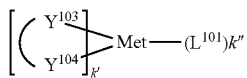

wherein Met is a metal; $(Y^{103}-Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

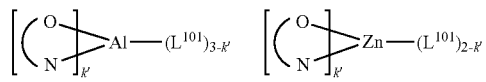

wherein (O—N) is a bidentate ligand, having metal coordinated to atoms O and N.

In another aspect, Met is selected from Ir and Pt. In a further aspect, $(Y^{103}-Y^{104})$ is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

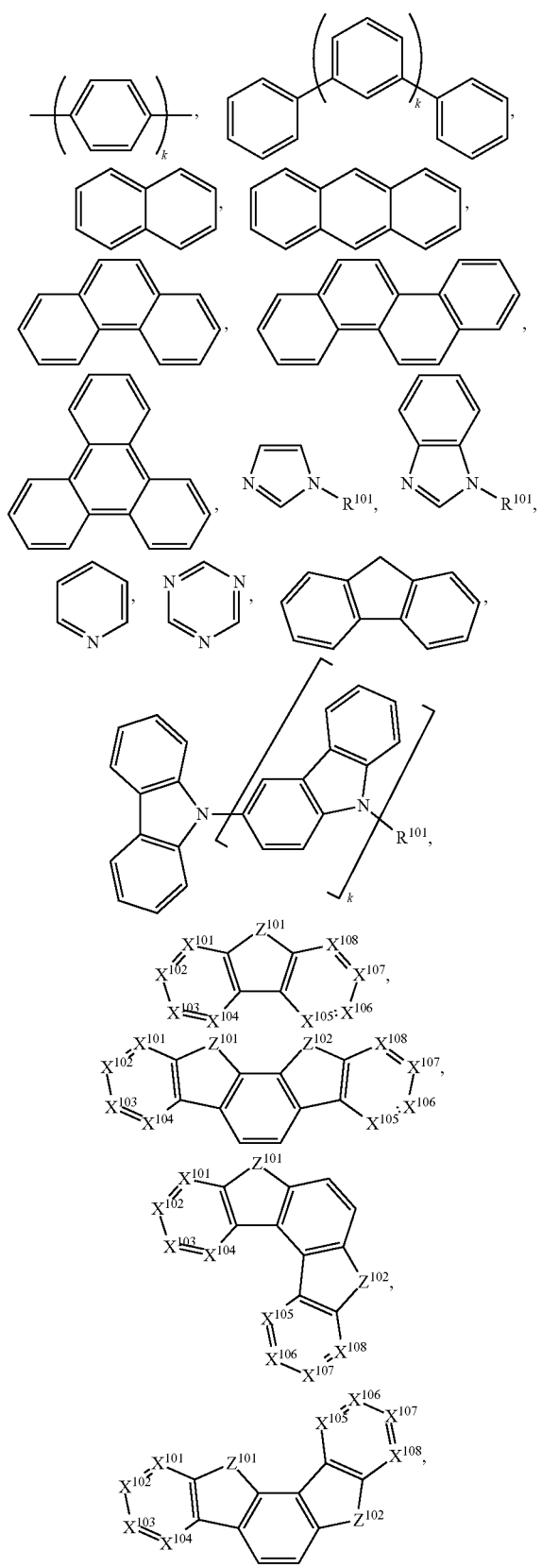

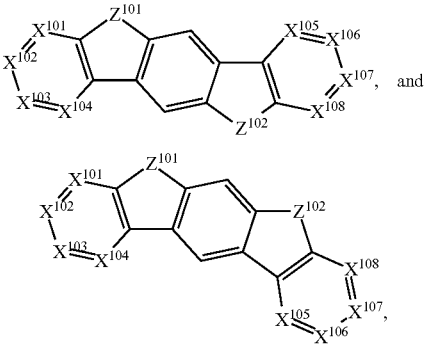

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $R^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,

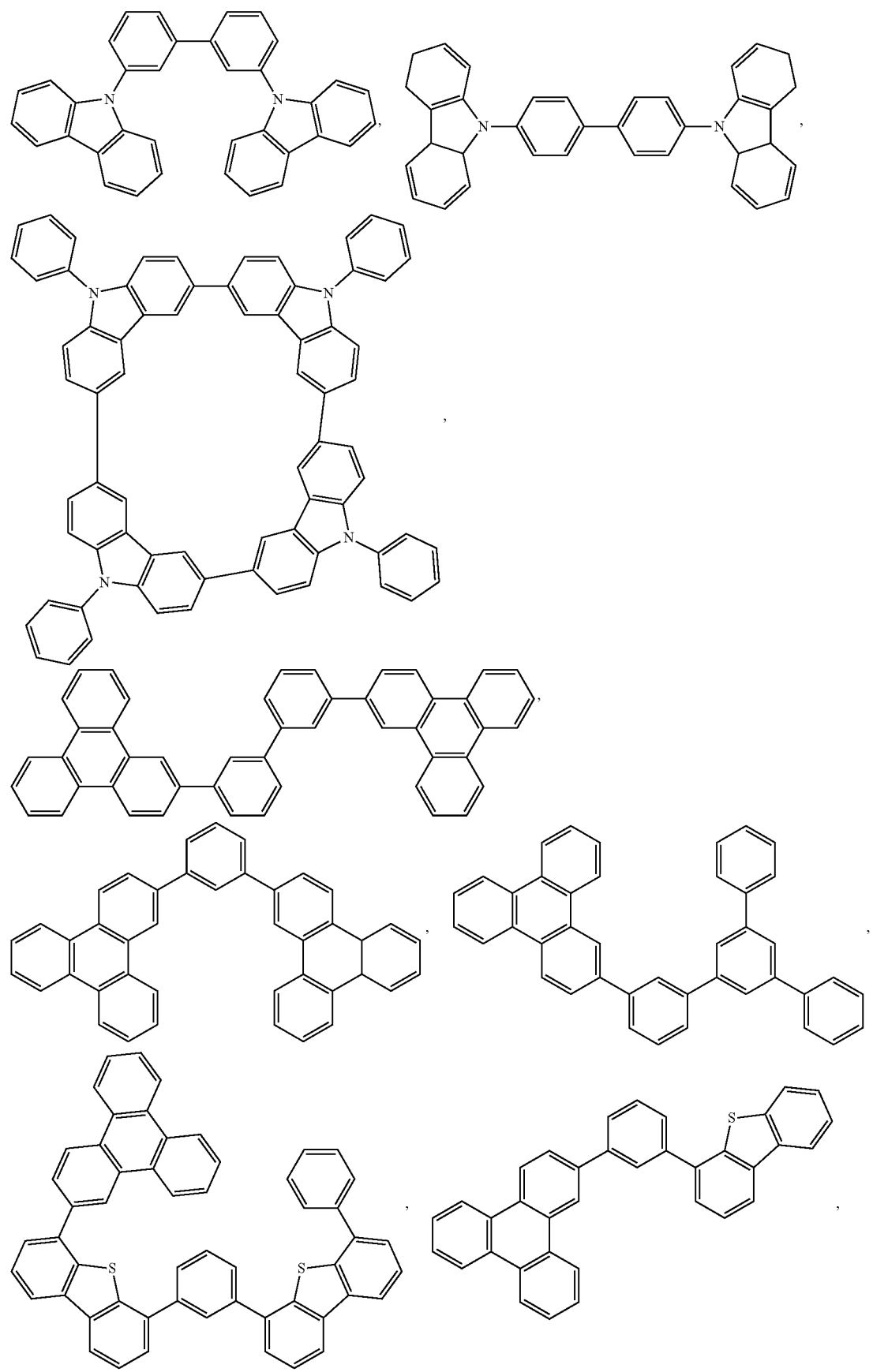

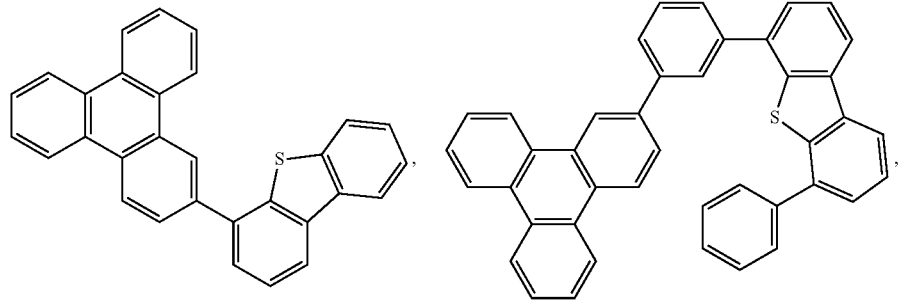
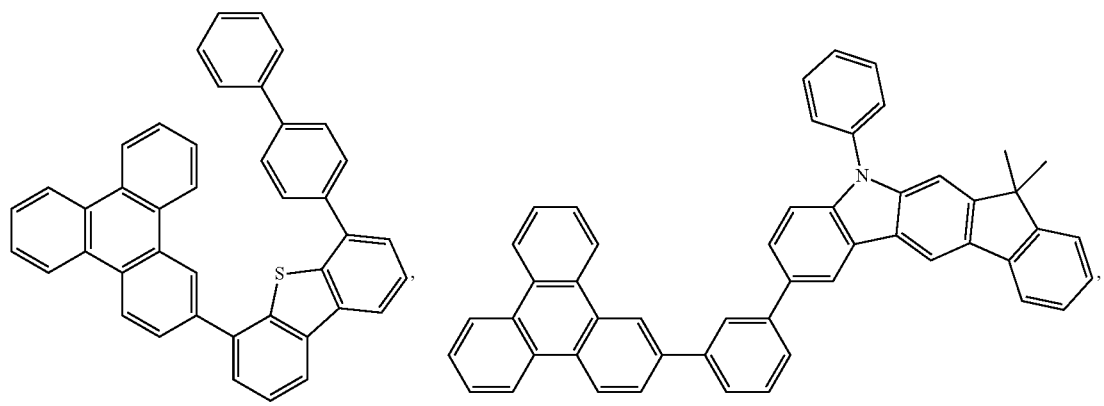
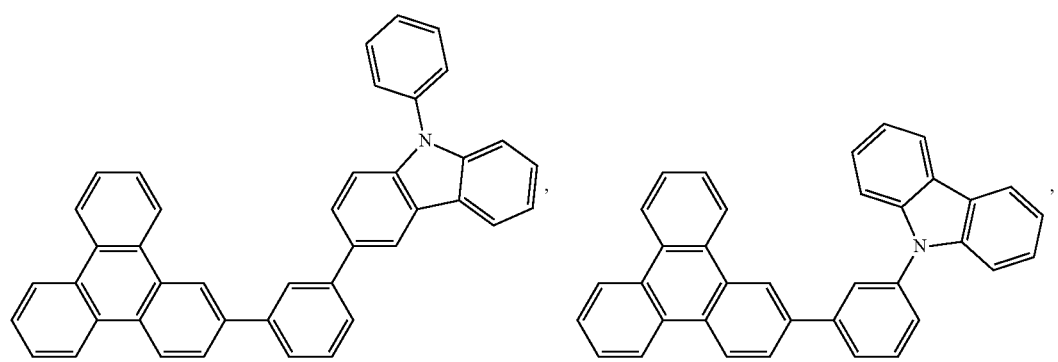
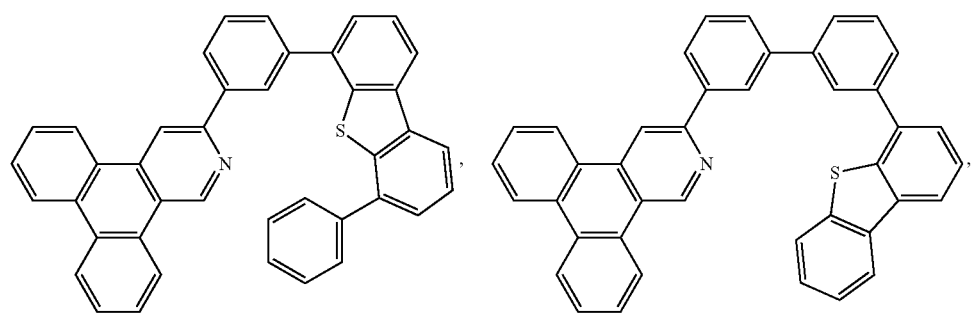
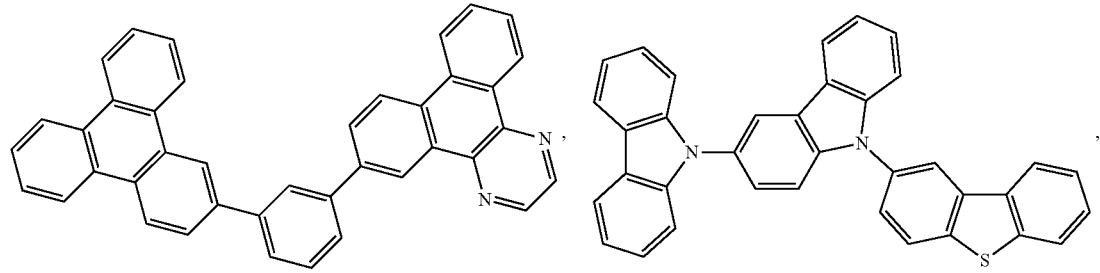

-continued
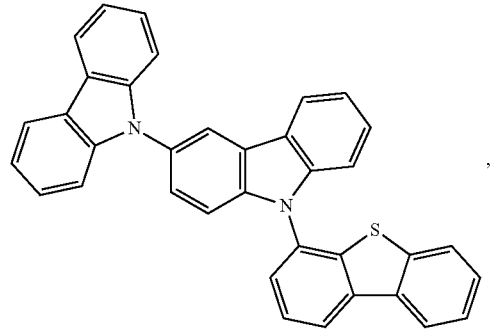
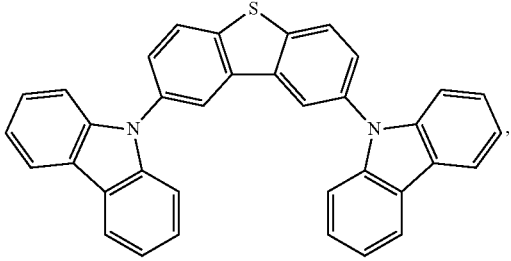
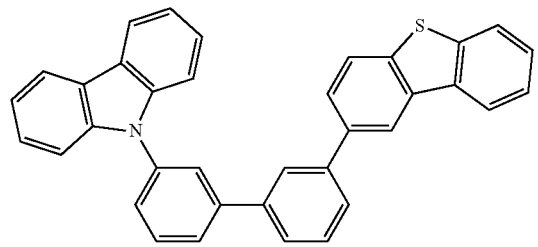
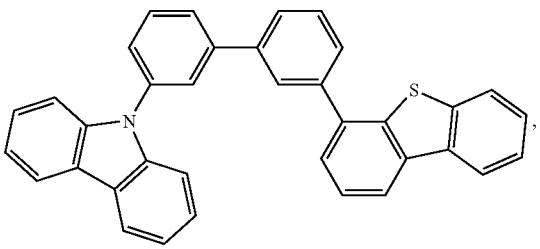
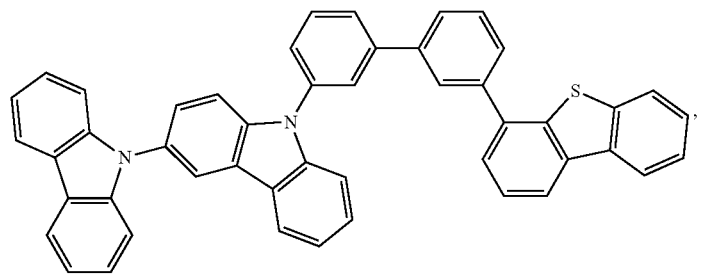
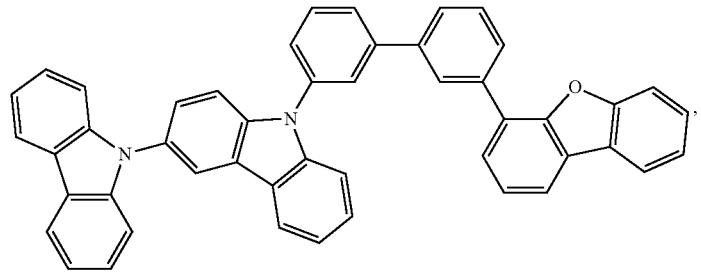
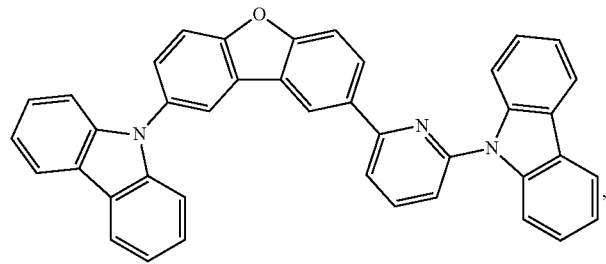
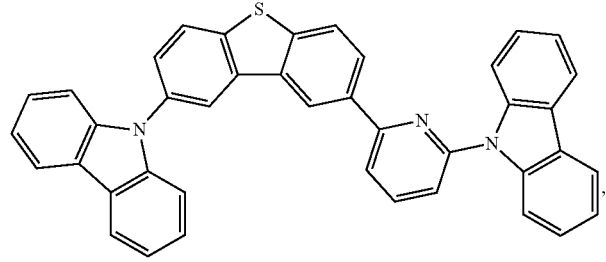

-continued
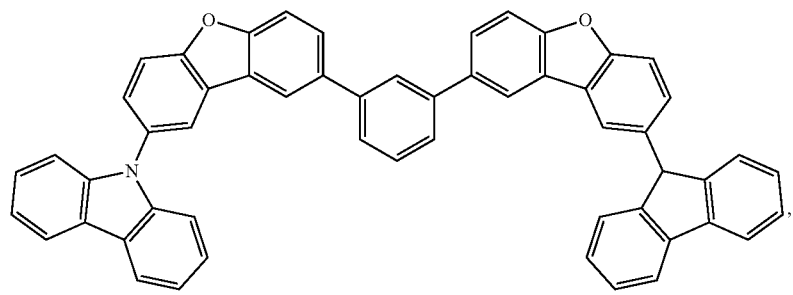
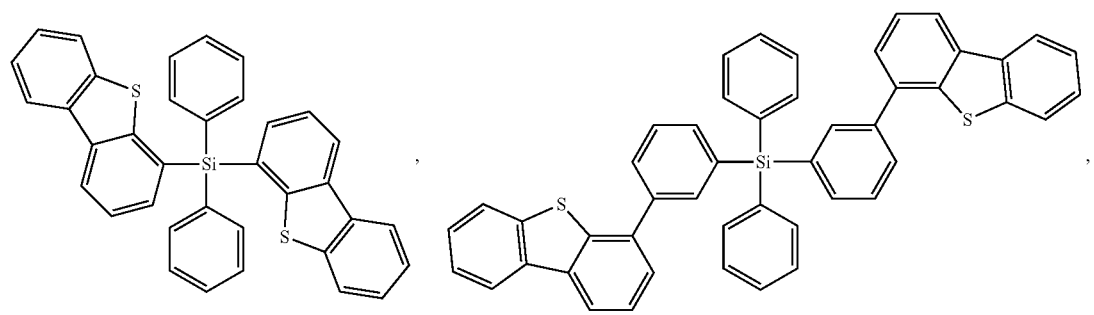
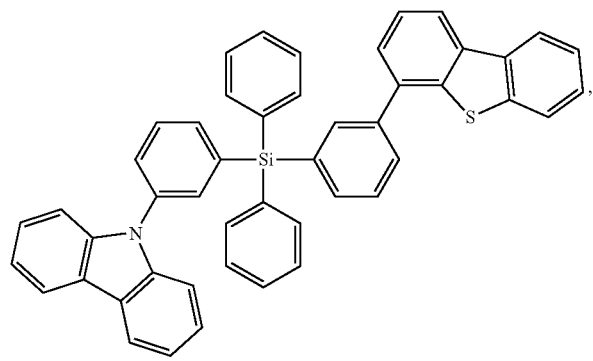
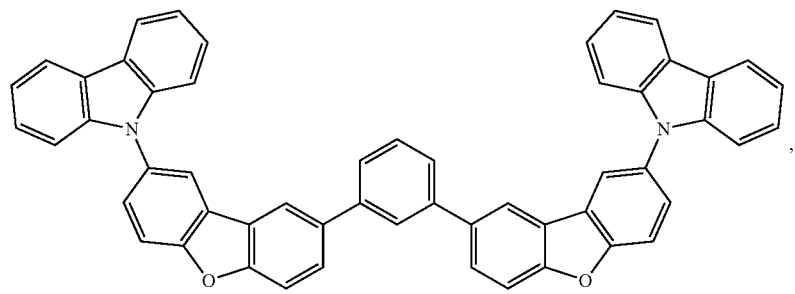
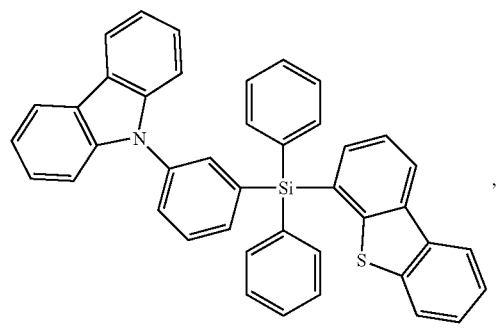

-continued
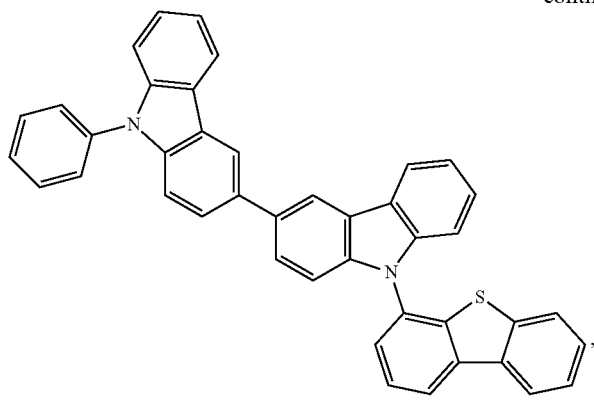
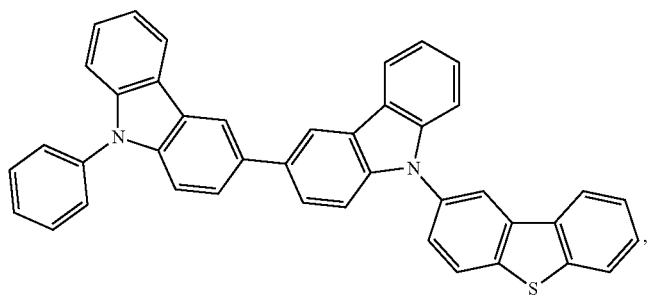
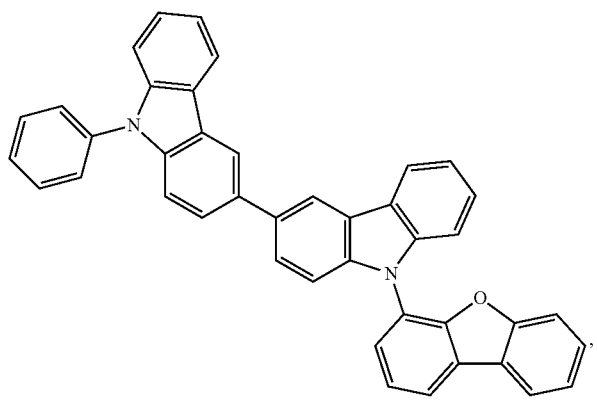
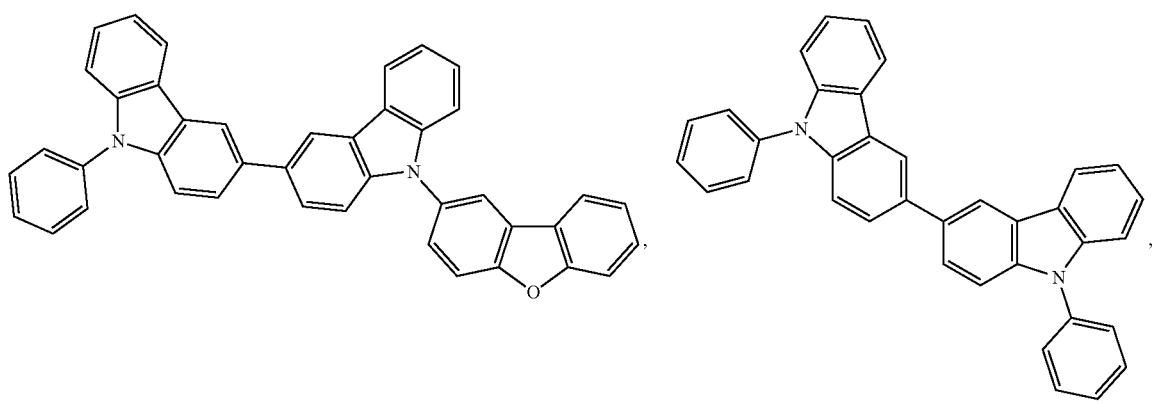

-continued
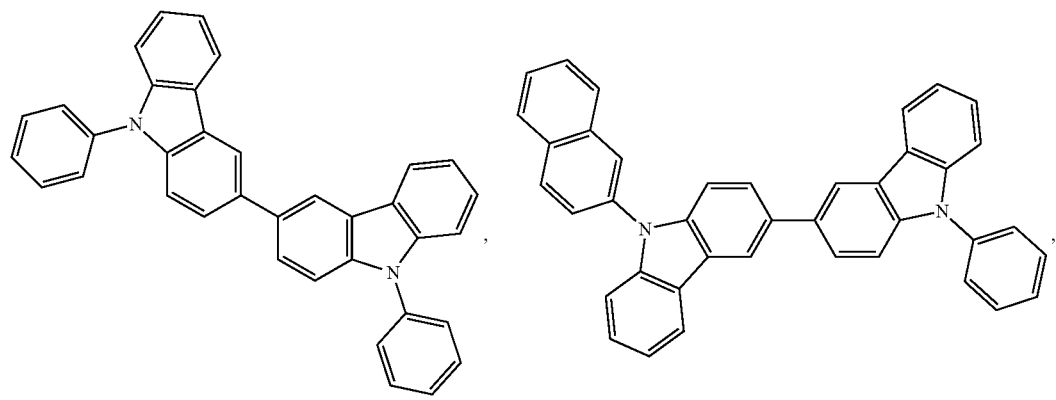
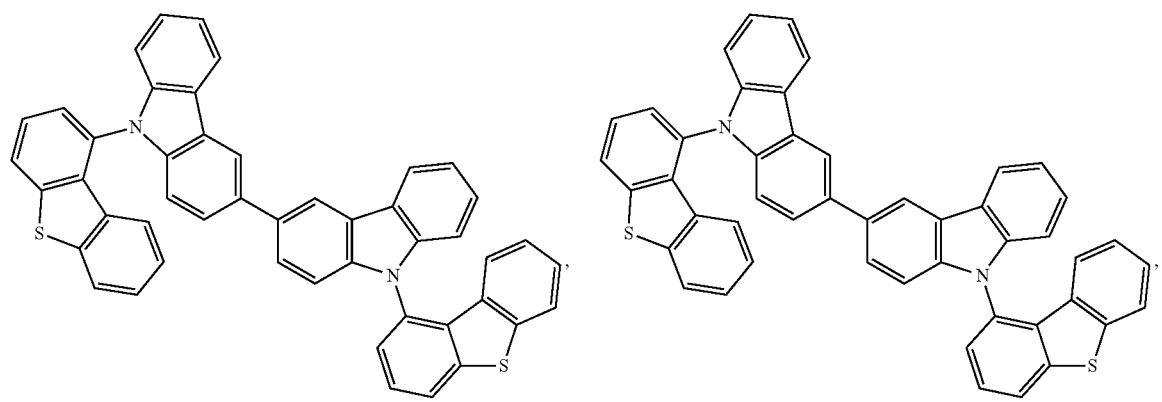
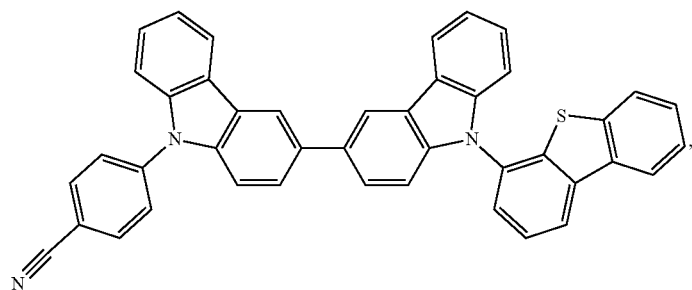
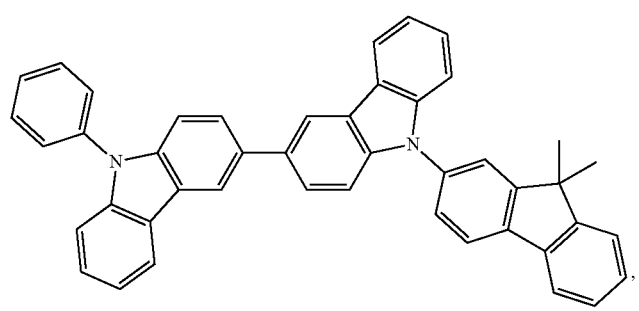

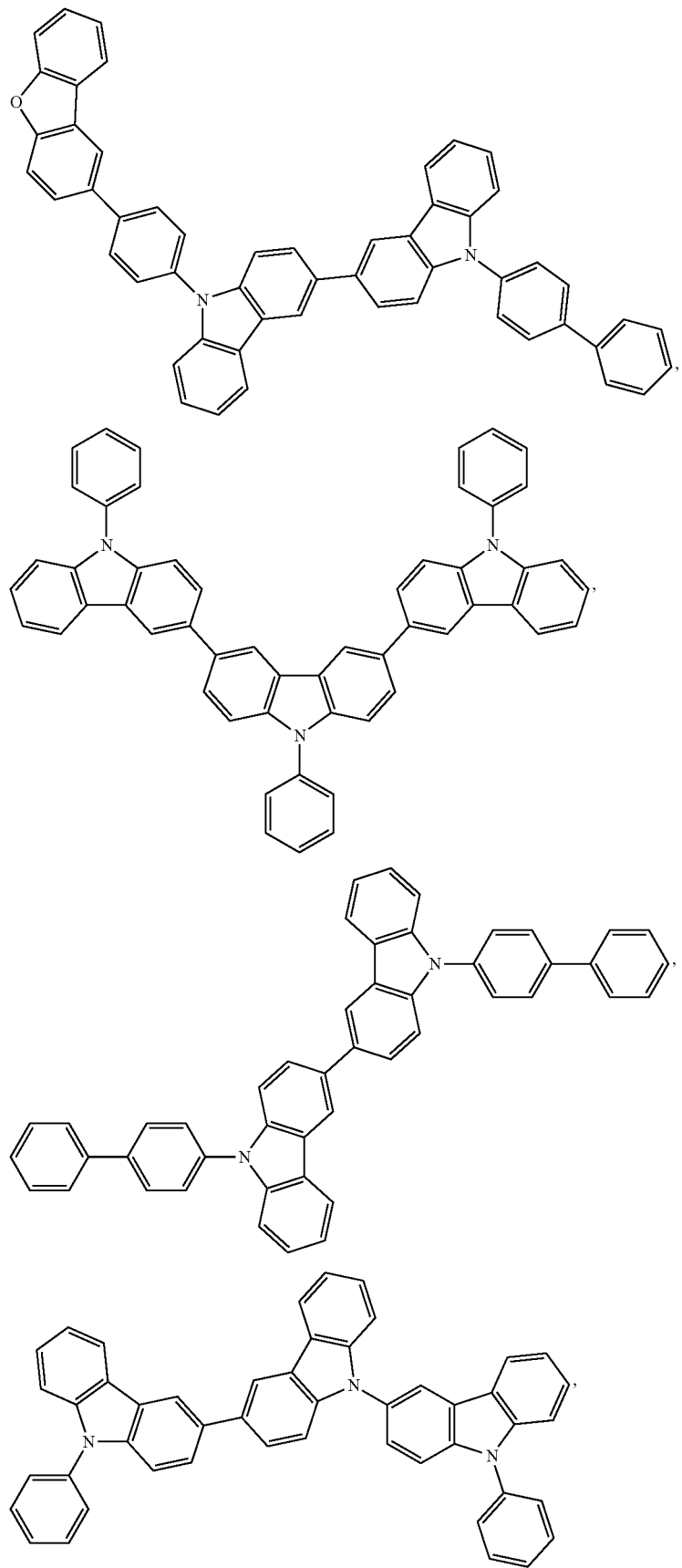

-continued
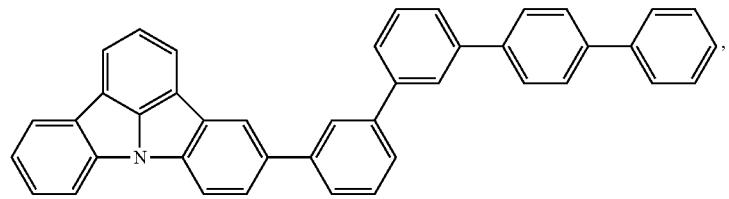
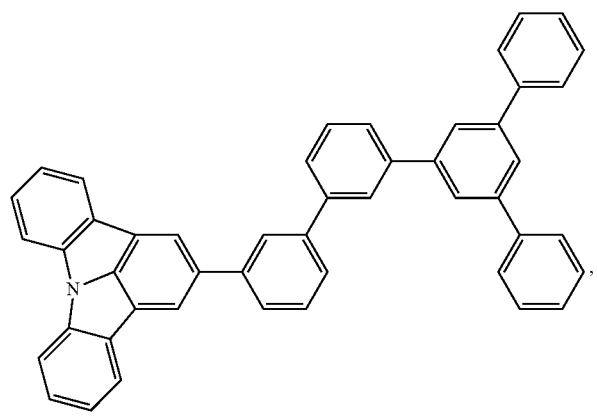
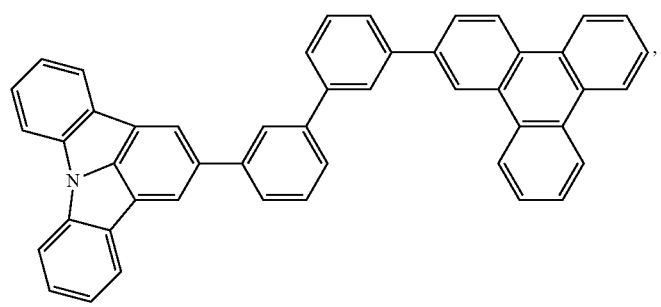
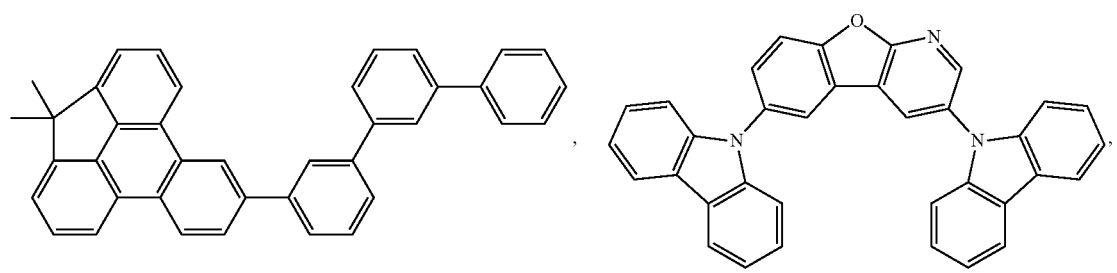
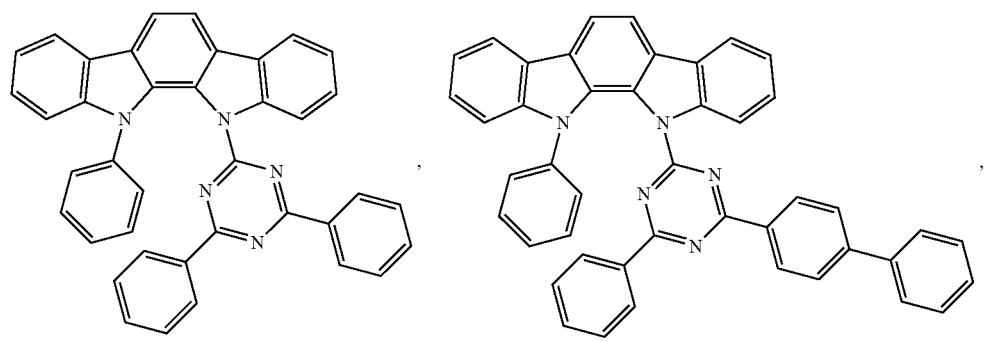

-continued
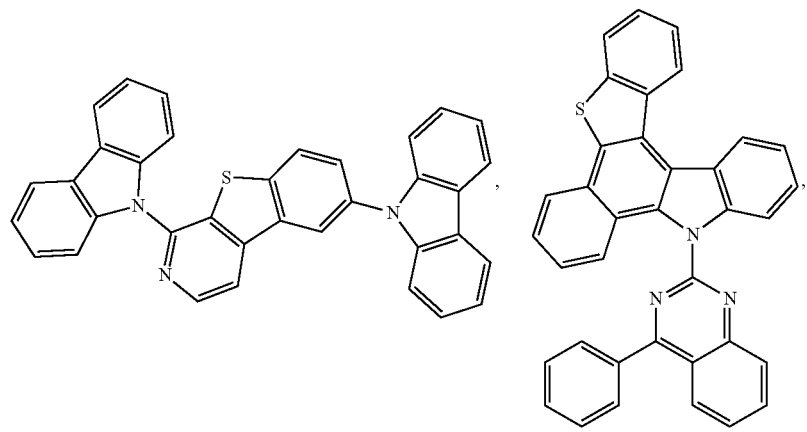
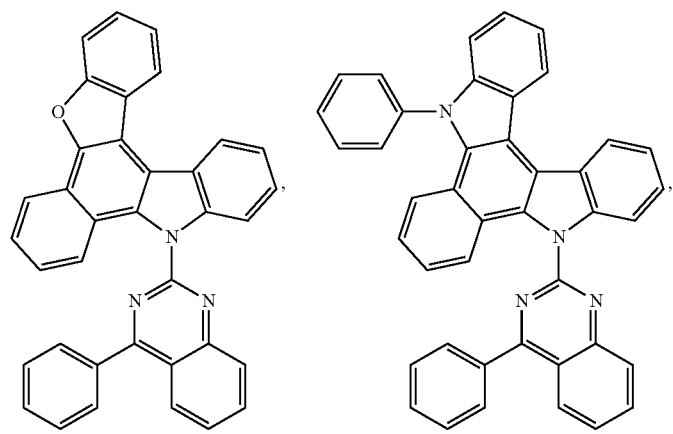
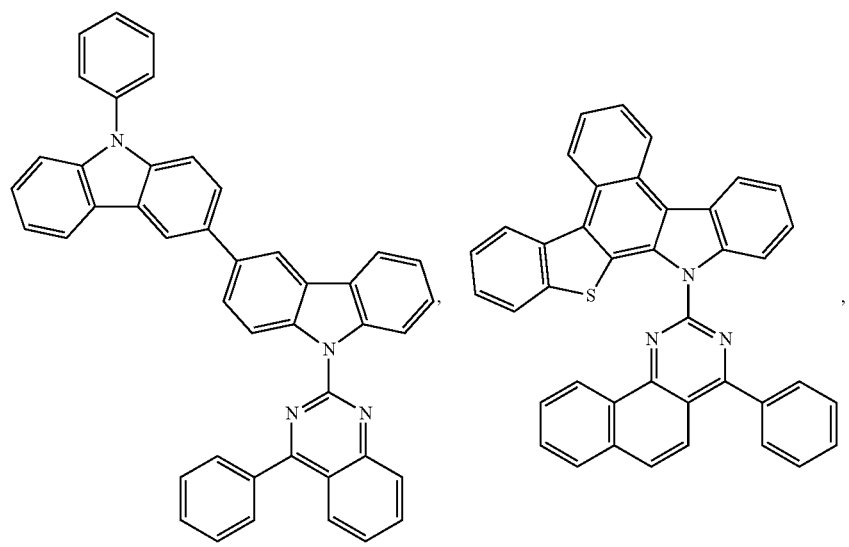

-continued
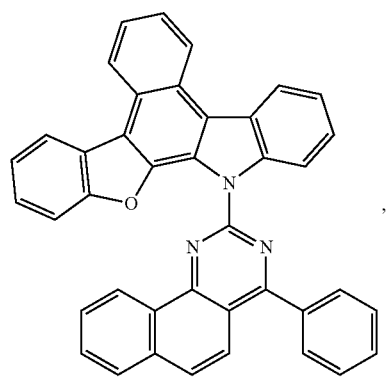
,
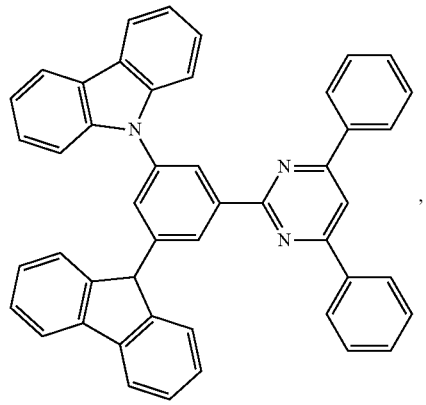
,
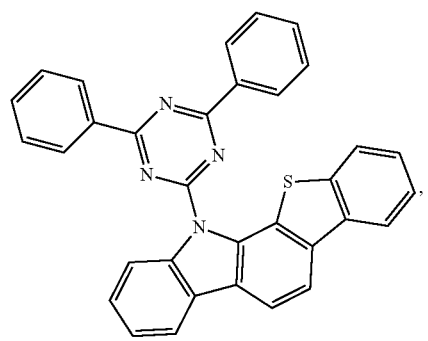
,
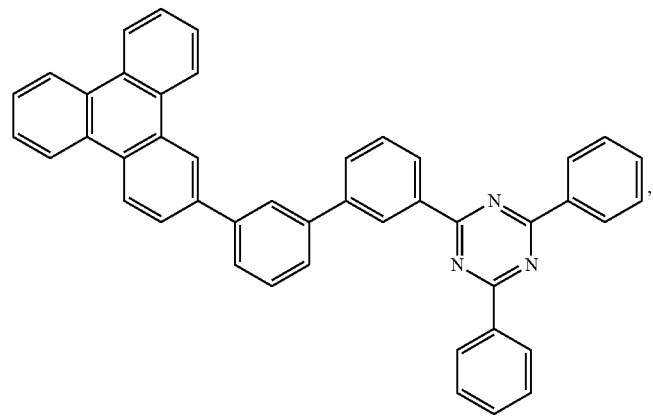
,
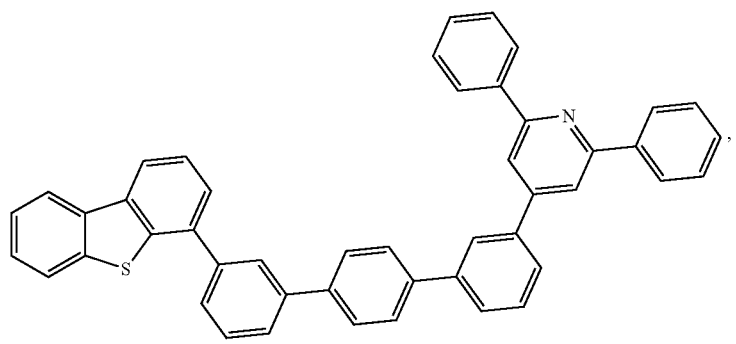
,
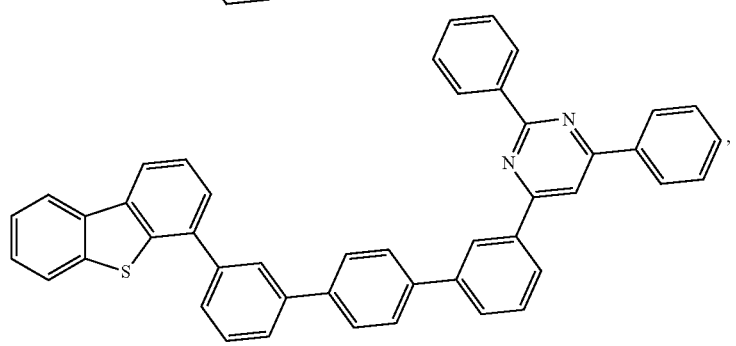
, -continued
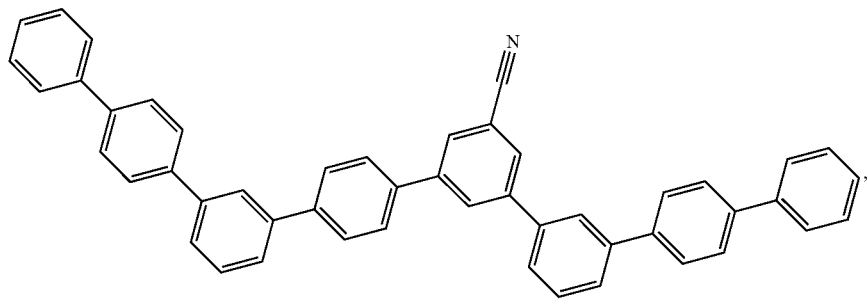
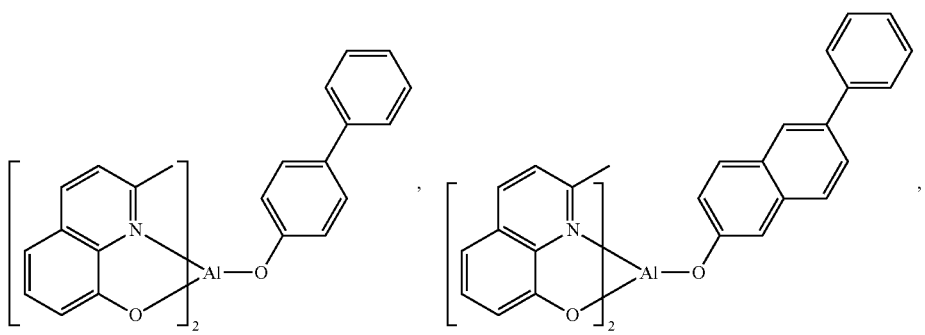
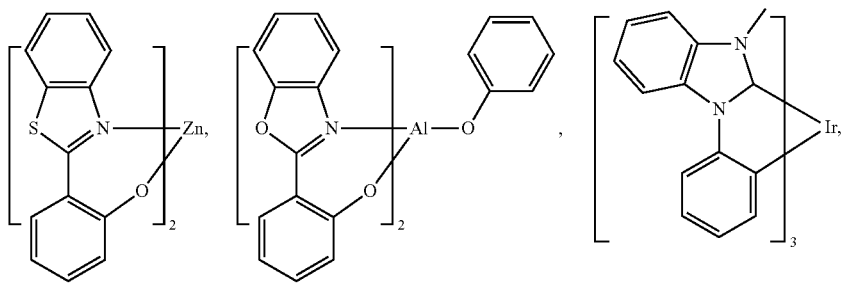
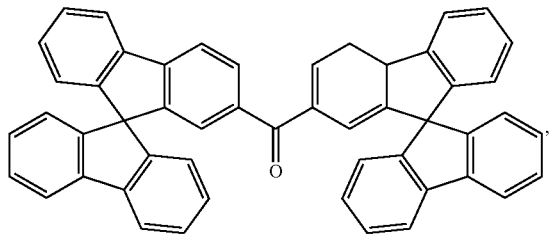
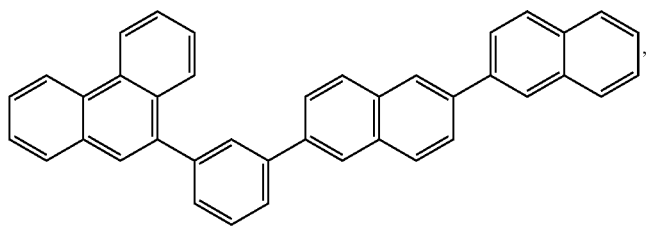
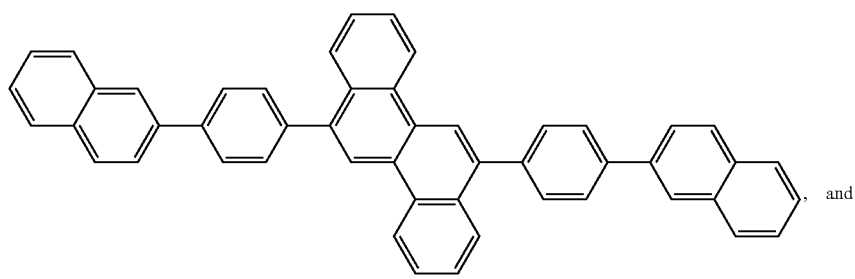

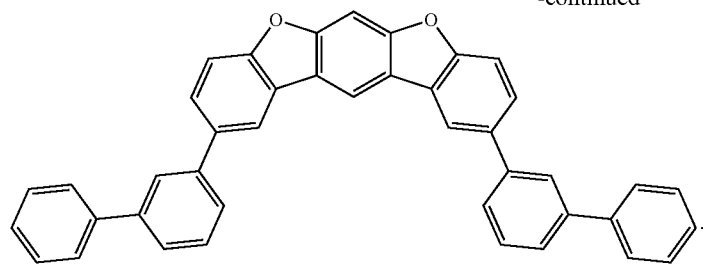

Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

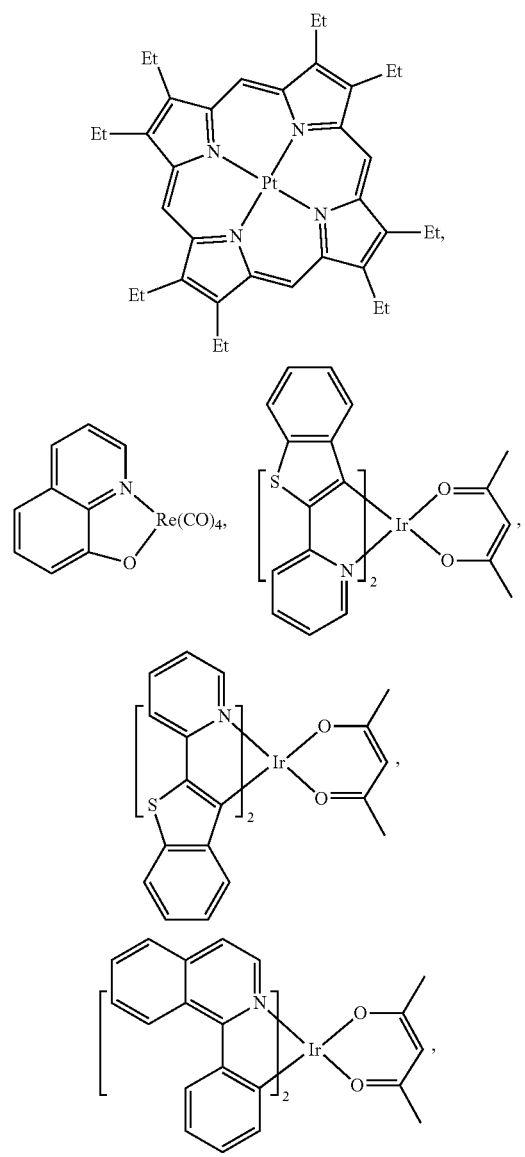

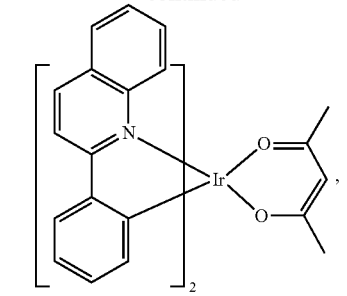
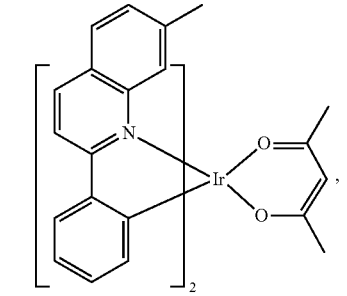
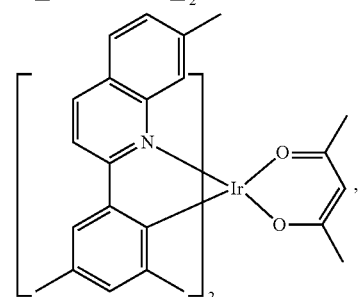
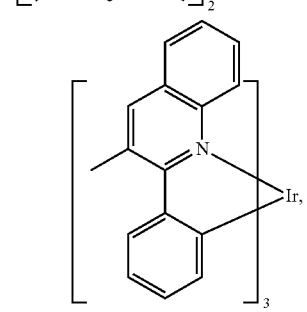
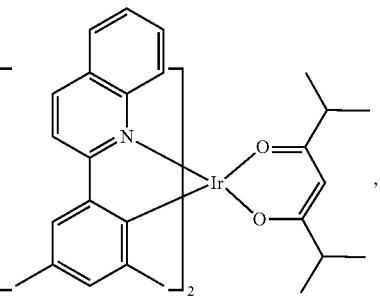
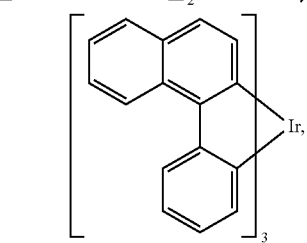
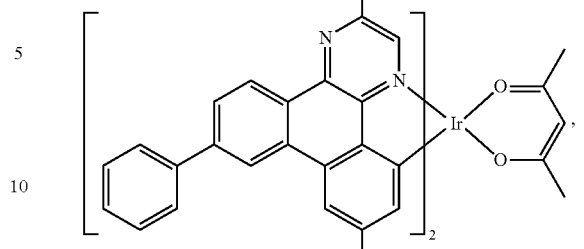
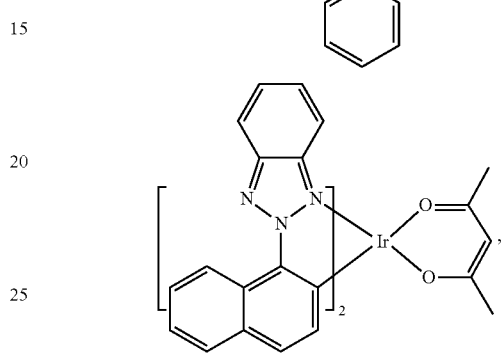
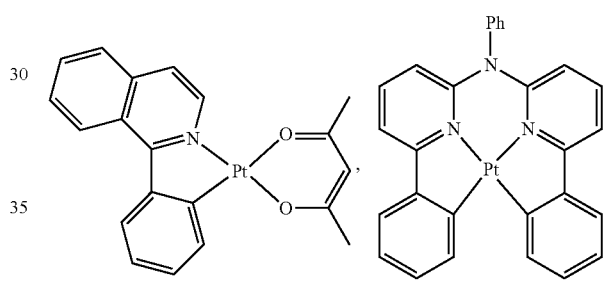
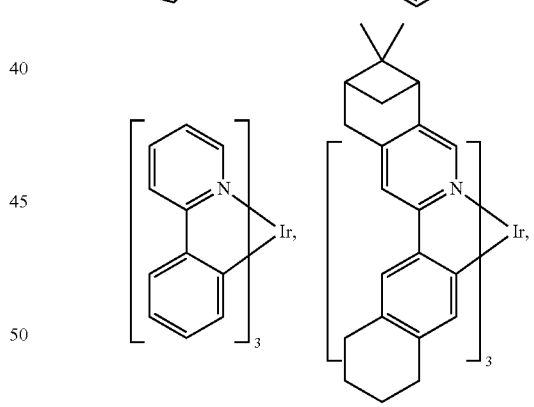
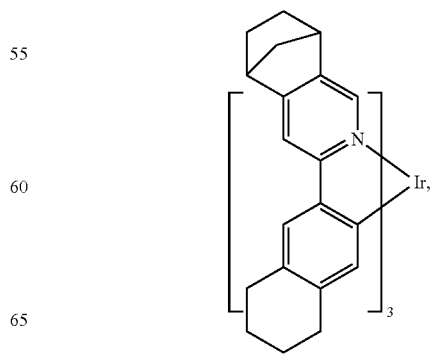

93
-continued
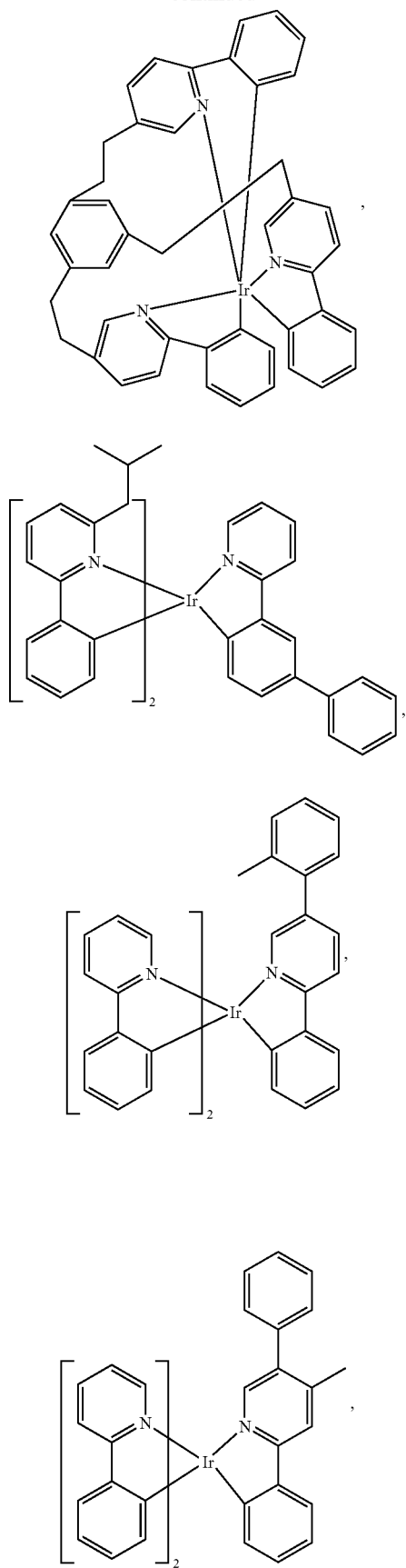
94
-continued
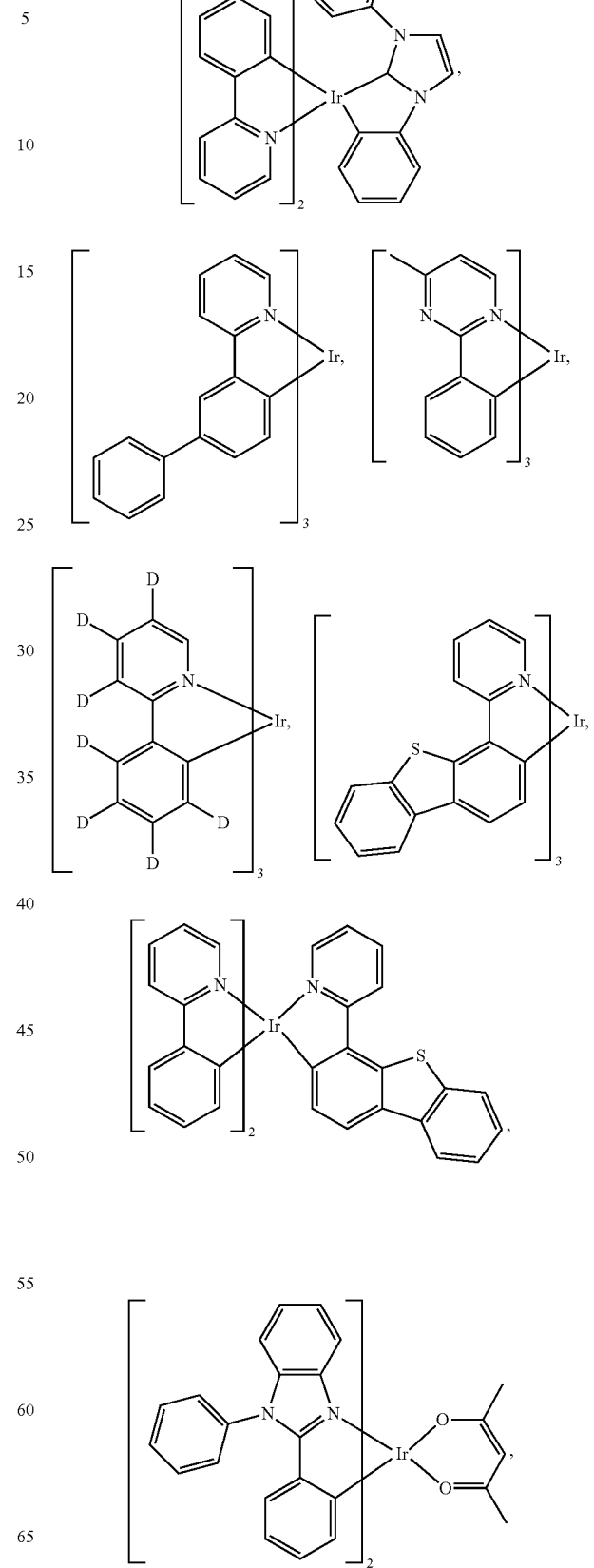

95
-continued
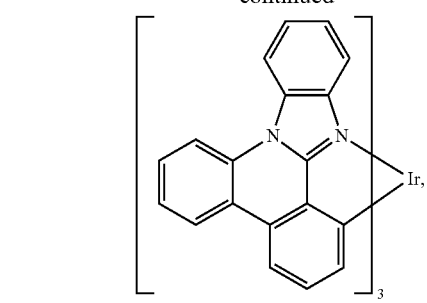
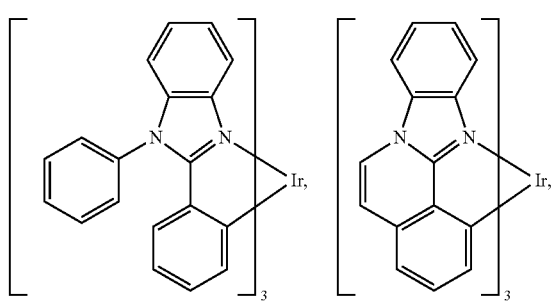
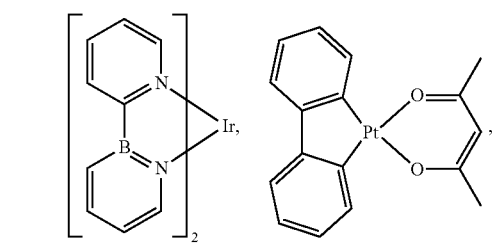
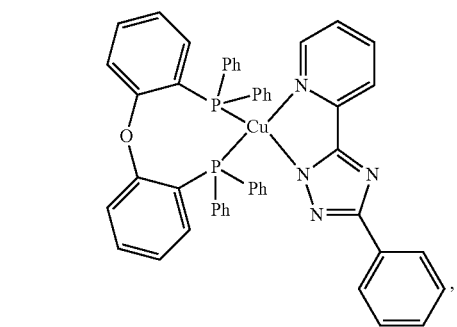
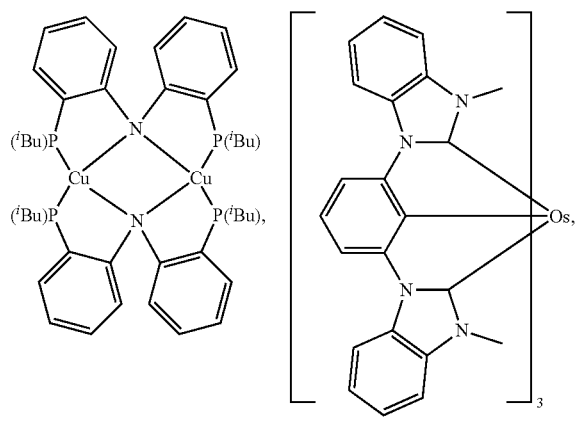
96
-continued
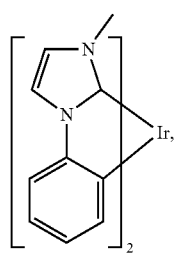
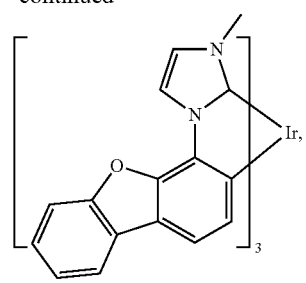
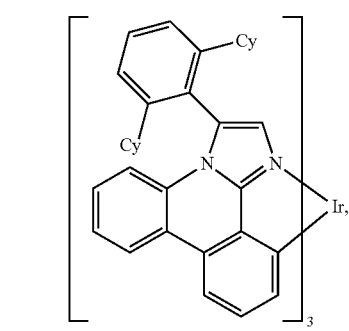
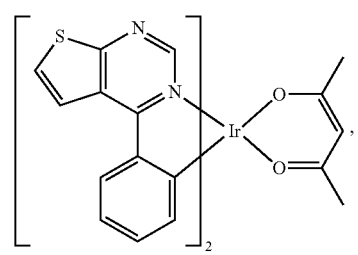
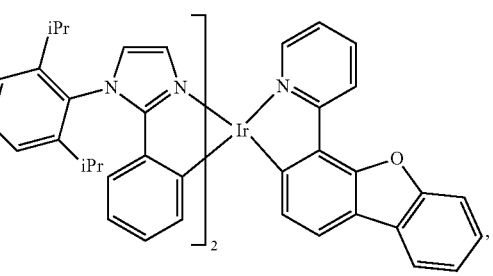
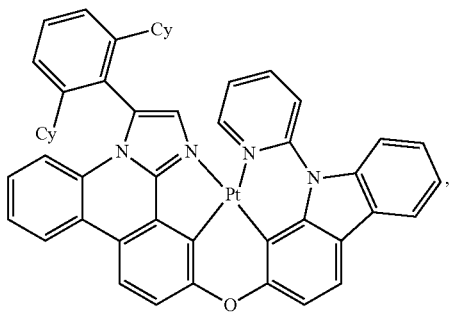

97
-continued
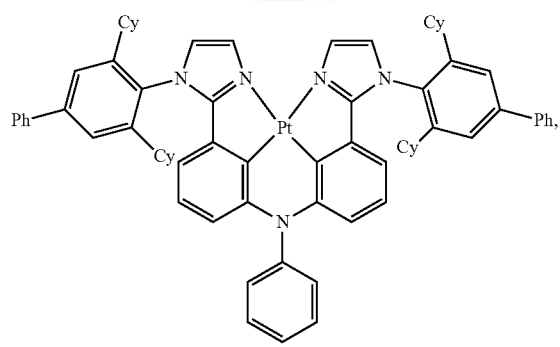
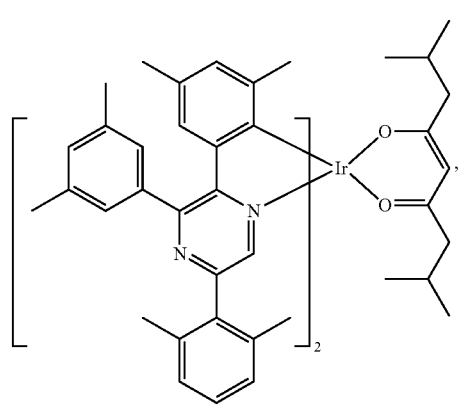
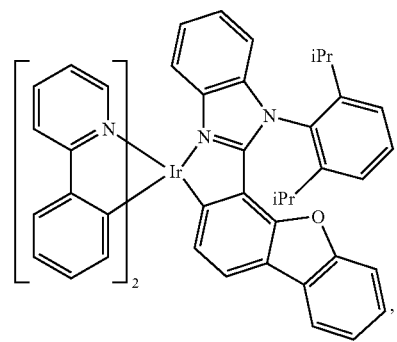
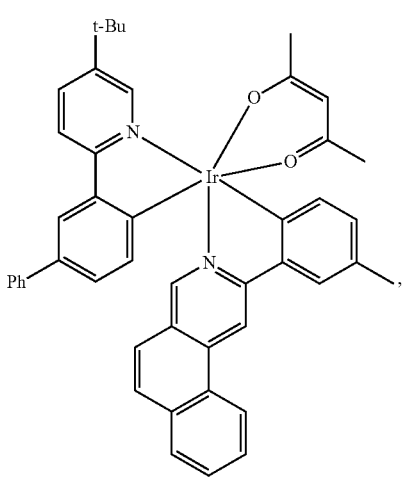
98
-continued
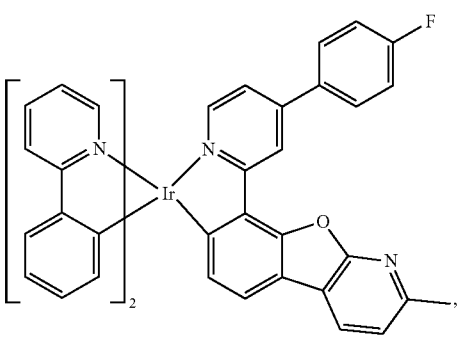
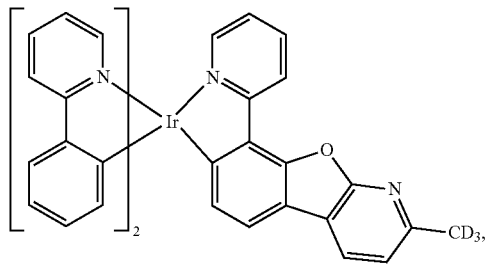
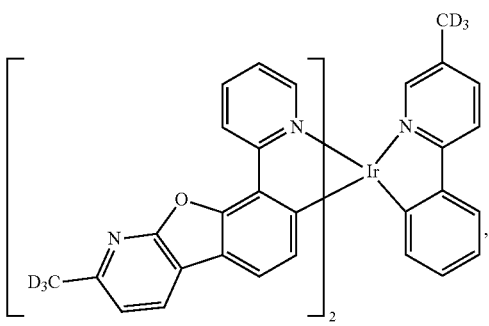
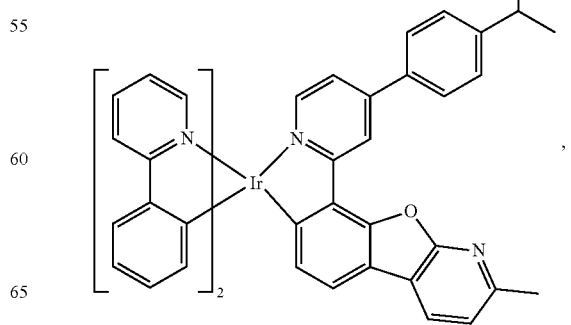
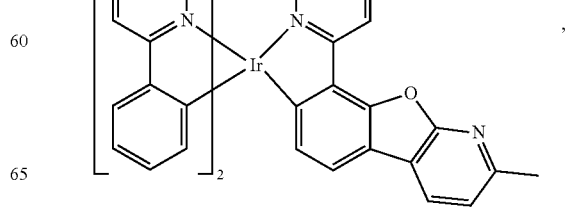

-continued
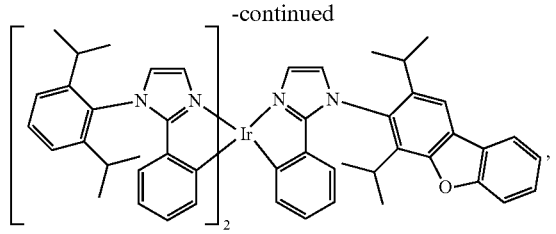
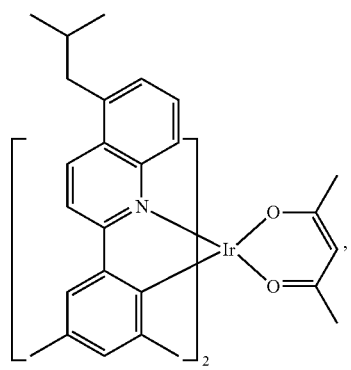
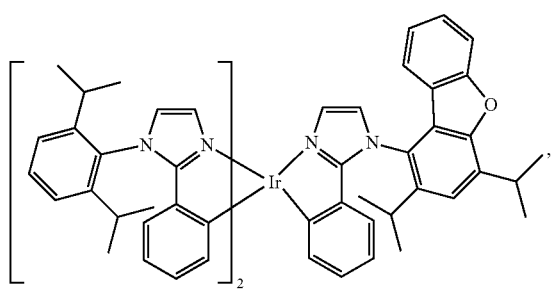
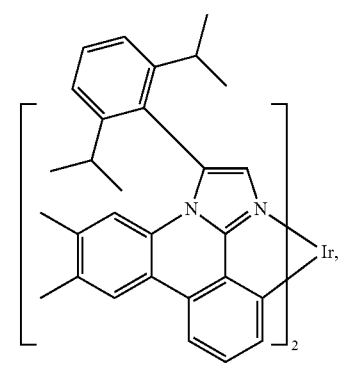
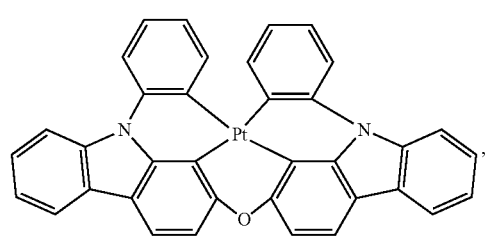
-continued
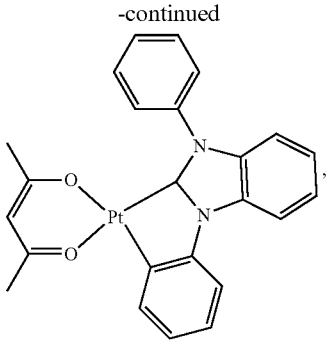
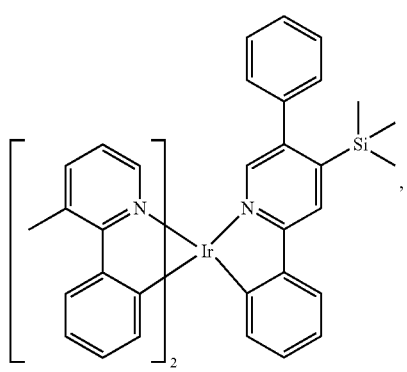
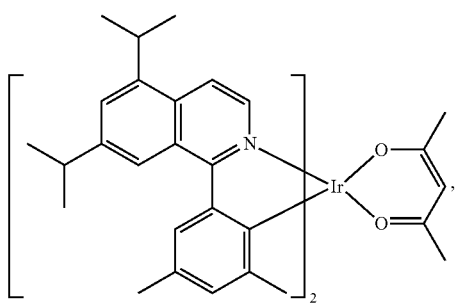
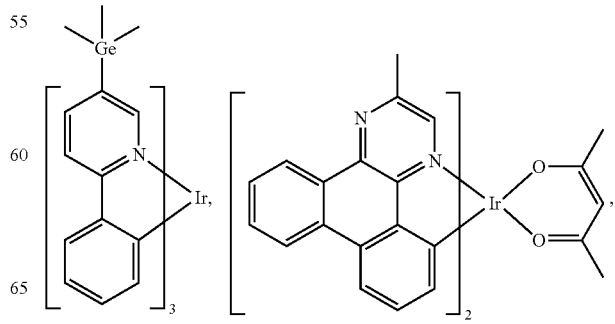

101
-continued
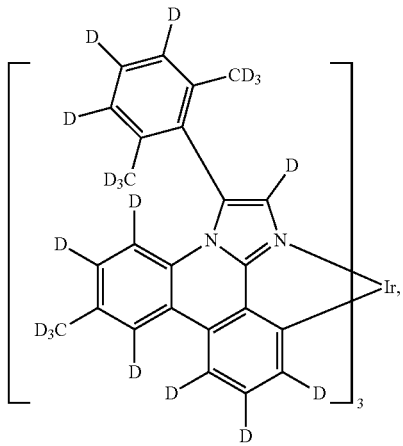
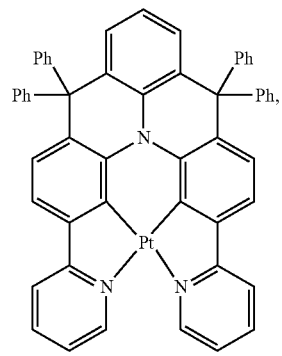
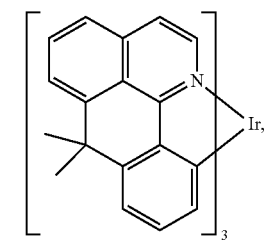
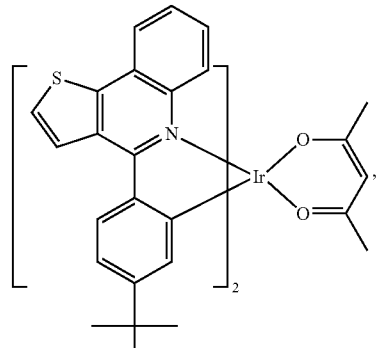
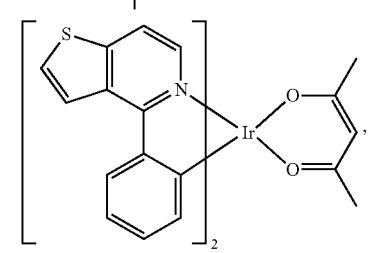
102
-continued
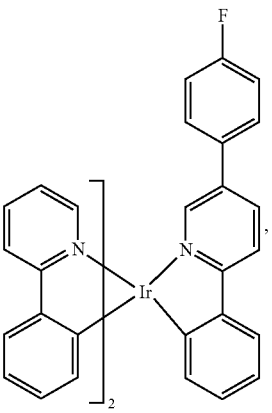
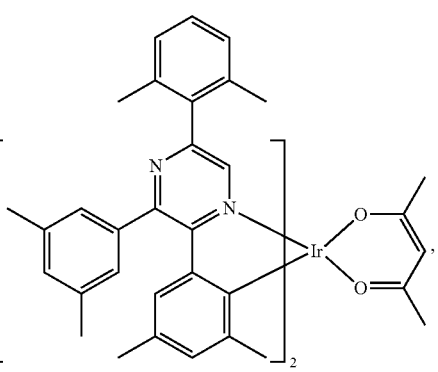
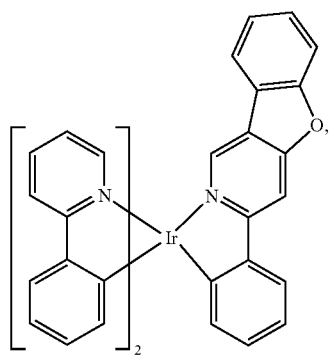
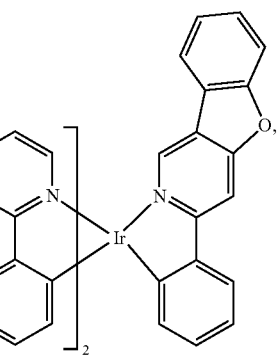
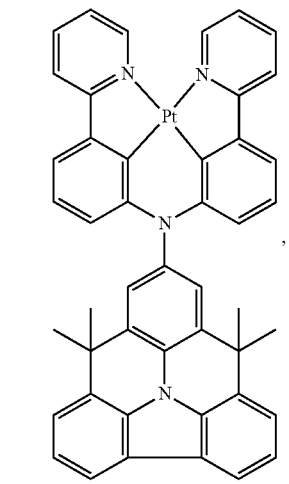

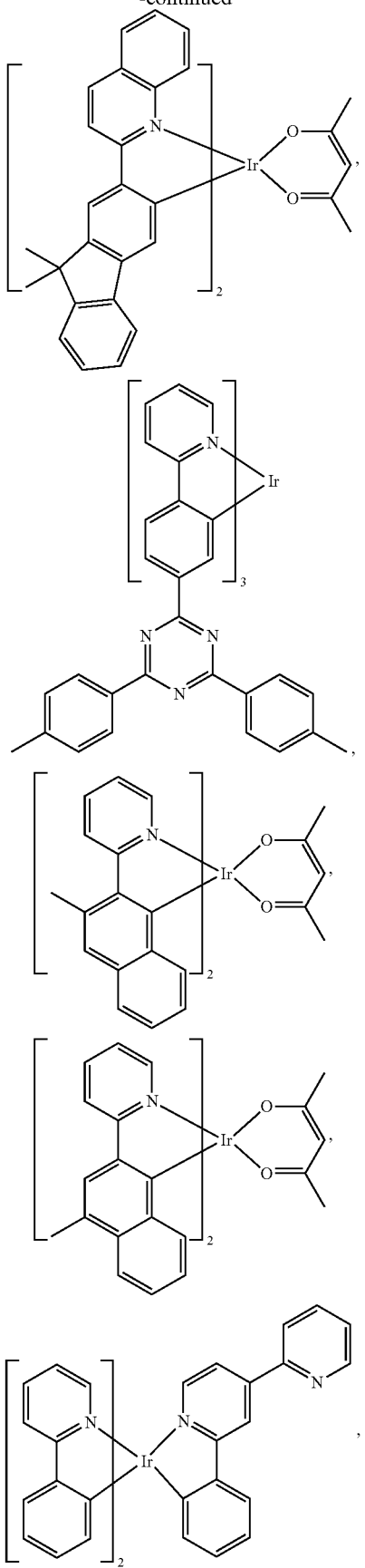
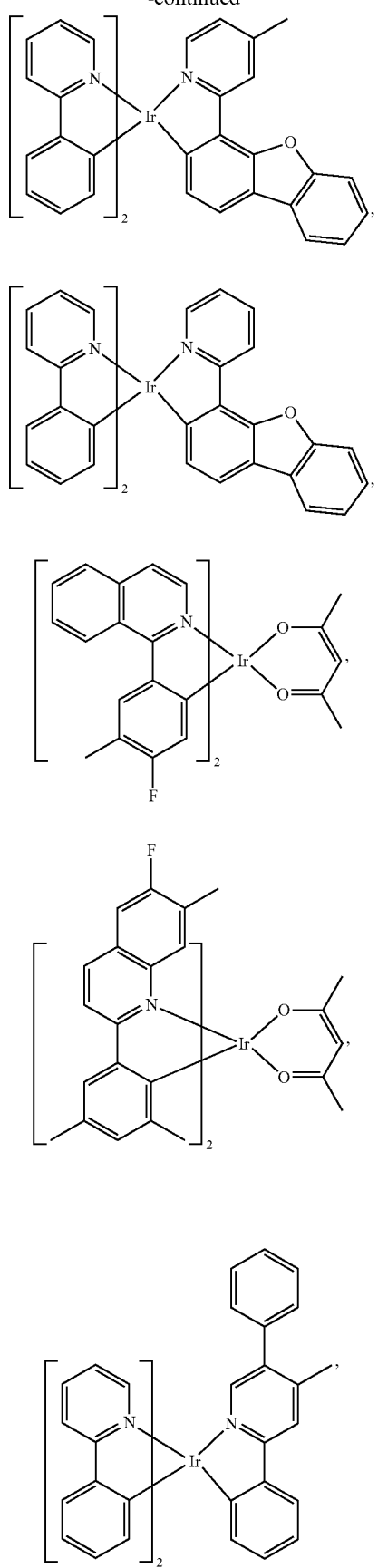

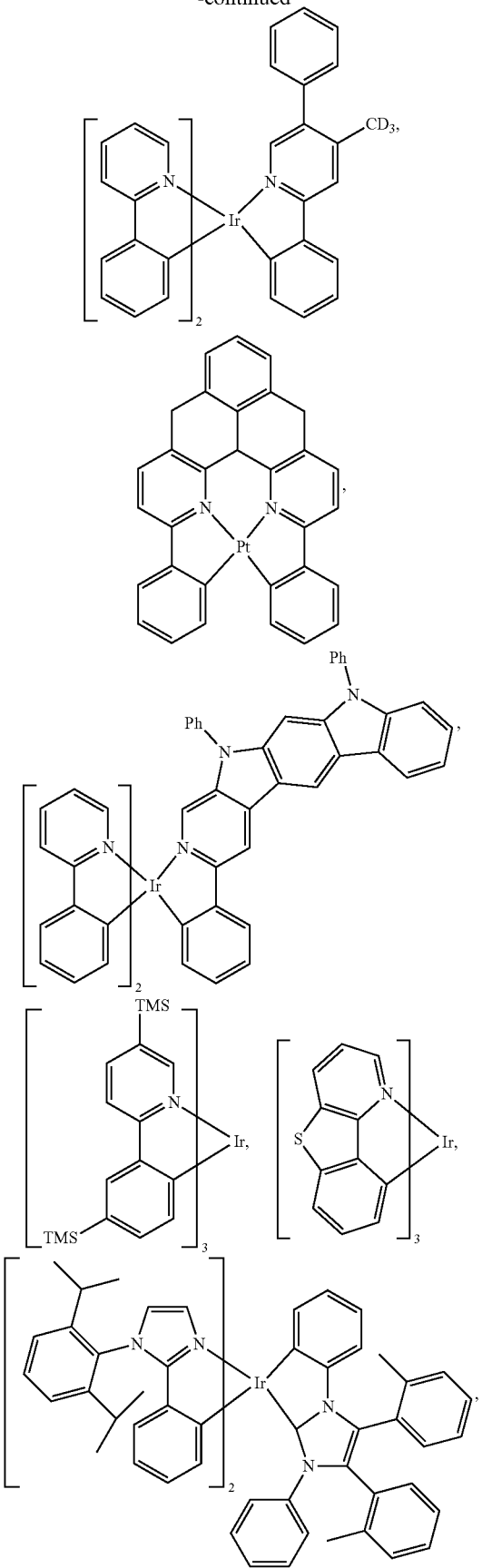
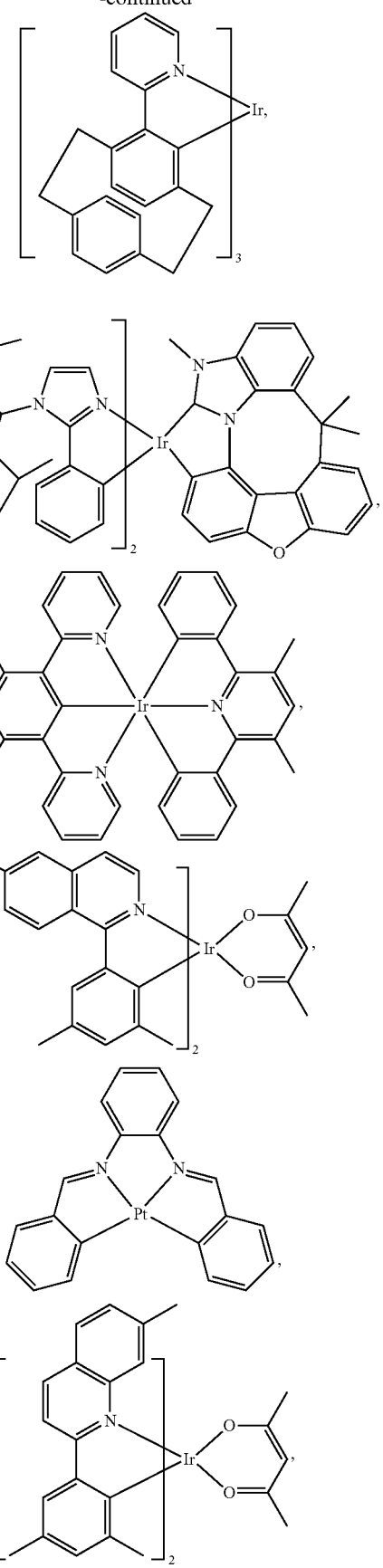

107
-continued
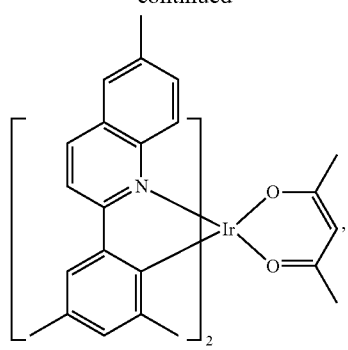
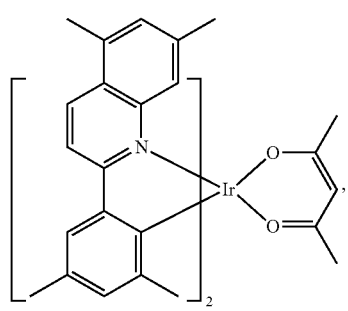
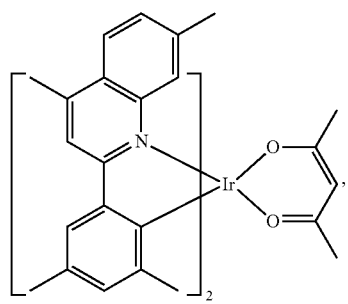
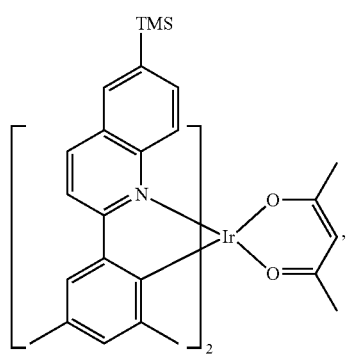
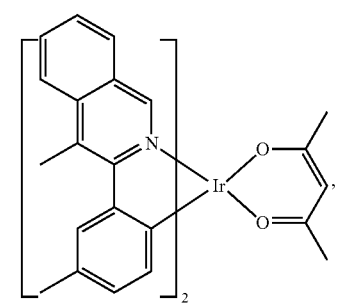
108
-continued
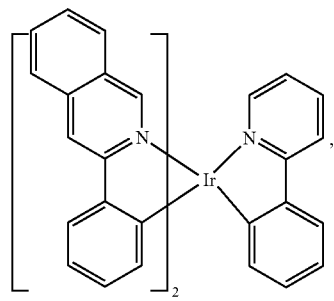
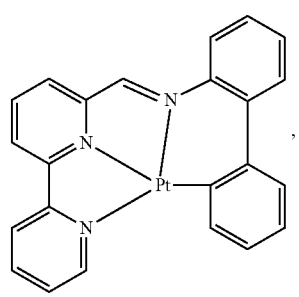
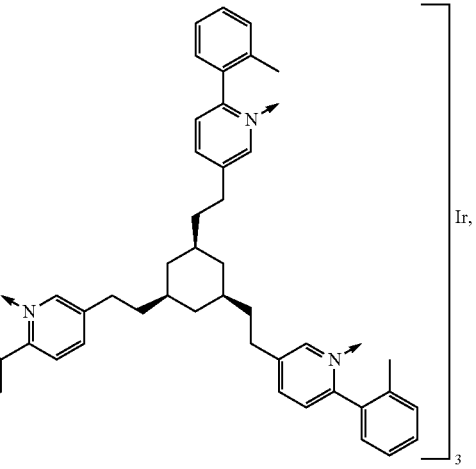
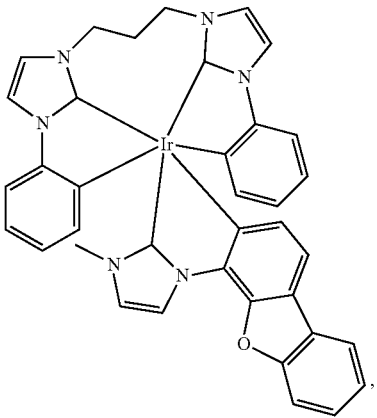

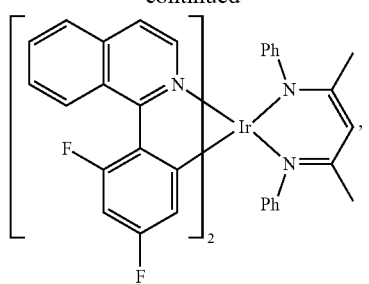
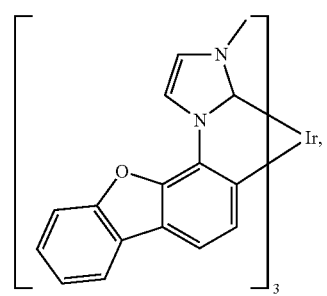
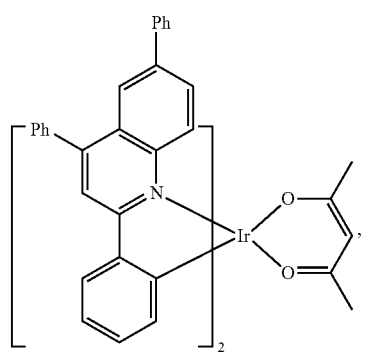
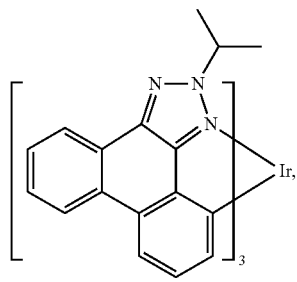
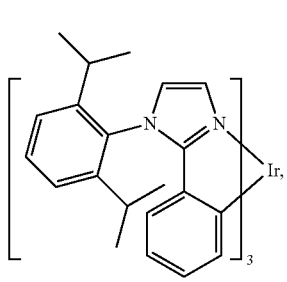
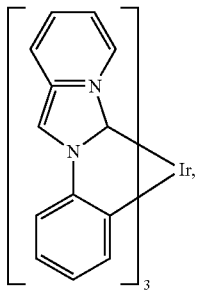
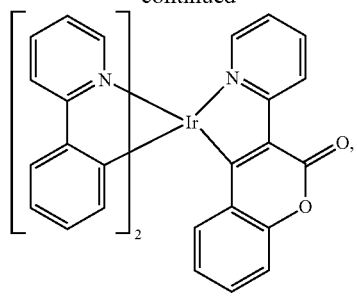
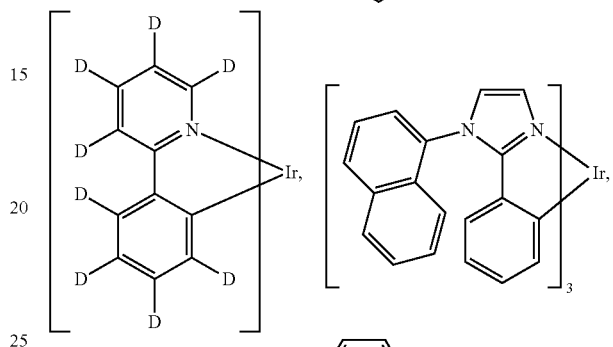
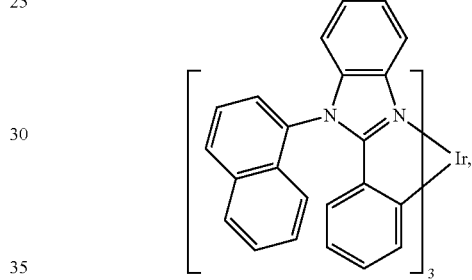
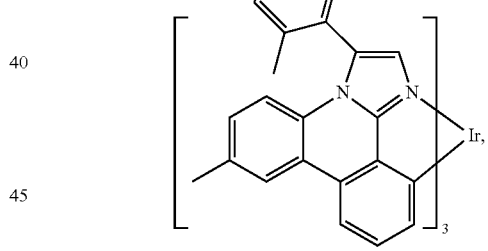
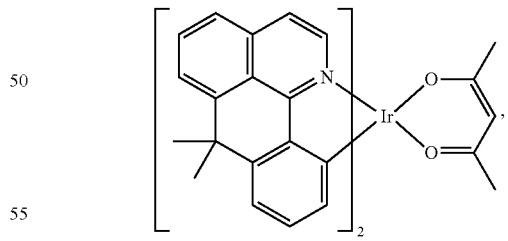
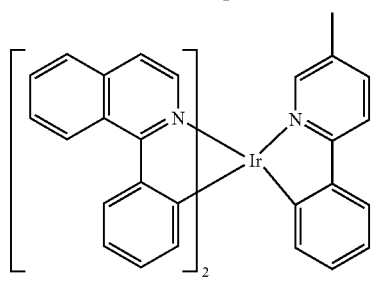

-continued

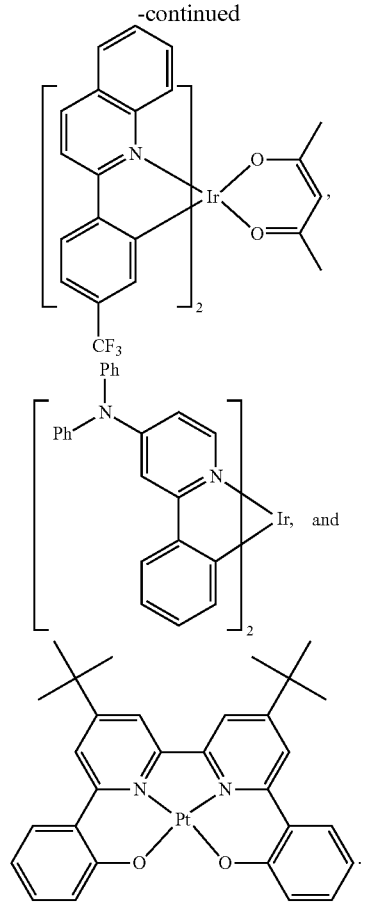

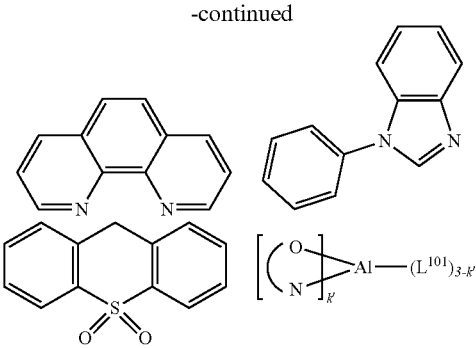

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

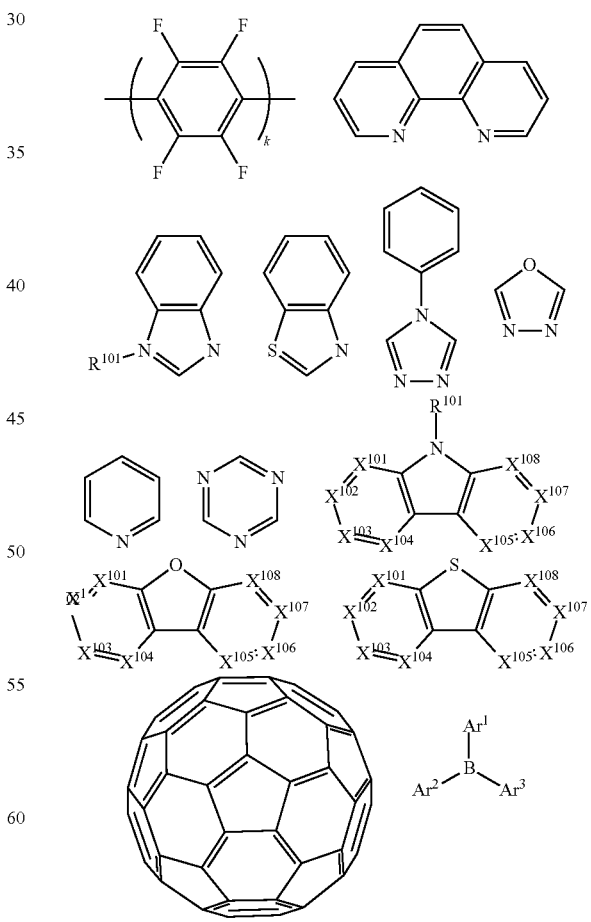

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

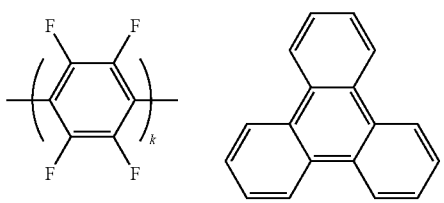

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

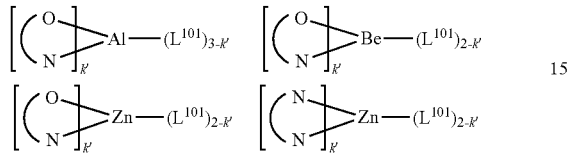

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US20101008990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

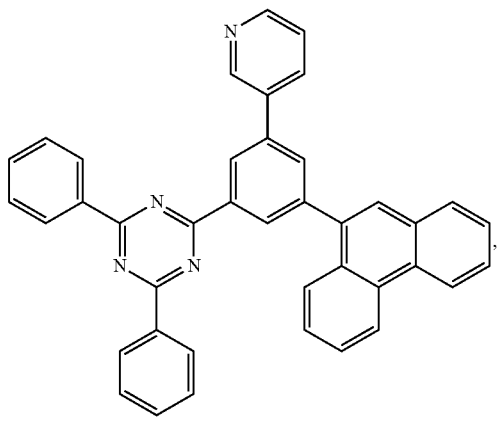

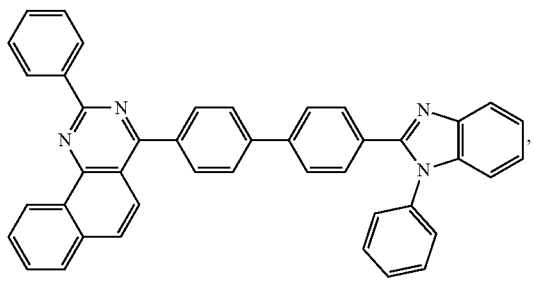

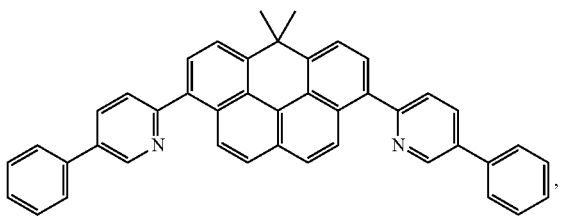

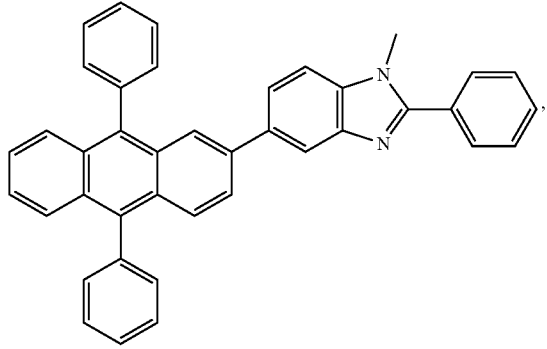

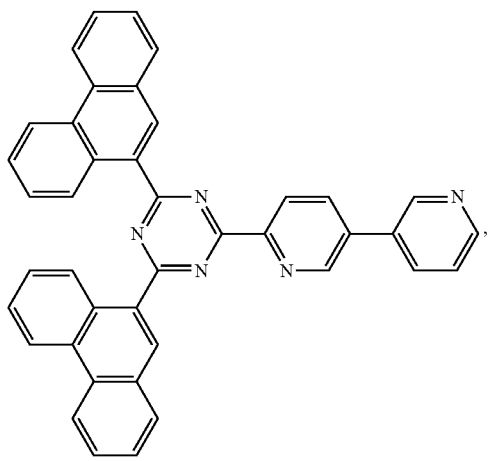

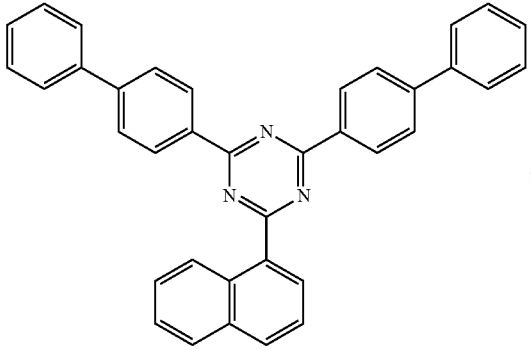

115
-continued
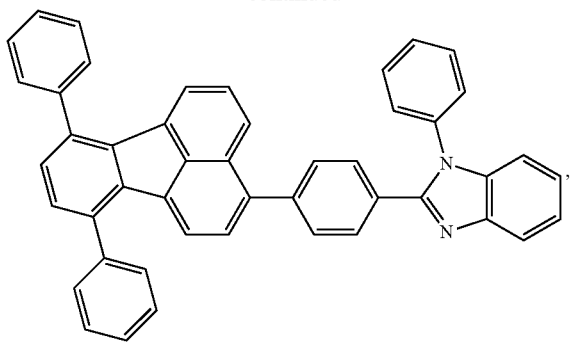
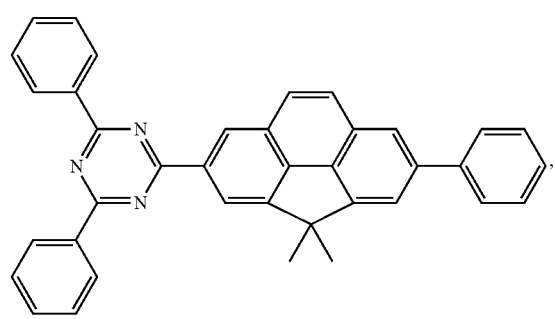
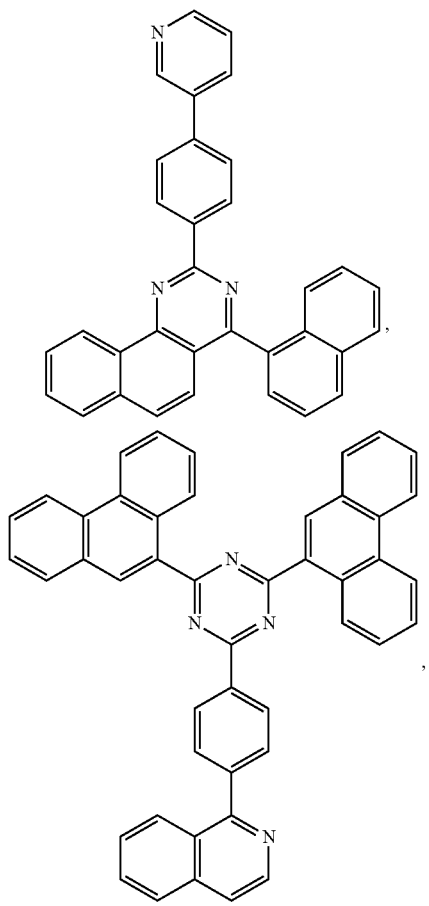
116
-continued
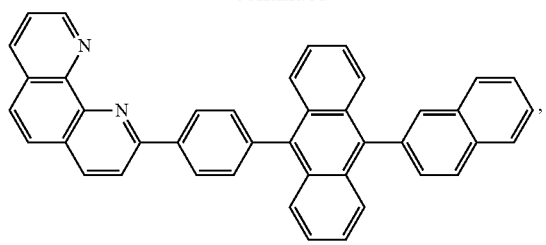
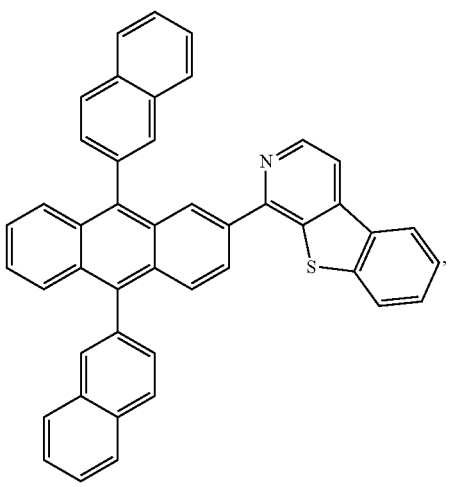
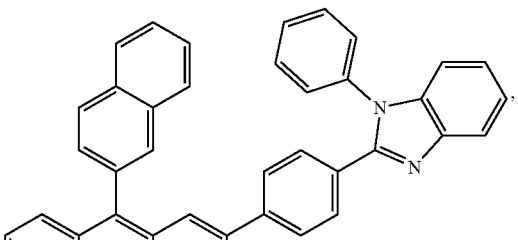
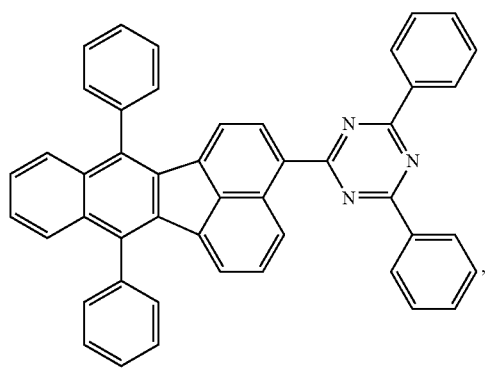

117
-continued
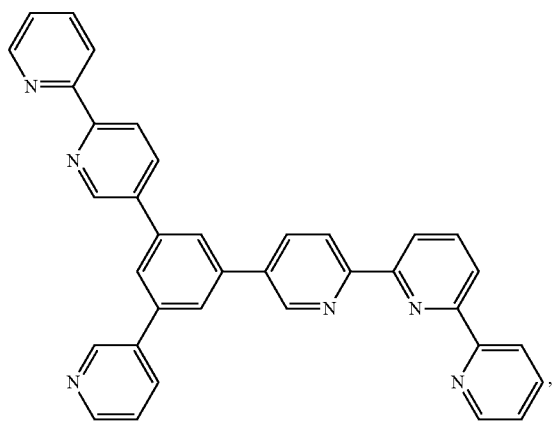
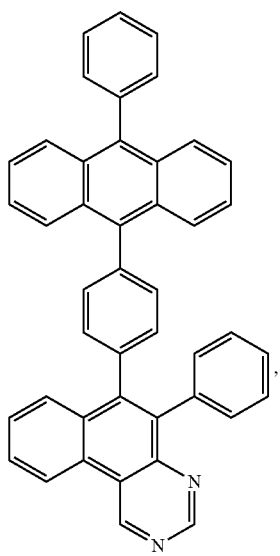
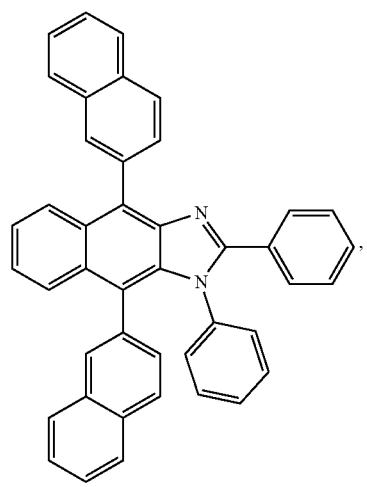
118
-continued
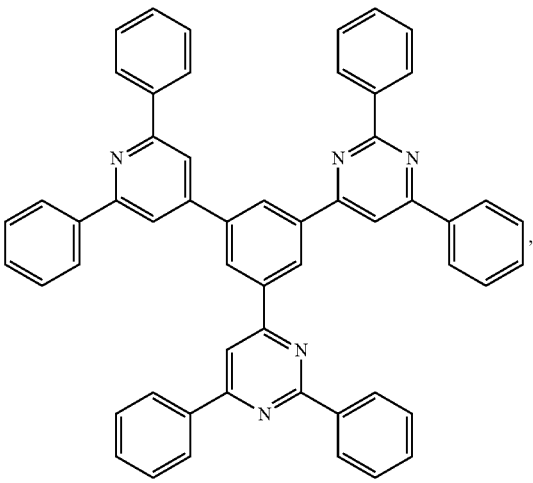
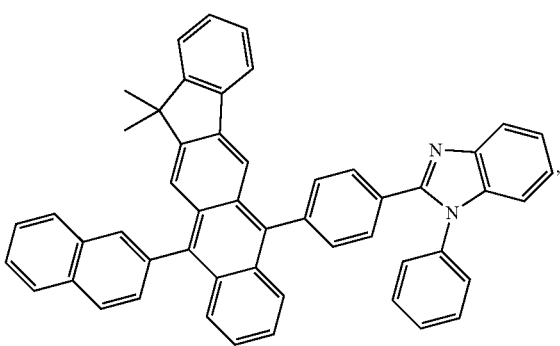

119
-continued
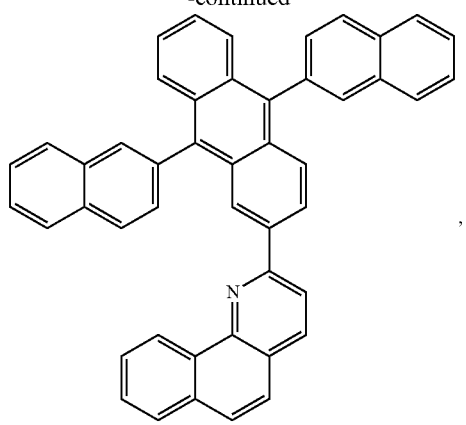
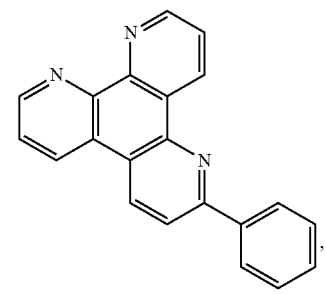
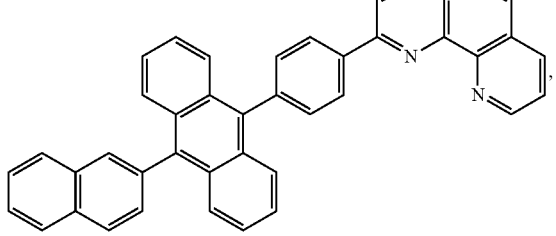
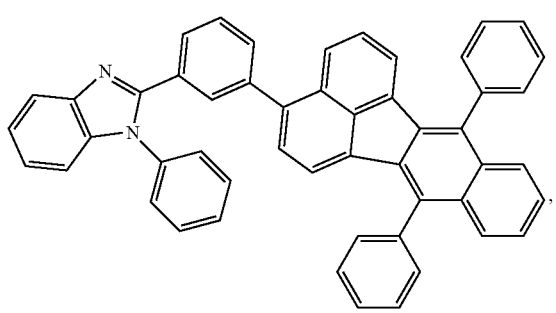
120
-continued
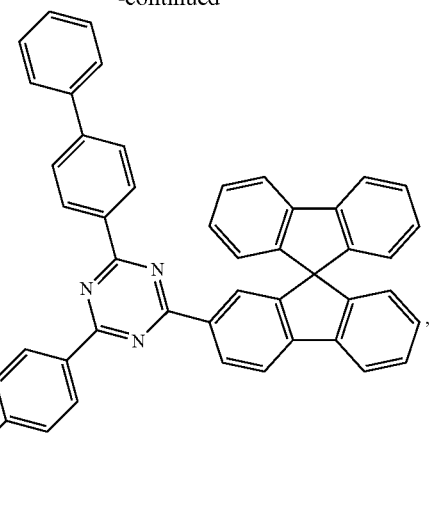
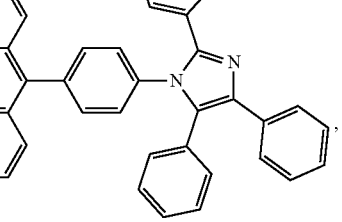
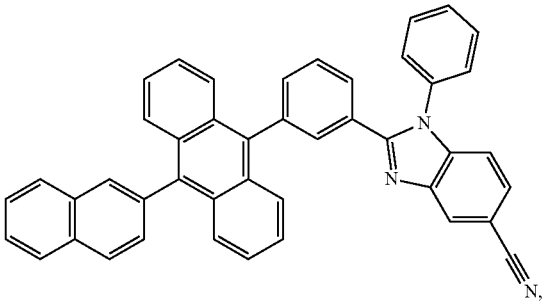
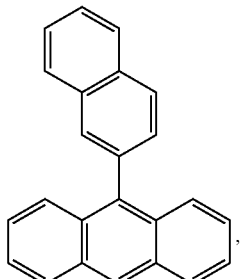
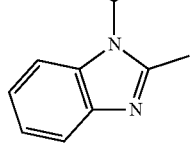

-continued

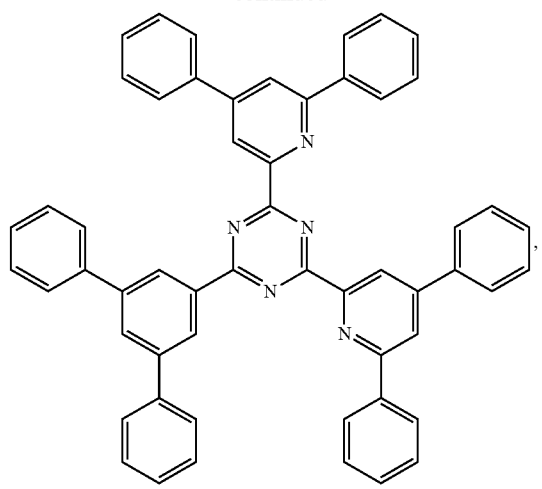

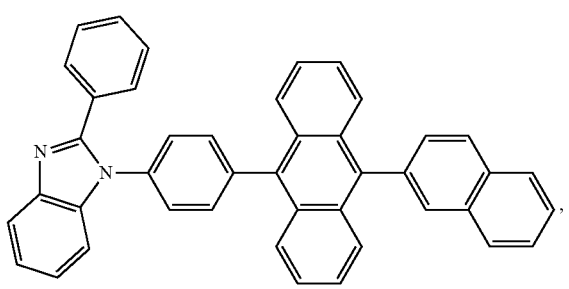

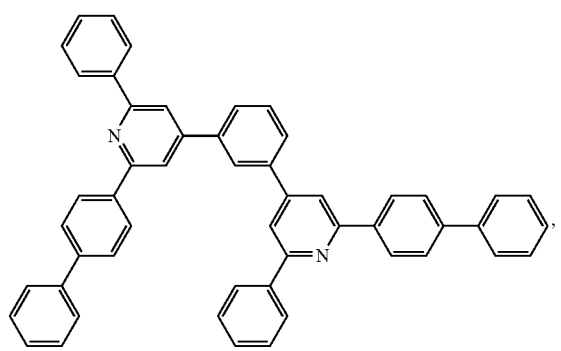

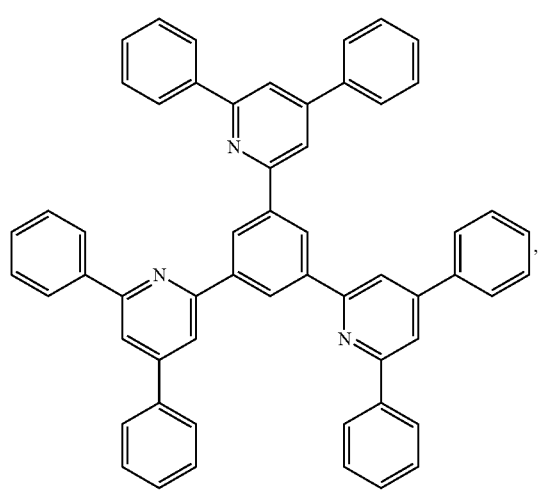

-continued

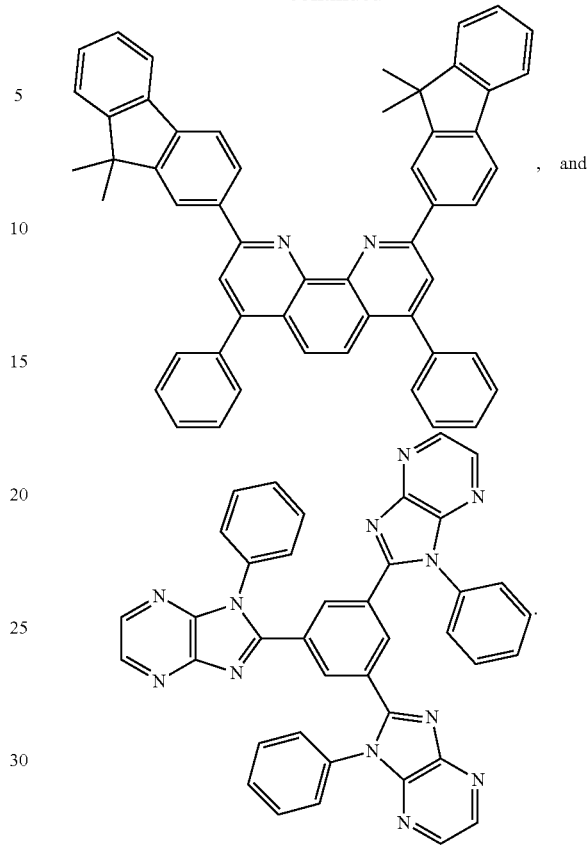

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

EXPERIMENTAL

The following Table 1 shows values of E, EL, ΔE, and FWHM for a variety of Free Ligands and compounds derived using the free ligand structure. As demonstrated by the data, lower ΔE values result in lower FWHM values. The values in Table 1 are much lower than conventional emitters, for example in Ir(ppy)$_3$, ΔE is about 370 meV, and its FWHM is about 75 nm. The data provided herein was generated using the methods and conditions described above.

| Compound Structures | E (T1 of the Compounds at 77 K*) | Free Ligand Structures | E_L (T1 of the Free Ligand at 77 K*) | ΔE (E_L-E) | FWHM** |
|---|---|---|---|---|---|
| | 530 nm (2.339 ev) | | 520 nm (2.384 ev) | 45 meV | 31 nm |
| | 530 nm (2.339 ev) | | 520 nm (2.384 ev) | 45 meV | 24 nm |
| 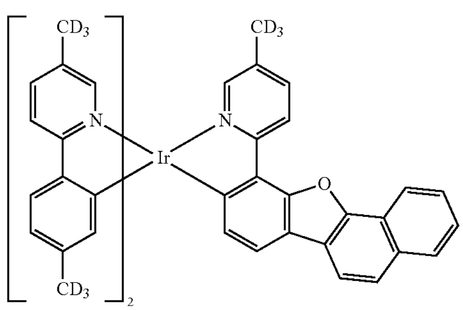 | 520 nm (2.384 ev) | | 472 nm (2.628 ev) | 244 meV | 58 nm |
| 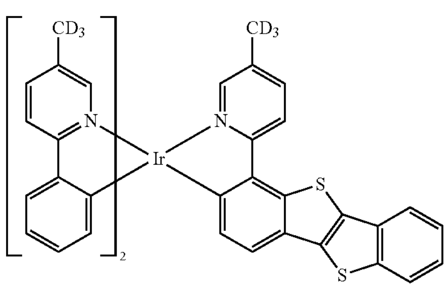 | 532 nm (2.331 ev) | | 492 nm (2.52 ev) | 189 meV | 59 nm |

-continued

| Compound Structures | E (T1 of the Compounds at 77 K*) | Free Ligand Structures | $E_L$ (T1 of the Free Ligand at 77 K*) | ΔE ($E_L$-E) | FWHM** |
|---|---|---|---|---|---|
| [structure with CD3 groups, Ir complex, benzofuran-naphthalene] | 523 nm (2.371 ev) | [free ligand with CD3 groups, benzofuran-naphthalene] | 516 nm (2.403 ev) | 32 meV | 23 nm |
| [structure with CD3 groups, Ir complex, benzofuran-quinoline] | 521 nm (2.380 ev) | [free ligand with CD3 groups, benzofuran-quinoline] | 499 nm (2.485 ev) | 105 meV | 31 nm |
| [structure with CD3 groups, Ir complex, benzofuran-naphthalene isomer] | 528 nm (2.348 ev) | [free ligand with CD3 groups, benzofuran-naphthalene isomer] | 518 nm (2.394 ev) | 46 meV | 19 nm |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound having a metal coordination complex structure;
    wherein the compound is capable of functioning as a phosphorescent emitter in an organic light emitting device at room temperature;
    wherein the compound has a first bidentate ligand coordinated to a metal;
    wherein the first bidentate ligand comprises a first benzene ring coordinated to the metal;
    wherein the metal is iridium;
    wherein the first benzene ring is fused with a second aromatic ring;
    wherein the second aromatic ring is fused with a third aromatic ring;
    wherein a free-state of the first ligand has a first triplet energy T1 of EL at 77K;
    wherein the compound has a first triplet energy T1 of E at 77K;
    wherein the difference in energy between E and EL is 4E;
    wherein ΔE is ≤250 meV; and
    wherein the compound has a triplet emission spectrum with a full width at half maximum (FWHM) value of no more than 45 nm at 22° C.

2. The compound of claim 1, wherein ΔE is ≤200 meV.

3. The compound of claim 1, wherein the compound has a triplet emission spectrum with a FWHM value of no more than 40 nm at 22° C.

4. The compound of claim 1, wherein the compound has a metal-carbon bond.

5. The compound of claim 1, wherein the third aromatic ring is fused with a fourth aromatic ring.

6. The compound of claim 1, wherein the second aromatic ring is a five-membered ring.

7. The compound of claim 1, wherein the compound comprises a pyridine ring coordinated to the metal, and the pyridine ring is either unsubstituted or substituted with at least one group selected from the group consisting of alkyl, cycloalkyl, fully or partially deuterated variants thereof, and combination thereof.

8. The compound of claim 1, wherein the compound has a formula of $M(L_A)_x(L_B)_y(L_C)_z$ wherein $L_A$, $L_B$ and $L_C$ are each a bidentate ligand; and wherein x is 1, 2, or 3; y is 0, 1, or 2; z is 0, 1, or 2; and x+y+z is the oxidation state of the metal M.

9. The compound of claim 8, wherein $L_A$, $L_B$, and $L_C$ are each independently selected from the group consisting of:

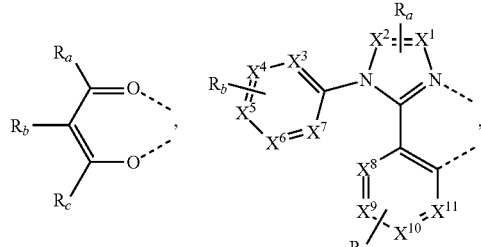

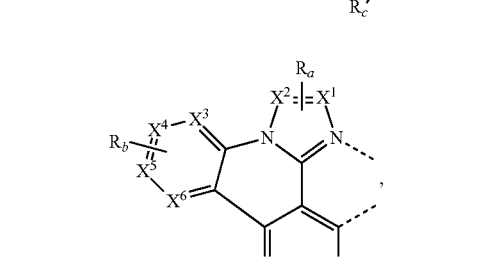

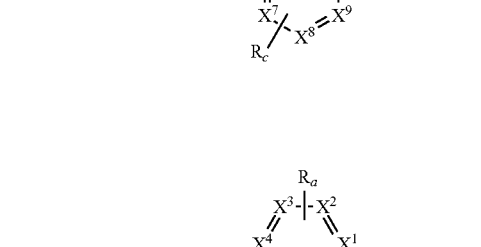

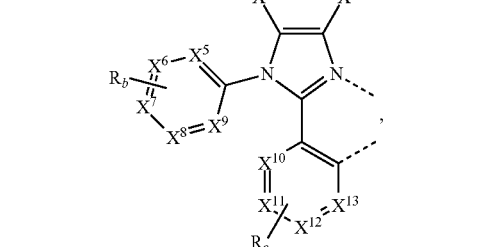

-continued

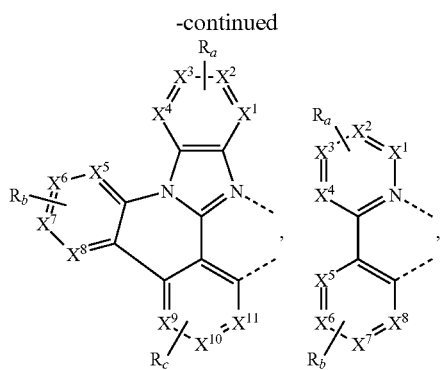

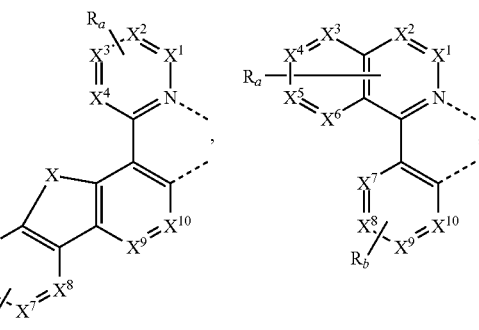

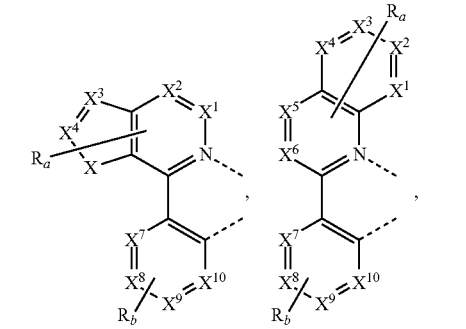

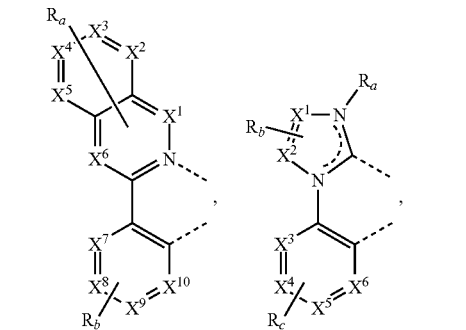

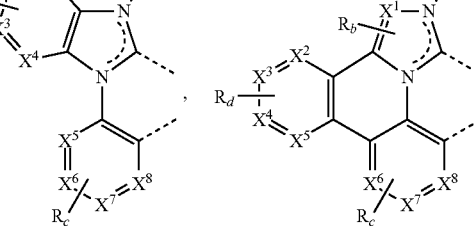

-continued

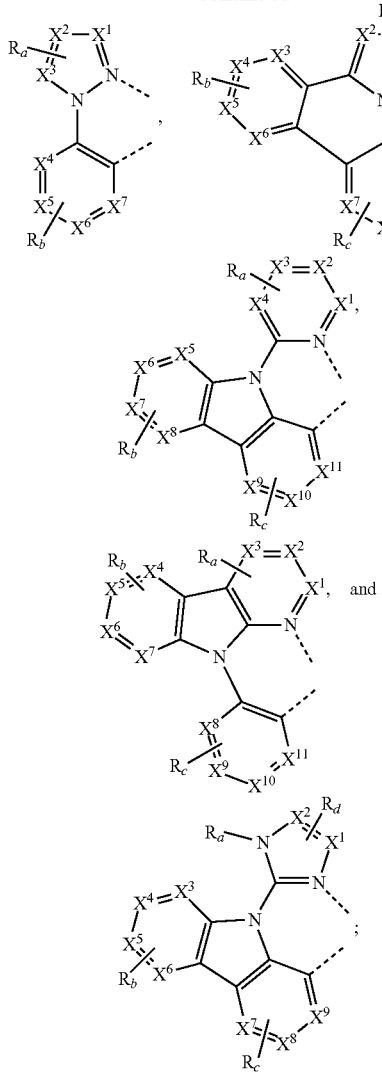

wherein each $X^1$ to $X^{13}$ are independently selected from the group consisting of carbon and nitrogen;
wherein X is selected from the group consisting of BR', NR', PR', O, S, Se, C=O, S=O, $SO_2$, CR'R", SiR'R", and GeR'R";
wherein R' and R" are optionally fused or joined to form a ring;
wherein each $R_a$, $R_b$, $R_c$, and $R_d$ may represent from mono substitution to the maximum possible number of substitution, or no substitution;
wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein any two adjacent substituents of $R_a$, $R_b$, $R_c$, and $R_d$ are optionally fused or joined to form a ring or form a multidentate ligand.

10. The compound of claim 9, wherein at least one pair of substituents $R_a$, $R_b$, $R_c$, and $R_d$ within the same ring are joined and fused into a ring.

11. The compound of claim 9, wherein the compound has the formula of $Ir(L_A)_2(L_B)$, wherein $L_A$ has the formula:

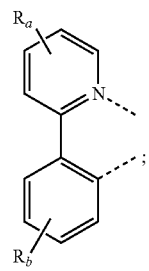

and
wherein $L_B$ is different from $L_A$, and has a formula selected from the group consisting of:

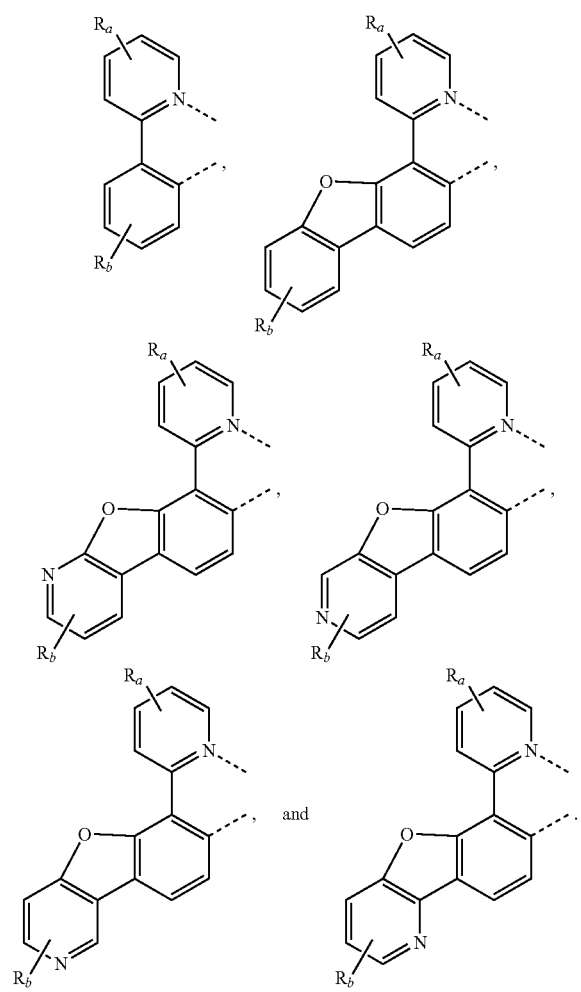

12. A formulation comprising a compound according to claim 1.

13. An organic light emitting device (OLED) comprising:
an anode;
a cathode; and an organic layer, disposed between the anode and the cathode, comprising a compound having a metal coordination complex structure;

wherein the compound is capable of functioning as a phosphorescent emitter in an organic light emitting device at room temperature;

wherein the compound has a first bidentate ligand coordinated to a metal;

wherein the first bidentate ligand comprises a first benzene ring coordinated to the metal;

wherein the metal is iridium;

wherein the first benzene ring is fused with a second aromatic ring;

wherein the second aromatic ring is fused with a third aromatic ring;

wherein a free-state of the first ligand has a first triplet energy T1 of $E_L$ at 77K;

wherein the compound has a first triplet energy T1 of E at 77K;

wherein the difference in energy between E and $E_L$ is $\Delta E$;

wherein $\Delta E$ is ≤250 meV; and wherein the compound has a triplet emission spectrum with a full width at half maximum (FWHM) value of no more than 45 nm at 22° C.

14. The OLED of claim 13, wherein the organic layer is an emissive layer and the compound is an emissive dopant or a non-emissive dopant.

15. The OLED of claim 13, wherein the organic layer further comprises a host, wherein host comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

16. The OLED of claim 15, wherein the host is selected from the group consisting of:

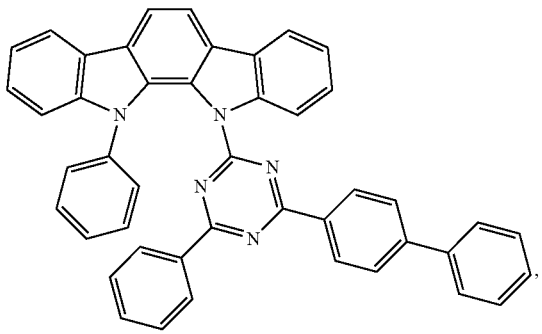

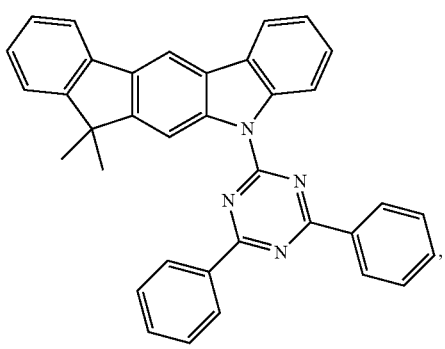

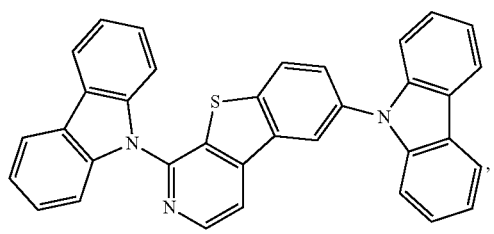

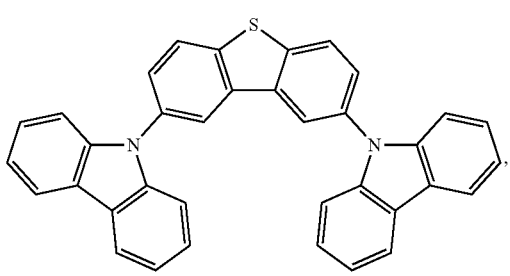

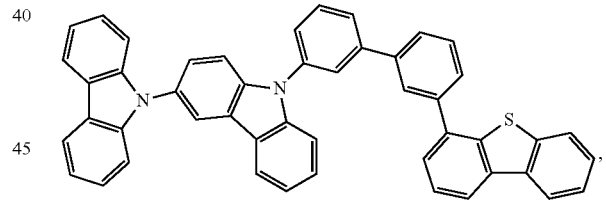

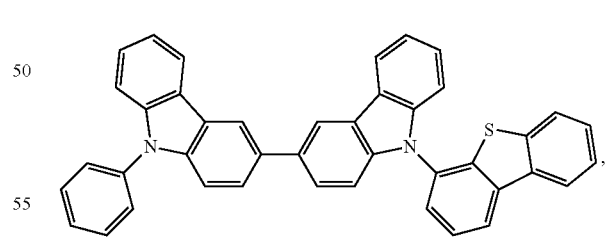

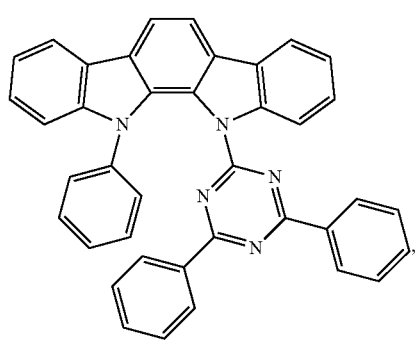

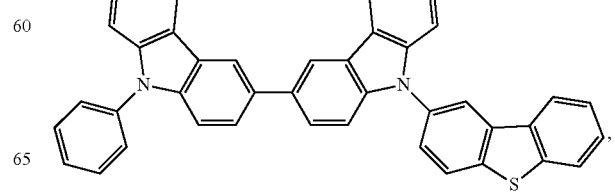

133
-continued
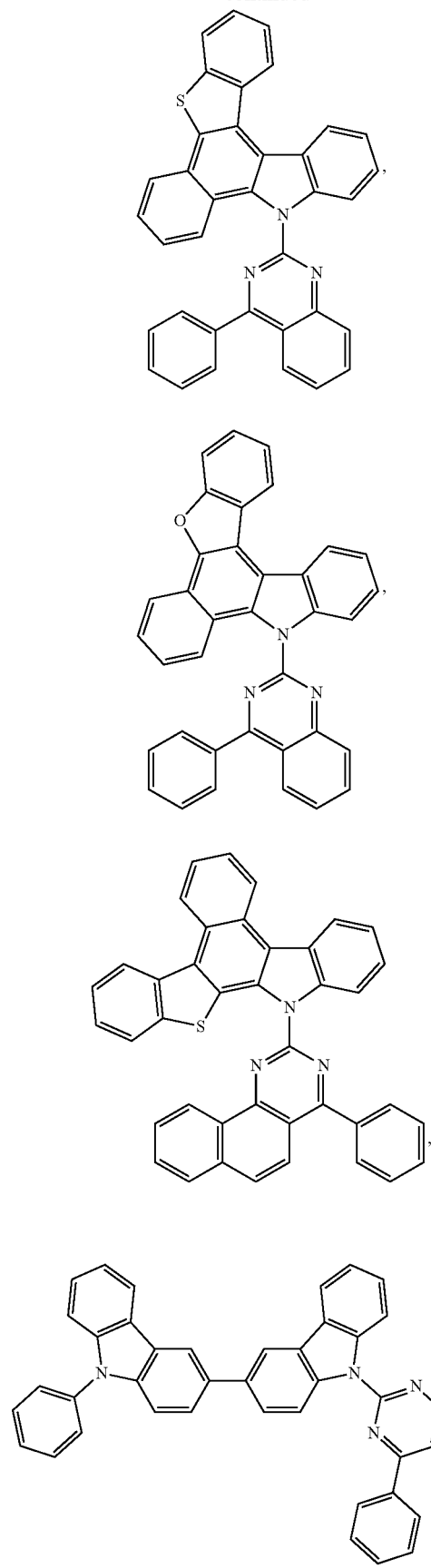
134
-continued
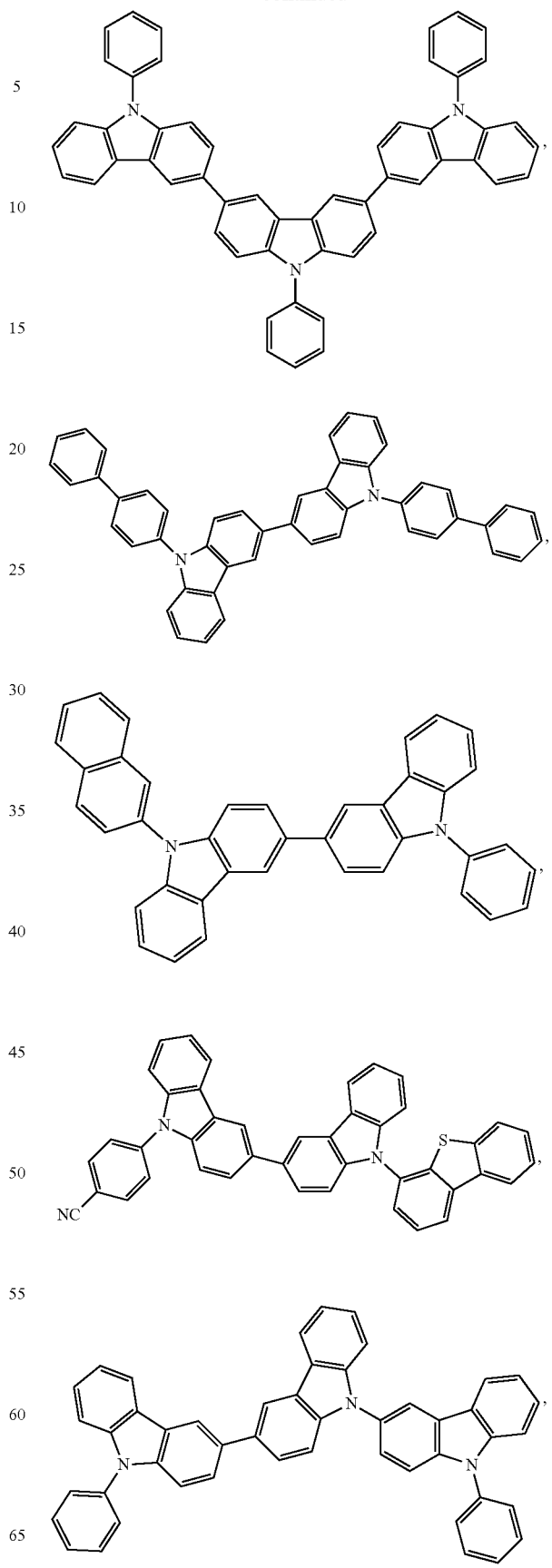

-continued

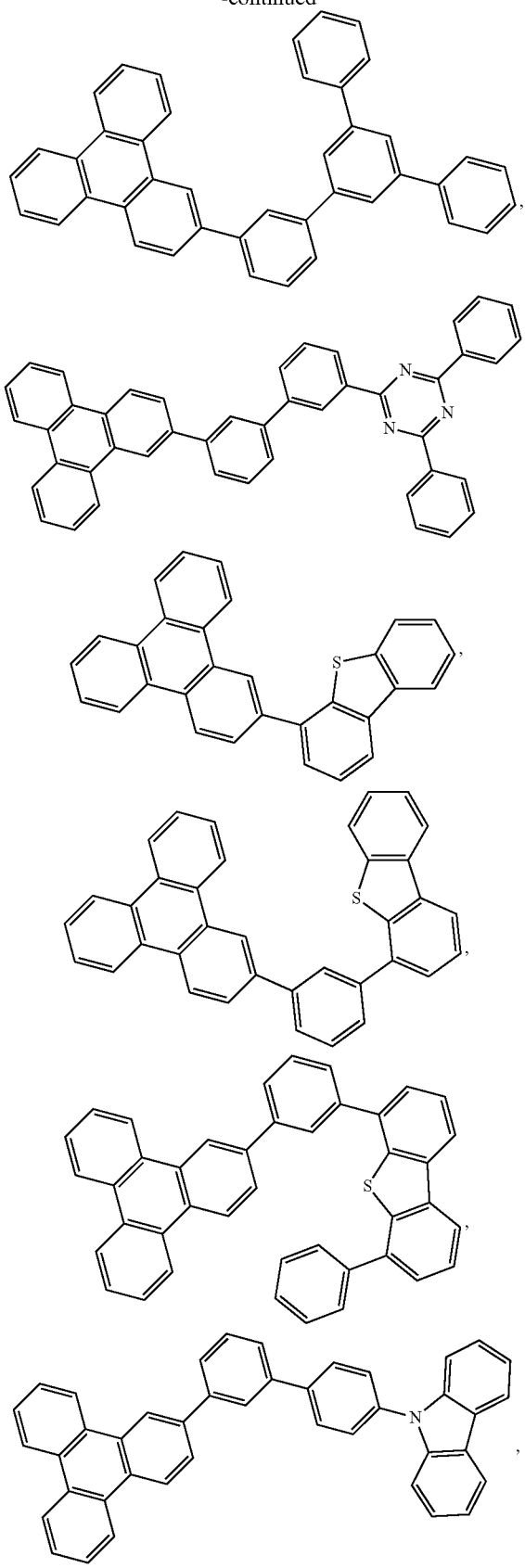

-continued

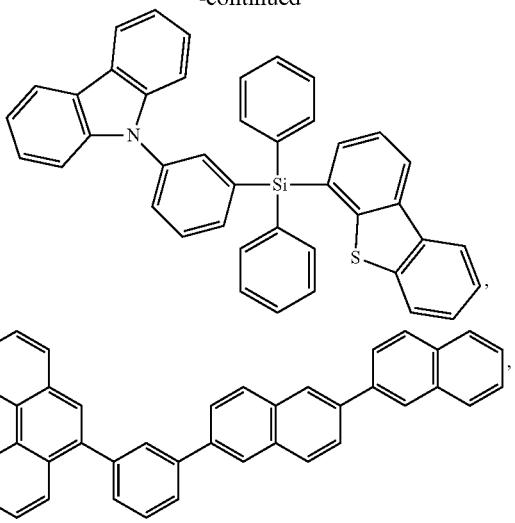

and combinations thereof.

17. A consumer product comprising an organic light-emitting device (OLED) comprising:
   an anode;
   a cathode; and
   an organic layer, disposed between the anode and the cathode, comprising a compound having a metal coordination complex structure;
   wherein the compound is capable of functioning as a phosphorescent emitter in an organic light emitting device at room temperature;
   wherein the compound has a first bidentate ligand coordinated to a metal;
   wherein the first bidentate ligand comprises a first benzene ring coordinated to the metal;
   wherein the metal is iridium;
   wherein the first benzene ring is fused with a second aromatic ring;
   wherein the second aromatic ring is fused with a third aromatic ring;
   wherein a free-state of the first ligand has a first triplet energy T1 of $E_L$ at 77K;
   wherein the compound has a first triplet energy T1 of E at 77K;
   wherein the difference in energy between E and $E_L$ is $\Delta E$;
   wherein $\Delta E$ is $\leq 250$ meV; and
   wherein the compound has a triplet emission spectrum with a full width at half maximum (FWHM) value of no more than 45 nm at 22° C.

18. The consumer product of claim 17, wherein the consumer product is selected from the group consisting of a flat panel display, a curved display, a computer monitor, a medical monitor, a television, a billboard, a light for interior or exterior illumination and/or signaling, a heads-up display, a fully or partially transparent display, a flexible display, a rollable display, a foldable display, a stretchable display, a laser printer, a telephone, a mobile phone, a tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, and a sign.

* * * * *